US005792778A

United States Patent [19]
de Laszlo et al.

[11] Patent Number: 5,792,778
[45] Date of Patent: Aug. 11, 1998

[54] 2-SUBSTITUTED ARYL PYRROLES, COMPOSITIONS CONTAINING SUCH COMPOUNDS AND METHODS OF USE

[75] Inventors: Stephen E. de Laszlo, Rumson, N.J.; Nigel J. Liverton, Harleysville, Pa.; Gerald S. Ponticello, Lansdale, Pa.; Harold G. Selnick, Ambler, Pa.; Nathan B. Mantlo, Lafayette, Colo.

[73] Assignee: Merck & Co., Inc., Rahway, N.J.

[21] Appl. No.: 694,008

[22] Filed: Aug. 8, 1996

Related U.S. Application Data

[60] Provisional application No. 60/002,093 Aug. 10, 1995 and 60/014,181 Mar. 26, 1996.

[51] Int. Cl.⁶ .......................... A61K 31/40; A61K 31/44; A61K 31/445; C07D 207/325; C07D 213/06; C07D 213/33; C07D 295/06; C07D 401/04

[52] U.S. Cl. .......................... 514/318; 514/326; 514/327; 514/330; 514/333; 514/347; 514/352; 514/354; 514/427; 546/184; 546/193; 546/208; 546/216; 546/223; 546/244; 546/248; 548/518; 548/530; 548/541; 548/564

[58] Field of Search .......................... 514/318, 326, 514/327, 330, 333, 347, 352, 354, 427; 546/184, 193, 208, 216, 223, 244, 248; 548/518, 530, 541, 564

[56] References Cited

U.S. PATENT DOCUMENTS

| | | |
|---|---|---|
| 5,286,742 | 2/1994 | Henegar et al. |
| 5,442,060 | 8/1995 | Jikihara et al. .......................... 544/106 |
| 5,502,051 | 3/1996 | Scharfenberg et al. .......... 514/235.5 |

FOREIGN PATENT DOCUMENTS

| | | |
|---|---|---|
| 0 025 884 | 4/1981 | European Pat. Off. . |
| 0 287 890 A1 | 10/1988 | European Pat. Off. . |
| 0 300 688 A1 | 1/1989 | European Pat. Off. . |
| 0 320 628 A1 | 6/1989 | European Pat. Off. . |
| 298 913 A5 | 10/1983 | Germany . |
| 298 915 A5 | 10/1983 | Germany . |
| 1099500 | 1/1968 | United Kingdom . |
| WO 91/02731 | 3/1991 | WIPO . |
| WO 94/15932 | 7/1994 | WIPO . |
| WO 95/00501 | 1/1995 | WIPO . |
| WO96/17841 | 6/1996 | WIPO . |

OTHER PUBLICATIONS

Heterocycles, vol. 35, No. 2, pp. 1171–1184 (1993), by Konakahara, et al.
Journal of Heterocyclic Chemistry, vol. 26, No. 2, pp. 489–492 (1989), by Silverstri, et al.
Journal of Heterocyclic Chemistry, vol. 29, No. 7, pp. 1847–1850 (1992) by Silvestri, et al.
Journal of the Chemical Society, J.C.S. Perkin 1, vol. 10, pp. 2642–2646 (1981), by Petruso, et al.

*Primary Examiner*—José G. Dees
*Assistant Examiner*—Jane C. Oswecki
*Attorney, Agent, or Firm*—Elliott Korsen; Mark R. Daniel

[57] ABSTRACT

The present invention addresses 2-substituted aryl pyrroles, as well as compositions containing such compounds and methods of treatment. Cytokine mediated diseases refers to diseases or conditions in which excessive or unregulated production or activity of one or more cytokines occurs. Interleukin-1 (IL-1), Interleukin-6 (IL-6), Interleukin-8 (IL-8) and Tumor Necrosis Factor (TNF) are cytokines which are involved.

13 Claims, No Drawings

2-SUBSTITUTED ARYL PYRROLES, COMPOSITIONS CONTAINING SUCH COMPOUNDS AND METHODS OF USE

CROSS REFERENCE TO RELATED APPLICATIONS

This application is a non-provisional application based upon U.S. application Ser. No. 60/002.093 filed on Aug. 10, 1995 and U.S. application Ser. No. 60/014,181 filed on Mar. 26, 1996, priority of which is claimed hereunder.

BACKGROUND OF THE INVENTION

The present invention addresses 2-substituted aryl pyrroles, as well as compositions containing such compounds and methods of treatment.

Cytokine mediated diseases refers to diseases or conditions in which excessive or unregulated production of one or more cytokines occurs. Interleukin-1 (IL-1) and Tumor Necrosis Factor (TNF) are cytokines produced by a variety of cells, which are involved in immunoregulation and other physiological conditions, such as inflammation.

IL-1 has been demonstrated to mediate a variety of biological activities. [See, e.g., Dinarello et al., Rev. Infect. Disease, 6, 51 (1984)]. The myriad of known biological activities of IL-1 include the activation of T-helper cells, induction of fever, stimulation of prostaglandin or collagenase production, neutrophil chemotaxis, induction of acute phase proteins and the suppression of plasma iron levels.

There are many disease states in which IL-1 is implicated. Included among these diseases are rheumatoid arthritis, osteoarthritis, endotoxemia, toxic shock syndrome, other acute or chronic inflammatory diseases, such as the inflammatory reaction induced by endotoxin or inflammatory bowel disease; tuberculosis, atherosclerosis, muscle degeneration, cachexia, psoriatic arthritis, Reiter's syndrome, rheumatoid arthritis, gout, traumatic arthritis, rubella arthritis and acute synovitis. Recent evidence also links IL-1 activity to diabetes and pancreatic β cells.

Excessive or unregulated TNF production has been implicated in mediating or exacerbating rheumatoid arthritis, rheumatoid spondylitis, osteoarthritis, gouty arthritis, and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcosis, bone resorption diseases, reperfusion injury, graft v. host reaction, allograft rejections, fever and myalgias due to infection, such as influenza, cachexia secondary to infection or malignancy, cachexia secondary to acquired immune deficiency syndrome (AIDS), AIDS related complex (ARC), keloid formation, scar tissue formation, Crohn's disease, ulcerative colitis and pyresis.

Monokines, such as TNF, have been shown to activate HIV replication in monocytes and/or macrophages [See Poli, et al., Proc. Natl. Acad. Sci., 87:782–784 (1990)]. Therefore, inhibition of monokine production or activity aids in limiting HIV progression as stated above for T-cells. TNF has also been implicated in various roles with other viral infections, such as the cytomegalo virus (CMV), influenza virus and the herpes virus.

IL-6 is a cytokine effecting the immune system, hematopoiesis and acute phase reactions. It is produced by several mammalian cell types in response to agents such as IL-1 and is correlated with disease states such as angiofollicular lymphoid hyperplasia.

Interleukin-8 (IL-8) is a chemotactic factor first identified and characterized in 1987. Many different names have been applied to IL-8, such as neutrophil attractant/activation protein-1 (NAP-1), monocyte derived neutrophil chemotactic factor (MDNCF), neutrophil activating factor (NAF), and T-cell lymphocyte chemotactic factor. Like IL-1, IL-8 is produced by several cell types, including mononuclear cells, fibroblasts, and endothelial cells. Its production is induced by L-1, TNF and by lipopolysaccharide (LPS). IL-8 stimulates a number of cellular functions in vitro. It is a chemoattractant for neutrophils, T-lymphocytes and basophils. It induces histamine release from basophils. It causes lysozomal enzyme release and respiratory burst from neutrophils, and it has been shown to increase the surface expression of Mac-1 (CD11b/CD 18) on neutrophils without de novo protein synthesis. There remains a need for treatment, in this field, for compounds which are cytokine suppressive or antagonistic, i.e., compounds which are capable of interfering with, inhibiting or antagonizing cytokines such as IL-1, IL-6, IL-8 and TNF.

The compounds of formula I are also useful in treating diseases characterized by excessive IL-8 activity. There are many disease states in which excessive or unregulated IL-8 production is implicated in exacerbating and/or causing the disease. These diseases include psoriasis, inflammatory bowel disease, asthma, cardiac and renal reperfusion injury, adult respiratory distress syndrome, thrombosis and glomerulonephritis.

The compounds in the present invention are used for the treatment of cytokine mediated diseases.

SUMMARY OF THE INVENTION

The present invention is directed to a compound represented by formula I:

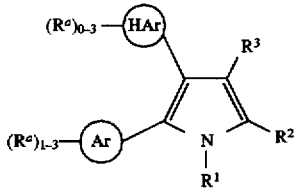

or a pharmaceutically acceptable salt thereof, wherein:
Ar represents a $C_{5-10}$ aryl or heteroaryl group, said aryl or heteroaryl group being substituted with 1–3 groups selected from $R^a$;

represents a heteroaryl group containing from 5 to 10 atoms, 1–4 of which are heteroatoms, 0–4 of which heteroatoms are N and 0–1 of which are O or S, said heteroaryl group being unsubstituted or substituted with 1–3 $R^a$ groups;

each $R^a$ independently represents a member selected from the group consisting of: halo; CN, $NO_2$, $R^{21}$; $OR^{23}$; $SR^{23}$; $S(O)R^{21}$; $SO_2R^{21}$; $NR^{20}R^{23}$; $NR^{20}COR^{21}$; $NR^{20}CO_2R^{21}$; $NR^{20}CONR^{20}R^{23}$; $NR^{20}SO_2R^{21}$; $NR^{20}C(NR^{20})NHR^{20}$, $CO_2R^{23}$; $CONR^{20}R^{23}$; $SO_2NR^{20}R^{23}$; $SO_2NR^{20}COR^{21}$; $SO_2NR^{20}CONR^{20}R^{23}$; $OCONR^{20}R^{23}$; $OCONR20SO_2R^{20}C(NR^{20})NR^{20}R^{23}$; $CONR^{20}SO_2R^{21}$ and $SO_2NR^{20}CO_2R^{21}$;

$R_1$ is selected from the group consisting of: H; $C_{1-15}$ alkyl, $C_{2-15}$ alkenyl, $C_{2-15}$ alkynyl, aryl and heterocyclyl, said alkyl, alkenyl, aryl, alkynyl and heterocyclyl being optionally substituted with from one to three members selected from the group consisting of: aryl, heteroaryl, $OR^{20}$, $SR^{20}$, $N(R^{20})_2$, $S(O)R^{21}$, $SO_2R^{21}$, $SO_2N(R^{20})_2$, $SO_2NR^{20}COR^{21}$, $SO_2NR^{20}CONR^{20}R^{23}$, $NR^{20}COR^{21}$, $NR^{20}CO_2R^{21}$, $NR^{20}CONR^{20}R^{23}$, $N(R^{20})C(NR^{20})NHR^{20}$, $CO_2R^{20}$, $CONR^{20}R^{23}$, $CONR^{20}SO_2R^{21}$, $NR^{20}SO_2R^{21}$, $SO_2NR^{20}CO_2R^{21}$, $OCONR^{20}R^{23}$, $OCONR^{20}SO_2R^{21}$, and $C(O)OCH_2OC(O)R^{20}$;

$R^2$ is selected from the group consisting of: $C_{1-15}$ alkyl, $C_{2-15}$ alkenyl, and $C_{2-15}$ alkynyl, heterocyclyl, said alkyl, alkenyl and alkynyl optionally interrupted by 1–2 oxo or heteroatoms selected from O, S, S(O), $SO_2$, or $NR^{24}$; said alkyl, alkenyl, alkynyl and heterocyclyl being optionally substituted with from 1–3 of halo, heterocyclyl, aryl$(R^a)_{0-3}$, heteroaryl, $OR^{20}$, $SR^{20}$, $NR^{20}R^{23}$, $S(O)R^{23}$, $SO_2R^{23}$, $SO_2NR^{20}R^{23}$, $SO_2NR^{20}COR^{21}$, $SO_2NR^{20}CONR^{20}R^{21}$, $NR^{20}COR^{23}$, $NR^{20}CO_2R^{23}$, $NR^{20}CONR^{20}R^{23}$, $N(R^{20})C(NR^{20})NHR^{20}$, $CO_2R^{20}$, $CONR^{20}R^{23}$, $CONR^{20}SO_2R^{21}$, $NR^{20}SO_2R^{21}$, $SO_2NR^{20}CO_2R^{21}$, $OCONR^{20}SO_2R^{23}$ and $OCONR^{20}R^{21}$;

$R^3$ is selected from the group consisting of: H, $C_{1-15}$ alkyl, $C_{2-15}$ alkenyl, $C_{2-15}$ alkynyl, halo, $CF_3$, $OCF_3$, $NO_2$, heterocyclyl, CN, $S(O)R^{21}$, $SO_2R^{21}$, $COR^{20}$, $SO_2NR^{20}R^{23}$, $SO_2NR^{20}COR^{21}$, $SO_2NR^{20}CONR^{20}R^{23}$, $CO_2R^{20}$, $CONR^{20}R^{23}$, $CONR^{20}SO_2R^{21}$ and $SO_2NR^{20}CO_2R^{21}$; said alkyl, alkenyl, alkynyl and heterocyclyl being optionally substituted with from one to three members selected from the group consisting of: halo, CN, aryl, heteroaryl, $OR^{20}$, $SR^{20}$, $NR^{20}R^{23}$, $S(O)R^{21}$, $SO_2R^{21}$, $SO_2NR^{20}R^{23}$, $SO_2NR^{20}COR^{21}$, $SO_2NR^{20}CONR^{20}R^{23}$, $NR^{20}COR^{21}$, $NR^{20}CO_2R^{21}$, $NR^{20}CONR^{20}R^{23}$, $NR^{20}C(NR^{20})NHR^{20}$, $CO_2R^{20}$, $CONR^{20}R^{23}$, $CONR^{20}SO_2R^{21}$, $NR^{20}SO_2R^{21}$, $SO_2NR^{20}CO_2R^{21}$, $OCONR^{20}SO_2R^{21}$ and $OCONR^{20}R^{23}$;

$R^{20}$ represents a member selected from the group consisting of: H, $C_{1-15}$ alkyl, $C_{2-15}$ alkenyl, $C_{2-15}$ alkynyl, heterocyclyl, aryl and heteroaryl, said alkyl, alkenyl, aryl, heteroaryl, heterocyclyl and alkynyl being optionally substituted with 1–3 groups selected from halo, aryl and heteroaryl;

$R^{21}$ represents a member selected from the group consisting of: $C_{1-15}$ alkyl, $C_{2-15}$ alkenyl, $C_{2-15}$ alkynyl, heterocyclyl, aryl and heteroaryl, said alkyl, alkenyl and alkynyl optionally interrupted by oxo and/or 1–2 heteroatoms selected from O, S, S(O), $SO_2$ or $NR^{24}$; said alkyl, alkenyl, alkynyl, aryl, heterocyclyl, and heteroaryl being optionally substituted with from 1–3 of halo, heterocyclyl, aryl, heteroaryl, CN, $OR^{20}$, $O((CH_2)_nO)_mR^{20}$, $NR^{20}((CH_2)_nO)_mR^{20}$ wherein n represents an integer of from 2 to 4, and m represents an integer of from 1 to 3; $SR^{20}$, $NR^{20}R^{23}$, $S(O)R^{22}$, $SO_2R^{22}$, $SO_2NR^{20}R^{23}$, $SO_2NR^{20}COR^{22}$, $SO_2NR^{20}CONR^{20}R^{23}$, $NR^{20}COR^{22}$, $NR^{20}CO_2R^{22}$, $NR^{20}CONR^{20}R^{23}$, $NR^{22}C(NR^{22})NHR^{22}$, $CO_2R^{20}$, $CONR^{20}R^{23}$, $CONR^{20}SO_2R^{22}$, $NR^{20}SO_2R^{22}$, $SO_2NR^{20}CO_2R^{22}$, $OCONR^{20}SO_2R^{22}$, and $OCONR^{20}R^{23}$;

$R^{22}$ is selected from the group consisting of: $C_{1-15}$ alkyl, $C_{2-15}$ alkenyl, $C_{2-15}$ alkynyl, heterocyclyl, aryl and heteroaryl, said alkyl, alkenyl, and alkynyl being optionally substituted with 1–3 halo, aryl or heteroaryl groups;

$R^{23}$ is $R^{21}$ or H;

$R^{24}$ is selected from aryl, $COR^{22}$, $CO_2R^{22}$, $CON(R^{20})_2$, $R^{23}$ and $SO_2R^{22}$;

and when two $R^{20}$ groups are present, when $R^{20}$ and $R^{21}$ are present, or when $R^{20}$ and $R^{23}$ are present, said two $R^{20}$ groups, $R^{20}$ and $R^{21}$ or said $R^{20}$ and $R^{23}$ may be taken in combination with the atoms to which they are attached and any intervening atoms and represent heterocyclyl containing from 5–10 atoms, at least one atom of which is a heteroatom selected from O, S or N, said hetercyclyl optionally containing 1–3 additional N atoms and 0–1 additional O or S atom.

Also included in the invention is a pharmaceutical composition which is comprised of a compound of formula I in combination with a pharmaceutically acceptable carrier.

Also include in the invention is a method of treating a cytokine mediated disease in a mammal, comprising administering to a mammalian patient in need of such treatment an amount of a compound of formula I which is effective to treat said cytokine mediated disease.

Also included in the invention is a method of treating diabetes in a mammalian patient in need of such treatment, comprising administering to said patient an anti-diabetic effective amount of a compound of formula I.

DETAILED DESCRIPTION OF THE INVENTION

The invention is described herein in detail using the terms defined below unless otherwise specified.

The term "alkyl" refers to a monovalent alkane (hydrocarbon) derived radical containing from 1 to 15 carbon atoms unless otherwise defined. It may be straight, branched or cyclic. Preferred straight or branched alkyl groups include methyl, ethyl, propyl, isopropyl, butyl and t-butyl. Preferred cycloalkyl groups include cyclopentyl and cyclohexyl.

Alkyl also includes a straight or branched alkyl group which contains or is interrupted by a cycloalkylene portion. Examples include the following:

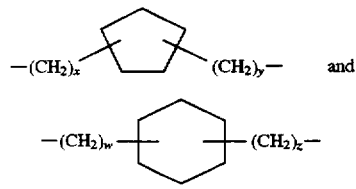

wherein: x plus y=from 0–10; and w plus z=from 0–9.

The alkylene and monovalent alkyl portion(s) of the alkyl group can be attached at any available point of attachment to the cycloalkylene portion.

When substituted alkyl is present, this refers to a straight, branched or cyclic alkyl group as defined above, substituted with 1–3 groups as defined with respect to each variable.

The term "alkenyl" refers to a hydrocarbon radical straight, branched or cyclic containing from 2 to 15 carbon atoms and at least one carbon to carbon double bond. Preferably one carbon to carbon double bond is present, and up to four non-aromatic (non-resonating) carbon-carbon double bonds may be present. Preferred alkenyl groups include ethenyl, propenyl, butenyl and cyclohexenyl. As described above with respect to alkyl, the straight, branched or cyclic portion of the alkenyl group may contain double bonds and may be substituted when a substituted alkenyl group is provided.

The term "alkynyl" refers to a hydrocarbon radical straight, branched or cyclic, containing from 2 to 15 carbon atoms and at least one carbon to carbon triple bond. Up to three carbon-carbon triple bonds may be present. Preferred alkynyl groups include ethynyl, propynyl and butynyl. As described above with respect to alkyl, the straight, branched or cyclic portion of the alkynyl group may contain triple bonds and may be substituted when a substituted alkynyl group is provided.

Aryl refers to aromatic rings e.g., phenyl, substituted phenyl and like groups as well as rings which are fused, e.g., naphthyl and the like. Aryl thus contains at least one ring having at least 6 atoms, with up to two such rings being present, containing up to 10 atoms therein, with alternating (resonating) double bonds between adjacent carbon atoms. The preferred aryl groups are phenyl and naphthyl. Aryl groups may likewise be substituted as defined below. Preferred substituted aryls include phenyl and naphthyl substituted with one or two groups.

The group  represents a 5–10 membered aryl or heteroaryl which is substituted with 1–3 groups selected from $R^a$ such that a total of 1 to 4 groups are attached to . Preferred  are phenyl and naphthyl.

The term "heteroaryl" refers to a monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one additional carbon atom is optionally replaced by a heteroatom selected from O or S, and in which from 1 to 3 additional carbon atoms are optionally replaced by nitrogen heteroatoms. The heteroaryl group is optionally substituted with up to three groups.

Heteroaryl thus includes aromatic and partially aromatic groups which contain one or more heteroatoms. Examples of this type are thiophene, purine, imidazopyridine, pyridine, oxazole, thiazole, oxazine, pyrazole, tetrazole, imidazole, pyridine, pyrimidine and pyrazine and triazine.

The group (HAr)

thus represents a heteroaryl group which contains from 5 to 10 atoms. One to three atoms are heteroatoms which are selected from O, S and N. In addition, there may be up to three additional nitrogen atoms, and 0–1 additional O or S. The heteroaryl group may be unsubstituted or substituted with up to 3 $R^a$ groups. HAr is carbon linked except where it is a purinyl, imidazolyl or imidazopyridine in which case it may be attached at the nitrogen or carbon atom.

Preferred heteroaryl groups represented by (HAr)

are as follows: pyridyl, quinolyl, purinyl, imidazolyl, imidazopyridyl and pyrimidinyl.

The terms "heterocycloalkyl" and "heterocyclyl" refer to a cycloalkyl group (nonaromatic) in which one of the carbon atoms in the ring is replaced by a heteroatom selected from O, S, SO, $SO_2$ or N, and in which up to three additional carbon atoms may be optionally replaced by heteroatoms.

Heterocyclyl is carbon or nitrogen linked; if carbon linked and contains a nitrogen, then the nitrogen may be substituted by $R^{24}$. Examples of heterocyclyls are piperidinyl, morpholinyl, pyrrolidinyl, tetrahydrofuranyl, tetrahydroimidazo[4,5-c]pyridinyl, imidazolinyl, piperazinyl, pyrrolidine-2-onyl, piperidin-2-onyl and the like.

The term "TNF mediated disease or disease state" refers to any and all disease states in which TNF plays a role, either by production of TNF itself, or by TNF causing another monokine to be released, such as but not limited to IL-1 or IL-6. A disease state in which IL-1, for instance, is a major component, and whose production or action, is exacerbated or secreted in response to TNF, would therefore be considered a disease state mediated by TNF.

The term "cytokine" as used herein is meant any secreted polypeptide that affects the functions of cells and is a molecule which modulates interactions between cells in the immune, inflammatory or hematopoietic response. A cytokine includes, but is not limited to, monokines and lymphokines regardless of which cells produce them. Examples of cytokines include, but are not limited to, Interleukin-1 (IL-1), Interleukin-6 (IL-6), Interleukin-8 (IL-8), Tumor Necrosis Factor-alpha (TNF-α) and Tumor Necrosis Factor-beta (TNF-β).

By the term "cytokine antagonizing, interfering or cytokine suppressive amount" is meant an amount of a compound of formula I which will, cause a decrease in the in vivo activity level of the cytokine to normal or sub-normal levels, when given to the patient for the prophylaxis or therapeutic treatment of a disease state which is exacerbated by, or caused by, excessive or unregulated cytokine production or activity.

The compounds of the present invention may contain one or more asymmetric carbon atoms and may exist in racemic and optically active forms. All of these compounds are contemplated to be within the scope of the present invention.

Throughout the instant application, the following abbreviations are used with the following meanings:

| | |
|---|---|
| Bu | butyl |
| Bn | benzyl |
| BOC, Boc | t-butyloxycarbonyl |
| calc. | calculated |
| CBZ, Cbz | Benzyloxycarbonyl |
| CDI | N,N'-carbonyl diimidazole |
| FAB-MS | Fast atom bombardment-mass spectroscopy |
| HPLC | High pressure liquid chromatography |
| KHMDS | Potassium bis(trimethylsilyl)amide |
| LAH | Lithium aluminum hydride |
| LHMDS | Lithium bis(trimethylsilyl)amide |
| Me | methyl |
| MeOH | methanol |
| MPLC | Medium pressure liquid chromatography |
| NMR | Nuclear Magnetic Resonance |
| Ph | phenyl |
| Pr | propyl |
| prep. | prepared |
| Pyr. | pyridyl |
| TMS | Trimethylsilyl |

One subset of compounds of the invention relates to compounds of formula I wherein  represents a member selected from the group consisting of: phenyl, pyridyl, pyrimidinyl, thiophenyl, furanyl, imidazolyl, thiazolyl, isothiazolyl, oxazolyl and isoxazolyl. Within this subset, all other variables are as originally defined.

Another subset of compounds of the invention relates to compounds of formula I wherein $R^a$ is selected from the group consisting of: halo, CN, $R^{21}$, $OR^{23}$, $CO_2R^{23}$ and $CONR^{20}R^{23}$. Within this subset, all other variables are as originally defined.

Another subset of compounds of the invention relates to compounds of formula I wherein (HAr)

represents a member selected from the group consisting of: pyridyl, quinolyl, purinyl, imidazolyl, pyrimidinyl and imidazopyridyl. Within this subset, all other variables are as originally defined.

Another subset of compounds of the invention relates to compounds of formula I wherein $R^1$ is a member selected from the group consisting of: H, $C_{1-15}$ alkyl and $C_{1-15}$ alkyl substituted as originally defined. Within this subset, all other variables are as originally defined.

Another subset of compounds of the invention relates to compounds of formula I wherein $R^2$ represents a member selected from one of the following groups:

a) —$C_{1-7}$-straight or branched alkyl optionally interrupted by oxo or $NR^{24}$ and optionally substituted by 1–3 groups selected from the group consisting of: halo, heterocyclyl, aryl$(R^a)_{0-3}$, heteroaryl, $OR^{20}$, $SR^{20}$, $NR^{20}R^{23}$, $S(O)R^{23}$, $SO_2R^{23}$, $SO_2NR^{20}R^{23}$, $SO_2NR^{20}COR^{21}$, $SO_2NR^{20}CONR^{20}R^{21}$, $NR^{20}COR^{23}$, $NR^{20}CO_2R^{23}$, $NR^{20}CONR^{20}R^{23}$, $N(R^{20})C(NR^{20})NHR^{20}$, $CO_2R^{20}$, $CONR^{20}R^{23}$, $CONR^{20}SO_2R^{21}$, $NR^{20}SO_2R^{21}$, $SO_2NR^{20}CO_2R^{21}$, $OCONR^{20}SO_2R^{23}$ and $OCONR^{20}R^{21}$;

b) —$C_{4-7}$-cycloalkyl optionally interrupted by oxo or $NR^{24}$ and optionally substituted by 1–3 groups selected from the group consisting of: halo, heterocyclyl, aryl $(R^a)_{0-3}$, heteroaryl, $OR^{20}$, $SR^{20}$, $NR^{20}R^{23}$, $S(O)R^{23}$, $SO_2R^{23}$, $SO_2NR^{20}R^{23}$, $SO_2NR^{20}COR^{21}$, $SO_2NR^{20}CONR^{20}R^{21}$, $NR^{20}COR^{23}$, $NR^{20}CO_2R^{23}$, $NR^{20}CONR^{20}R^{23}$, $N(R^{20})C(NR^{20})NHR^{20}$, $CO_2R^{20}$, $CONR^{20}R^{23}$, $CONR^{20}SO_2R^{21}$, $NR^{20}SO_2R^{21}$, $SO_2NR^{20}CO_2R^{21}$, $OCONR^{20}So2R^{23}$ and $OCONR^{20}R^{21}$;

c) —$C_{1-4}$-alkyl-aminoacyl-$C_{2-6}$-alkyl, the alkyl portions thereof being optionally interrupted by oxo or $NR^{24}$, and optionally substituted by 1–3 groups selected from the group consisting of: halo, heterocyclyl, aryl$(R^a)_{0-3}$, heteroaryl, $OR^{20}$, $SR^{20}$, $NR^{20}R^{23}$, $S(O)R^{23}$, $SO_2R^{23}$, $SO_2NR^{20}R^{23}$, $SO_2NR^{20}COR^{21}$, $SO_2NR^{20}CONR^{20}R^{21}$, $NR^{20}COR^{23}$, $NR^{20}CO_2R^{23}$, $NR^{20}CONR^{20}R^{23}$, $N(R^{20})C(NR^{20})NHR^{20}$, $CO_2R^{20}$, $CONR^{20}R^{23}$, $CONR^{20}SO_2R^{21}$, $NR^{20}SO_2R^{21}$, $SO_2NR^{20}CO_2R^{21}$, $OCONR^{20}SO_2R^{23}$ and $OCONR^{20}R^{21}$;

d) —$C_{1-4}$-alkyl-aminoacyl-$C_{4-7}$-cycloalkyl, the alkyl portions thereof being optionally interrupted by oxo or $NR^{24}$, and optionally substituted by 1–3 groups selected from the group consisting of: halo, heterocyclyl, aryl$(R^a)_{0-3}$, heteroaryl, $OR^{20}$, $SR^{20}$, $NR^{20}R^{23}$, $S(O)R^{23}$, $SO_2R^{23}$, $SO_2NR^{20}R^{23}$, $SO_2NR^{20}COR^{21}$, $SO_2NR^{20}CONR^{20}R^{21}$, $NR^{20}COR^{23}$, $NR^{20}OCO_2R^{23}$, $NR^{20}CONR^{20}R^{23}$, $N(R^{20})C(NR^{20})NHR^{20}$, $CO_2R^{20}$, $CONR^{20}R^{23}$, $CONR^{20}SO_2R^{21}$, $NR^{20}SO_2R^{21}$, $SO_2NR^{20}CO_2R^{21}$, $OCONR^{20}SO_2R^{23}$ and $OCONR^{20}R^{21}$;

e) —$C_{1-4}$-alkyl-aminoacylamino-$C_{2-6}$-alkyl, the alkyl portions thereof being optionally interrupted by oxo or $NR^{24}$, and optionally substituted by 1–3 groups selected from the group consisting of: halo, heterocyclyl, aryl$(R^a)_{0-3}$, heteroaryl, $OR^{20}$, $SR^{20}$, $NR^{20}R^{23}$, $S(O)R^{23}$, $SO_2R^{23}$, $SO_2NR^{20}R^{23}$, $SO_2NR^{20}COR^{21}$, $SO_2NR^{20}CONR^{20}R^{21}$, $NR^{20}COR^{23}$, $NR^{20}CO_2R^{23}$, $NR^{20}CONR^{20}R^{23}$, $N(R^{20})C(NR^{20})NHR^{20}$, $CO_2R^{20}$, $CONR^{20}R^{23}$, $CONR^{20}SO_2R^{21}$, $NR^{20}SO_2R^{21}$, $SO_2NR^{20}CO_2R^{21}$, $OCONR^{20}SO_2R^{23}$ and $OCONR^{20}R^{21}$; and f) —$C_{1-4}$-alkyl-aminoacylamino-$C_{4-7}$-cycloalkyl, the alkyl portions thereof being optionally interrupted by oxo or $NR^{24}$, and optionally substituted by 1–3 groups selected from the group consisting of: halo, heterocyclyl, aryl$(R^a)_{0-3}$, heteroaryl, $OR^{20}$, $SR^{20}$, $NR^{20}R^{23}$, $S(O)R^{23}$, $SO_2R^{23}$, $SO_2NR^{20}R^{23}$, $SO_2NR^{20}COR^{21}$, $SO_2NR^{20}CONR^{20}R^{21}$, $NR^{20}COR^{23}$, $NR^{20}OCO_2R^{23}$, $NR^{20}CONR^{20}R^{23}$, $N(R^{20})C(NR^{20})NHR^{20}$, $CO_2R^{20}$, $CONR^{20}R^{23}$, $CONR^{20}SO_2R^{21}$, $NR^{20}SO_2R^{21}$, $SO_2NR^{20}CO_2R^{21}$, $OCONR^{20}SO_2R^{23}$ and $OCONR^{20}R^{21}$. The point of attachment to the pyrrole is from the left hand side of the items listed in a through f. Within this subset, all other variables are as originally defined.

Another subset of compounds of the invention relates to compounds of formula I wherein $R^3$ represents a member selected from the group consisting of:

a) H,
b) alkyl,
c) halo,
d) $CO_2R^{20}$,
e) $CONR^{20}R^{23}$ and
f) CN.

Within this subset, all other variables are as originally defined.

A preferred subset of compounds of the invention relates to compounds of formula I wherein:

(Ar) is selected from the group consisting of:
a) phenyl,
b) pyridyl,
c) pyrimidinyl,
d) thiophenyl,
e) furanyl,
f) imidazolyl,
g) thiazolyl,
h) isothiazolyl,
i) oxazolyl, and
j) isoxazolyl;

$R^a$ represents a member selected from the group consisting of: halo, CN, $R^{21}$, $OR^{23}$, $CO_2R^{23}$ and $CONR^{20}R^{23}$;

(HAr)

is selected from the group consisting of:
a) pyridyl,
b) quinolyl,
c) purinyl,
d) imidazolyl,
e) pyrimidinyl and
f) imidazopyridine;

$R^1$ is:
a) H or
b) $C_{1-15}$ alkyl unsubstituted or substituted with 1–3 groups selected from the group consisting of: aryl, heteroaryl, $OR^{20}$, $SR^{20}$, $N(R^{20})_2$, $S(O)R^{21}$, $SO_2R^{21}$, $SO_2N(R^{20})_2$, $SO_2NR^{20}COR^{21}$, $SO_2NR^{20}CONR^{20}R^{23}$, $NR^{20}COR^{21}$, $NR^{20}CO_2R^{21}$, $NR^{20}CONR^{20}R^{23}$, $N(R^{20})C(NR^{20})NHR^{20}$, $CO_2R^{20}$, $CONR^{20}R^{23}$, $CONR^{20}SO_2R^{21}$, $NR^{20}SO_2R^{21}$, $SO_2NR^{20}CO_2R^{21}$, $OCONR^{20}R^{23}$, $OCONR^{20}SO_2R^{21}$ and $C(O)OCH_2OC(O)R^{20}$;

$R^2$ is selected from the group consisting of:

a) —$C_{1-7}$-straight or branched alkyl optionally interrupted by oxo or $NR^{24}$, and optionally substituted by 1–3 groups selected from the group consisting of: halo, heterocyclyl, aryl$(R^a)_{0-3}$, heteroaryl, $OR^{20}$, $SR^{20}$, $NR^{20}R^{23}$, $S(O)R^{23}$, $SO_2R^{23}$, $SO_2NR^{20}R^{23}$, $SO_2NR^{20}COR^{21}$, $SO_2NR^{20}CONR^{20}R^{21}$, $NR^{20}COR^{23}$, $NR^{20}CO_2R^{23}$, $NR^{20}CONR^{20}R^{23}$, $N(R^{20})C(NR^{20})NHR^{20}$, $CO_2R^{20}$, $CONR^{20}R^{23}$, $CONR^{20}SO_2R^{21}$, $NR^{20}SO_2R^{21}$, $SO_2NR^{20}CO_2R^{21}$, $OCONR^{20}SO_2R^{23}$ and $OCONR^{20}R^{21}$;

b) —$C_{4-7}$-cycloalkyl optionally interrupted by oxo or $NR^{24}$, and optionally substituted by 1–3 groups selected from the group consisting of: halo, heterocyclyl, aryl$(R^a)_{0-3}$, heteroaryl, $OR^{20}$, $SR^{20}$, $NR^{20}R^{23}$, $S(O)R^{23}$, $SO_2R^{23}$, $SO_2NR^{20}R^{23}$, $SO_2NR^{20}COR^{21}$, $SO_2NR^{20}CONR^{20}R^{21}$, $NR^{20}COR^{23}$, $NR^{20}CO_2R^{23}$, $NR^{20}CONR^{20}R^{23}$, $N(R^{20})C(NR^{20})NHR^{20}$, $CO_2R^{20}$, $CONR^{20}R^{23}$, $CONR^{20}SO_2R^{21}$, $NR^{20}SO_2R^{21}$, $SO_2NR^{20}CO_2R^{21}$, $OCONR^{20}SO_2R^{23}$ and $OCONR^{20}R^{21}$;

c) —$C_{1-4}$-alkyl-aminoacyl-$C_{2-6}$-alkyl, the alkyl portions thereof being optionally interrupted by oxo or $NR^{24}$, and optionally substituted by 1–3 groups selected from the group consisting of: halo, heterocyclyl, aryl$(R^a)_{0-3}$, heteroaryl, $OR^{20}$, $SR^{20}$, $NR^{20}R^{23}$, $S(O)R^{23}$, $SO_2R^{23}$, $SO_2NR^{20}R^{23}$, $SO_2NR^{20}COR^{21}$, $SO_2NR^{20}CONR^{20}R^{21}$, $NR^{20}COR^{23}$, $NR^{20}CO_2R^{23}$, $NR^{20}CONR^{20}R^{23}$, $N(R^{20})C(NR^{20})NHR^{20}$, $CO_2R^{20}$, $CONR^{20}R^{23}$, $CONR^{20}SO_2R^{21}$, $NR^{20}SO_2R^{21}$, $SO_2NR^{20}CO_2R^{21}$, $OCONR^{20}SO_2R^{23}$ and $OCONR^{20}R^{21}$;

d) —$C_{1-4}$-alkyl-aminoacyl-$C_{4-7}$-cycloalkyl, the alkyl portions thereof being optionally interrupted by oxo or $NR^{24}$, and optionally substituted by 1–3 groups selected from the group consisting of: halo, heterocyclyl, aryl$(R^a)_{0-3}$, heteroaryl, $OR^{20}$, $SR^{20}$, $NR^{20}R^{23}$, $S(O)R^{23}$, $SO_2R^{23}$, $SO_2NR^2OR^{23}$, $SO_2NR^{20}COR^{21}$, $SO_2NR^{20}CONR^{20}R^{21}$, $NR^{20}COR^{23}$, $NR^{20}CO_2R^{23}$, $NR^{20}CONR^{20}R^{23}$, $N(R^{20})C(NR^{20})NHR^{20}$, $CO_2R^{20}$, $CONR^{20}R^{23}$, $CONR^{20}SO_2R^{21}$, $NR^{20}SO_2R^{21}$, $SO_2NR^{20}CO_2R^{21}$, $OCONR^{20}SO_2R^{23}$ and $OCONR^{20}R^{21}$;

e) —$C_{1-4}$-alkyl-aminoacylamino-$C_{2-6}$-alkyl, the alkyl portions thereof being optionally interrupted by oxo or $NR^{24}$, and optionally substituted by 1–3 groups selected from the group consisting of: halo, heterocyclyl, aryl$(R^a)_{0-3}$, heteroaryl, $OR^{20}$, $SR^{20}$, $NR^{20}R^{23}$, $S(O)R^{23}$, $SO_2R^{23}$, $SO_2NR^{20}R^{23}$, $SO_2NR^{20}COR^{21}$, $SO_2NR^{20}CONR^{20}R^{21}$, $NR^{20}COR^{23}$, $NR^{20}CO_2R^{23}$, $NR^{20}CONR^{20}R^{23}$, $N(R^{20})C(NR^{20})NHR^{20}$, $CO_2R^{20}$, $CONR^{20}R^{23}$, $CONR^{20}SO_2R^{21}$, $NR^{20}SO_2R^{21}$, $SO_2NR^{20}CO_2R^{21}$, $OCONR^{20}SO_2R^{23}$ and $OCONR^{20}R^{21}$, and f) —$C_{1-4}$-alkyl-aminoacylamino-$C_{4-7}$-cycloalkyl, the alkyl portions thereof being optionally interrupted by oxo or $NR^{24}$, and optionally substituted by 1–3 groups selected from the group consisting of: halo, heterocyclyl, aryl$(R^a)_{0-3}$, heteroaryl, $OR^{20}$, $SR^{20}$, $NR^{20}R^{23}$, $S(O)R^{23}$, $SO_2R^{23}$, $SO_2NR^{20}R^{23}$, $SO_2NR^{20}COR^{21}$, $SO_2NR^{20}CONR^{20}R^{21}$, $NR^{20}COR^{23}$, $NR^{20}CO_2R^{23}$, $NR^{20}CONR^{20}R^{23}$, $N(R^{20})C(NR^{20})NHR^{20}$, $CO_2R^{20}$, $CONR^{20}R^{23}$, $CONR^{20}SO_2R^{21}$, $NR^{20}SO_2R^{21}$, $SO_2NR^{20}CO_2R^{21}$, $OCONR^{20}SO_2R^{23}$ and $OCONR^{20}R^{21}$.

$R^3$ is selected from the group consisting of:
a) H,
b) alkyl,
c) halo,
d) $CO_2R^{20}$,
e) $CONR^{20}R^{23}$ and
f) CN.

A subset of the most preferred compounds of formula I is realized when:

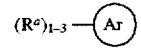

is selected from the group consisting of:
a) 4-fluorophenyl,
b) 4-chlorophenyl,
c) 3-fluorophenyl,
d) 3-chlorophenyl,
e) 4-fluorothiophen-2-yl,
f) 4-fluorothiophen-3-yl,
g) 5-fluorothiophen-2-yl,
h) 5-fluorothiophen-3-yl,
i) 4-chlorothiophen-2-yl,
j) 4-chlorothiophen-3-yl,
k) 5-chlorothiophen-2-yl,
l) 5-chlorothiophen-3-yl,
m) 3-methylphenyl,
n) 3,4-dichlorophenyl,
o) 3-hydroxyphenyl,
p) 2-chlorophenyl,
q) 4-aminomethylphenyl,
r) 4-nitrophenyl,
s) 3,4-difluorophenyl,
t) 2-methoxyphenyl,
u) 3-methoxyphenyl,
v) 4-methoxyphenyl,
w) 4-(4-(N-acetyl)-piperazinyl-phenyl,
x) 4-morpholinyl-phenyl,
y) 3-trifluoromethylphenyl,
z) 4-methylsulfinylphenyl, and
aa) 4-methylsulfonylphenyl;

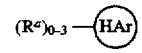

is selected from the group consisting of:
a) 4-pyridyl,
b) 4-(2-methylpyridyl),
c) 4-(2-aminopyridyl),
d) 4-(2-methoxypyridyl),
e) 4-quinolinyl,
f) 4-pyrimidinyl,
g) 9-purinyl,
h) 7-(imidazo[4,5-b]pyridyl),
i) 4-(3-methylpyridyl),
j) 2-pyrimidinyl,
k) 3-pyridazinyl,
l) 2-pyrazinyl,
m) 2-(N-t-butoxycarbonylamino)-4-pyridyl,
n) 4-(2-N-acetylamino)-pyridyl,
o) 4-(2-N-benzolylamino-3-methyl)-pyridyl and
p) 4-(2-N-benzolylamino)-pyridyl;

$R^1$ is: H;
$R^2$ is selected from the group consisting of:
a) isopropyl,
b) tert-butyl,
c) phenethyl,
d) benzyl,
e) 2-amino-2,2-dimethylethyl, f) 4-aminomethylbenzyl,
g) piperidin-4-yl,
h) piperidin-3-yl,
i) pyrrolidin-3-yl,
j) N-methylpiperidin-4-yl,
k) N-benzylpiperidin-4-yl,
l) N-(2-hydroxyethyl)piperidin-4-yl,
m) N-methanesulfonylpiperidin-4-yl,
n) isobutyl,
o) N-(benzyloxycarbonyl)-piperidin-4-yl,
p) N-morpholinylmethyl
q) N-(phenyl)-piperidin-4-yl,
r) N-(methyl)-piperidin-4-yl-methyl,
s) N-methyl-piperidin-3-yl, and $R^3$ is selected from the group consisting of:
a) H,
b) F,
c) Cl,
d) Br,
d) $CO_2R^{20}$,
e) $CONR^{20}R^{23}$ and
f) CN.

Another subset of the most preferred compounds of formula I is realized when:

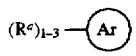

is selected from the group consisting of:
a) 4-fluorophenyl,
b) 4-chlorophenyl,
c) 3-fluorophenyl,
d) 3-chlorophenyl,
e) 4-fluorothiophen-2-yl,
f) 4-fluorothiophen-3-yl,
g) 5-fluorothiophen-2-yl,
h) 5-fluorothiophen-3-yl,
i) 4-chlorothiophen-2-yl,
j) 4-chlorothiophen-3-yl,
k) 5-chlorothiophen-2-yl,
l) 5-chlorothiophen-3-yl,
m) 3-methylphenyl,
n) 3,4-dichlorophenyl,
o) 3-hydroxyphenyl,
p) 2-chlorophenyl,
q) 4-aminomethylphenyl,
r) 4-nitrophenyl,
s) 3,4-difluorophenyl,
t) 2-methoxyphenyl,
u) 3-methoxyphenyl,
v) 4-methoxyphenyl,
w) 4-(4-(N-acetyl)-piperazinyl-phenyl,
x) 4-morpholinyl-phenyl,
y) 3-trifluoromethylphenyl,
z) 4-methylsulfinylphenyl, and
aa) 4-methylsulfonylphenyl;

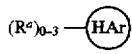

is selected from the group consisting of:
a) 4-pyridyl,
b) 4-(2-methylpyridyl),
c) 4-(2-aminopyridyl),
d) 4-(2-methoxypyridyl),
e) 4-quinolinyl,
f) 4-pyrimidinyl,
g) 9-purinyl,
h) 7-(imidazo[4,5-b]pyridyl),
i) 4-(3-methylpyridyl),
j) 2-pyrimidinyl,
k) 3-pyridazinyl,
l) 2-pyrazinyl,
m) 2-(N-t-butoxycarbonylamino)-4-pyridyl,
n) 4-(2-N-acetylamino)-pyridyl,
o) 4-(2-N-benzolylamino-3-methyl)-pyridyl and
p) 4-(2-N-benzolylamino)-pyridyl;

$R^1$ is: $C_{1-15}$ alkyl;

$R^2$ is selected from the group consisting of:
a) isopropyl,
b) tert-butyl,
c) phenethyl,
d) benzyl,
e) 2-amino-2,2-dimethylethyl,
f) 4-aminomethylbenzyl,
g) piperidin-4-yl,
h) piperidin-3-yl,
i) pyrrolidin-3-yl,
j) N-methylpiperidin-4-yl,
k) N-benzylpiperidin-4-yl,
l) N-(2-hydroxyethyl)piperidin-4-yl,
m) N-methanesulfonylpiperidin-4-yl,
n) isobutyl,
o) N-(benzyloxycarbonyl)-piperidin-4-yl,
p) N-morpholinylmethyl
q) N-(phenyl)-piperidin-4-yl,
r) N-(methyl)-piperidin-4-yl-methyl,
s) N-methyl-piperidin-3-yl, and $R^3$ is selected from the group consisting of:
a) H,
b) F,
c) Cl,
d) Br,
d) $CO_2R^{20}$,
e) $CONR^{20}R^{23}$ and
f) CN.

A further subset of compounds of the invention relates to a compound represented by formula I:

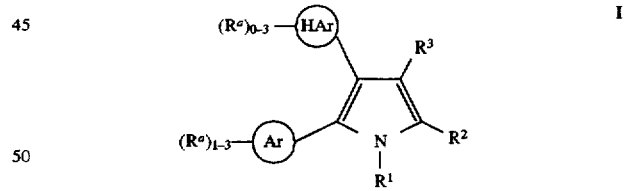

or a pharmaceutically acceptable salt thereof, wherein:
Ar represents a $C_{5-10}$ aryl or heteroaryl group, substituted with 1–3 groups selected from $R^a$;

represents a heteroaryl group containing from 5 to 10 atoms, 1–3 of which are heteroatoms, 0–3 of which heteroatoms are N and 0–1 of which are O or S, said heteroaryl group being unsubstituted or substituted with 1–3 $R^a$ groups;

each $R^a$ independently represents a member selected from the group consisting of: halo; CN, $NO_2$, $R^{21}$; $OR^{23}$; $SR^{23}$; $S(O)R^{21}$; $SO_2R^{21}$; $NR^{20}R^{23}$; $NR^{20}COR^{21}$; $NR^{20}CO_2R^{21}$; $NR^{20}CONR^{20}R^{23}$; $NR^{20}SO_2R^{21}$; $NR^2C$ $(NR^{20})NHR^{20}$, $CO_2R^{23}$; $CONR^{20}R^{23}$; $SO_2NR^{20}R^{23}$; $SO_2NR^{20}COR^{21}$; $SO_2NR^{20}OCONR^{20}R^{23}$; $SO_2NR^{20}CO_2R^{21}$; $OCONR^{20}R^{23}$; $OCONR^{20}SO_2R^{20}$ and $C(NR^{20})NR^{20}R^{23}$;

$R^1$ is selected from the group consisting of: H; $C_{1-15}$ alkyl, $C_{2-15}$ alkenyl, $C_{2-15}$ alkynyl, aryl and heterocyclyl, said alkyl, alkenyl, aryl, alkynyl and heterocyclyl being optionally substituted with from one to three members selected from the group consisting of: aryl, heteroaryl, $OR^{20}$, $SR^{20}$, $N(R^{20})_2$, $S(O)R^{21}$, $SO_2R^{21}$, $SO_2N(R^{20})_2$, $SO_2NR^{20}COR^{21}$, $SO_2NR^{20}CON(R^{20})_2$, $NR^{20}COR^{21}$, $NR^{20}CO_2R^{21}$, $NR^{20}CON(R^{20})_2$, $N(R^{20})C(NR^{20})NHR^{20}$, $CO_2R^{20}$, $CON(R^{20})_2$, $CONR^{20}SO_2R^{21}$, $NR^{20}SO_2R^{21}$, $SO_2NR^{20}CO_2R^{21}$, $OCON(R^{20})_2$, $OCONR^{20}SO_2R^{21}$, $C(O)OCH_2OC(O)R^{20}$ and $OCONR^{20}R^{23}$;

$R^2$ is selected from the group consisting of: $C_{1-15}$ alkyl, $C_{2-15}$ alkenyl, and $C_{2-15}$ alkynyl, heterocyclyl, optionally interrupted by 1–2 heteroatoms selected from O, S, S(O), $SO_2$ or $NR^{24}$; said alkyl, alkenyl, alkynyl and heterocyclyl being optionally substituted with from 1–3 of halo, aryl, heteroaryl, $OR^{20}$, $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CON(R^{20})_2$, $NR^{20}COR^{22}$, $NR^{20}CO_2R^{22}$, $NR^{20}CON(R^{20})_2$, $N(R^{22})C(NR^{22})NHR^{22}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$ and $OCONR^{20}R^{23}$;

$R^3$ is selected from the group consisting of: H, $C_{1-15}$ alkyl, $C_{2-15}$ alkenyl, $C_{2-15}$ alkynyl, halo, $CF_3$, $NO_2$ and heterocyclyl, said alkyl, alkenyl, alkynyl and heterocyclyl being optionally substituted with from one to three members selected from the group consisting of: halo, CN, aryl, heteroaryl, $OR^{20}$, $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CON(R^{20})_2$, $NR^{20}COR^{22}$, $NR^{20}CO_2R^{22}$, $NR^{20}CON(R^{20})_2$, $NR^{22}C(NR^{22})NHR^{22}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$ and $OCONR^{20}R^{23}$;

$R^{20}$ represents a member selected from the group consisting of: H, $C_{1-15}$ alkyl, $C_{2-15}$ alkenyl, $C_{2-15}$ alkynyl, heterocyclyl, aryl and heteroaryl, said alkyl, alkenyl and alkynyl being optionally substituted with 1–3 groups selected from halo, aryl and heteroaryl;

$R^{21}$ represents a member selected from the group consisting of: $C_{1-15}$ alkyl, $C_{2-15}$ alkenyl, $C_{2-15}$ alkynyl, aryl and heteroaryl, optionally interrupted by 1–2 heteroatoms selected from O, S, S(O), $SO_2$ or $NR^{24}$; said alkyl, alkenyl, alkynyl, aryl and heteroaryl being optionally substituted with from 1–3 of halo, heterocyclyl, aryl, heteroaryl, CN, $OR^{20}$, $O((CH_2)_nO)_mR^{20}$, $NR^{20}((CH_2)_nO)_mR^{20}$ wherein n represents an integer of from 2 to 4, and m represents an integer of from 1 to 3; $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CON(R^{20})_2$, $NR^{20}COR^{22}$, $NR^{20}CO_2R^{22}$, $NR^{20}CON(R^{20})_2$, $NR^{22}C(NR^{22})NHR^{22}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$, $OCONHR^{20}R^{23}$ and $OCON(R^{20})_2$;

$R^{22}$ is selected from the group consisting of: $C_{1-15}$ alkyl, $C_{2-15}$ alkenyl, $C_{2-15}$ alkynyl, heterocyclyl, aryl and heteroaryl, said alkyl, alkenyl, and alkynyl being optionally substituted with 1–3 halo, aryl or heteroaryl groups;

$R^{23}$ is $R^{21}$ or H;

$R^{24}$ is selected from aryl, $COR^{22}$, $CO_2R^{22}$, $CON(R^{20})_2$, $R^{23}$ and $SO_2R^{22}$;

n is 1–4;

m is 1–4;

and when two $R^{20}$ groups are present, when $R^{20}$ and $R^{21}$ are present, or when $R^{20}$ and $R^{23}$ are present, said two $R^{20}$ groups, $R^{20}$ and $R^{21}$ or said $R^{20}$ and $R^{23}$ may be taken in combination with the atoms to which they are attached and any intervening atoms and represent heterocyclyl containing from 5–10 atoms, at least one atom of which is a heteroatom selected from O, or N, said hetercyclyl optionally containing 1–3 additional N atoms and 0–1 additional O or S atom.

Another subset of the compounds of the invention relates to compounds of formula I wherein:

(Ar) is selected from the group consisting of:
 a) phenyl,
 b) pyridyl,
 c) pyrimidinyl,
 d) thiophenyl,
 e) furanyl,
 f) imidazolyl,
 g) thiazolyl,
 h) isothiazolyl,
 i) oxazolyl and
 j) isoxazolyl;

(HAr)

is selected from the group consisting of:
 a) pyridyl,
 b) quinolyl,
 c) purinyl,
 d) imidazolyl and
 e) imidazopyridyl;

$R^1$ is:
 a) H or
 b) substituted alkyl;

$R^2$ is selected from the group consisting of:
 a) —$C_{1-7}$-alkyl optionally interrupted by 1 nitrogen atom and optionally substituted by: oxo or $NR^{23}$,
 b) —$C_{4-7}$-cycloalkyl optionally interrupted by 1 nitrogen atom and optionally substituted by: oxo or $NR^{23}$,
 c) —$C_{1-4}$-alkyl-aminoacyl-$C_{2-6}$-alkyl optionally interrupted by 1 nitrogen atom and optionally substituted by: oxo or $NR^{23}$,
 d) —$C_{1-4}$-alkyl-aminoacyl-$C_{4-7}$-cycloalkyl optionally interrupted by 1 nitrogen atom and optionally substituted by: oxo, $NR^{23}$ or $NR^{24}$,
 e) —$C_{1-4}$-alkyl-aminoacylamino-$C_{2-6}$-alkyl optionally interrupted by 1 nitrogen atom and optionally substituted by: oxo, $NR^{23}$ or
 f) —$C_{1-4}$-alkyl-aminoacylamino-$C_{4-7}$-cycloalkyl optionally interrupted by 1 nitrogen atom and optionally substituted by: oxo, $NR^{23}$ or $NR^{24}$; wherein the point of attachment to the pyrrole is from the left hand side of the items listed in a through f; and $R^3$ is:
 a) H,
 b) alkyl,
 c) halo, or
 d) $CO_2R^{20}$.

Still another subset of compounds of the invention relates to compounds of formula I of subset A wherein:

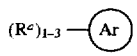

is selected from the group consisting of:
a) phenyl,
b) 4-fluorophenyl,
c) 4-chlorophenyl,
d) 3-fluorophenyl,
e) 3-chlorophenyl,
f) thiophen-2-yl,
g) thiophen-3-yl,
h) 4-fluorothiophen-2-yl,
i) 4-fluorothiophen-3-yl,
j) 5-fluorothiophen-2-yl,
k) 5-fluorothiophen-3-yl,
l) 4-chlorothiophen-2-yl,
m) 4-chlorothiophen-3-yl,
n) 5-chlorothiophen-2-yl,
o) 5-chlorothiophen-3-yl,
p) 3-methylphenyl,
q) 3,4-dichlorophenyl, and
r) 3-hydroxyphenyl;

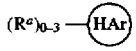

is selected from the group consisting of:
a) 4-pyridyl,
b) 4-(2-methylpyridyl),
c) 4-(2-aminopyridyl),
d) 4-(2-methoxypyridyl),
e) 4-quinolyl,
f) 4-pyrimidinyl,
g) 9-purinyl,
h) 7-(imidazo[4,5-b]pyridinyl), and
i) 4-(3-methylpyridyl);

$R^1$ is:
H;

$R^2$ is selected from the group consisting of:
a) isopropyl,
b) tert-butyl,
c) phenethyl,
d) benzyl,
e) 2-amino-2,2-dimethyletiyl,
f) 4-aminomethylbenzyl,
g) glycylaminometh yl,
h) (L)-alanylaminomethyl,
i) 2-amino-2,2-dimethylacetylaminomethyl,
j) N,N-di methylaminoethyl-N-methylaminocarbonylaminomethyl,
k) 3-piperidinecarbonylaminomethyl,
l) 4-piperidinecarbonylaminomethyl,
m) piperidin-4-yl,
n) piperidin-3-yl,
o) pyrrolidin-3-yl,
p) N-methylpiperidin -4-yl,
q) N-benzylpiperidin -4-yl,
r) N-(2-hydroxyeth-1-yl)piperidin-4-yl and
s) N-methanesulfonylpiperidin -4-yl; and $R^3$ is selected from the group consisting of:
a) H,
b) F,
c) Cl and
d) Br.

The pharmaceutically acceptable salts of the compounds of formula I include the conventional non-toxic salts or the quarternary ammonium salts of the compounds of formula I formed e.g. from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, sulfanilic, 2-acetoxybenzoic, fumaric, toluenesulfonic, methanesulfonic, ethane disulfonic, oxalic, isethionic and the like.

The pharmaceutically acceptable salts of the present invention can be synthesized from the compounds of formula I which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The compounds of the present invention may have asymmetric centers and occur as racemates, racemic mixtures, and as individual diastereomers, with all possible isomers, including optical isomers, being included in the present invention.

This invention also relates to a method of antagonizing or inhibiting the production or activity of cytokines in a mammal in need thereof which comprises administering to said mammal an effective amount of a compound of formula I to antagonize or inhibit cytokine production or activity such that it is regulated down to normal levels, or in some cases to subnormal levels, so as to ameliorate or prevent the disease state.

The compounds of formula I can be used in the manufacture of a medicament for the prophylactic or therapeutic treatment of disease states in mammals, which are exacerbated or caused by excessive or unregulated cytokines production, more specifically IL-1, IL-6, IL-8 or TNF, by such mammal's cells, such as but not limited to monocytes and/or macrophages.

Compounds of formula I inhibit cytokines, such as IL-1, IL-6, IL-8 and TNF and are therefore useful for treating inflammatory diseases, such as rheumatoid arthritis, rheumatoid spondylitis, osteoarthritis, gouty arthritis and other arthritic conditions.

The compounds of formula I may be used to treat other disease states mediated by excessive or unregulated cytokine production or activity. Such diseases include, but are not limited to sepsis, e.g., gram negative sepsis, septic shock, endotoxic shock, toxic shock syndrome, adult respiratory distress syndrome, cerebral malaria, chronic pulmonary inflammatory disease, silicosis, pulmonary sarcoidosis, bone resorption diseases, such as osteoporosis, reperfusion injury, graft vs. host reaction, allograft rejection, fever and myalgia due to infection, such as influenza, cachexia secondary to infection or malignancy, cachexi, secondary to acquired immune deficiency syndrome (AIDS), AIDS and other viral infections, ARC (AIDs related complex), keloid formation, scar tissue formation, Crohn's disease, ulcerative colitis, pyresis, such as cytomegalovirus (CMV), influenza virus and the herpes family of viruses such, as Herpes Zoster or Simplex I and II.

The compounds of formula I may also be used topically in the treatment of inflammation such as for the treatment of rheumatoid arthritis, rheumatoid spondylitis, osteoarthritis, gouty arthritis and other arthritic conditions; inflamed joints, eczema, psoriasis or other inflammatory skin conditions such as sunburn; inflammatory eye conditions including conjunctivitis; pyresis, pain and other conditions associated with inflammation.

The compounds of formula I are normally formulated as pharmaceutical compositions, which are comprised of a compound of formula I and a pharmaceutically acceptable carrier. The compounds of formula I may also be administered in combination with a second therapeutically active compound. These procedures may involve mixing, granulating and compressing or dissolving the ingredients as appropriate to the desired preparation.

The pharmaceutical carrier employed may be, for example, solid or liquid. Solid carriers include lactose, terra alba, sucrose, talc, gelatin, agar, pectin, acacia, magnesium stearate, stearic acid and the like. Liquid carriers include syrup, peanut oil, olive oil, water and the like. Similarly, the carrier may include time delay material, such as glyceryl monostearate or glyceryl distearate, alone or with a wax.

A wide variety of pharmaceutical forms can be employed. Thus, if a solid dosage form is used, the preparations typically be in the form of a tablet, hard gelatin capsule, a troche or lozenge. The amount of solid will vary widely but preferably will be from about 0.025 mg to about 1 g. When a liquid dosage form is used, the preparation is typically in the form of a syrup, emulsion, soft gelatin capsule, sterile injectable liquid or nonaqueous liquid suspension.

The compounds of formula I may also be administered topically in the form of a liquid, solid or semi-solid. Liquids include solutions, suspensions and emulsions. Solids include powders, poultices and the like. Semi-solids include creams, ointments, gels and the like.

The amount of a compound of formula I, for the methods of use disclosed herein, vary with the compound chosen, the nature and severity of the condition, and other factors. A representative, topical dose of a compound of formula I is from about 0.01 mg to about 1500 mg, administered one to four, preferably one to two times daily.

While it is possible for an active ingredient to be administered alone as the raw chemical, it is preferable to present it as a pharmaceutical formulation. The active ingredient typically comprises about 0.001% to about 90% w/w.

Drops according to the present invention may comprise sterile aqueous or oil solutions or suspensions, and may be prepared by dissolving the active ingredient in a suitable aqueous solution, optionally including a bactericidal and/or fungicidal agent and/or any other suitable preservative, and optionally including a surface active agent. The resulting solution may then be clarified by filtration, transferred to a suitable container which is then sealed and sterilized by autoclaving or maintaining at 98°–100° C. for half an hour. Alternatively, the solution may be sterilized by filtration and transferred to the container by aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous liquid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as steric or oleic acid together with an alcohol such as propylene glycol or macrogels. The formulation may incorporate any suitable surface active agent such as an anionic, cationic or non-ionic surfactant such as sorbitan esters or polyoxyethylene derivatives thereof. Suspending agents such as natural gums, cellulose derivatives or inorganic materials such as silicas, and other ingredients such as lanolin may also be included.

The methods of the instant invention may also be carried out by delivering the agent parenterally. The term 'parenteral' as used herein includes intravenous, intramuscular, or intradermal and subcutaneous administration. The intravenous and intramuscular forms of administration are preferred. Appropriate dosage forms for such administration may be prepared as described above. The instant invention can also be carried out by delivering the compounds of formula I intranasally, rectally, transdermally or vaginally.

The compounds of formula I may be administered by inhalation. By 'inhalation' is meant intranasal, pulmonary or oral inhalation administration. Appropriate dosage forms for such administration include an aerosol formulations, e.g., metered dose inhalers and the like.

Compounds of formula I (e.g., compound 22 and 22a) are prepared (see Scheme I) by the reaction of compound 1, or a protected version thereof with an acetophenone (commercially available) in the presence of potassium cyanide followed by treatment with an alkyl or aryl amine, ammonia or equivalent thereof (ammonium acetate) at elevated temperature.

SCHEME I
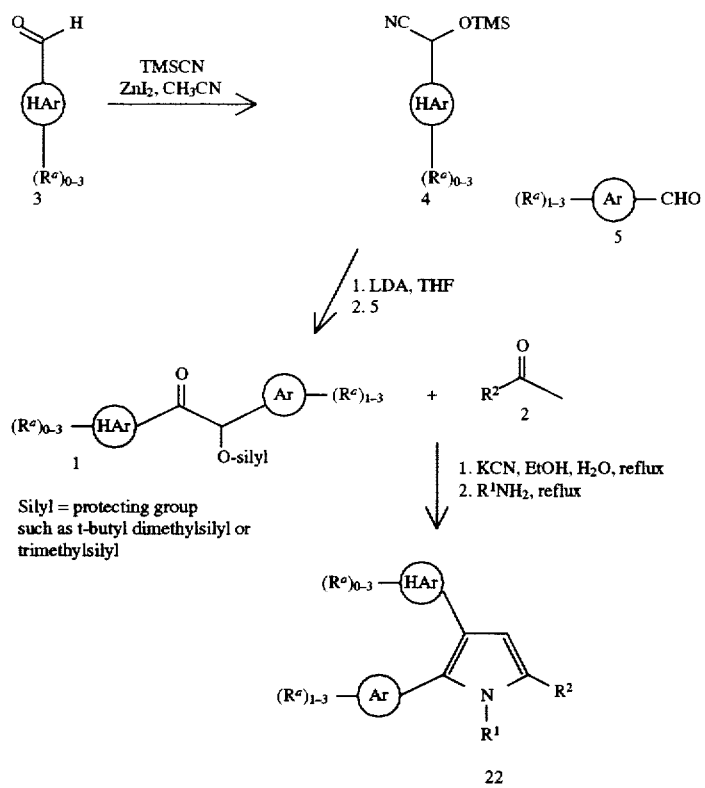
Compound 1 is prepared as described below. Heteroaromatic aldehydes 3 are converted to their trimethylsilyl cyanohydrins 4. Deprotonation and reaction with an aldehyde 5 provides trimethyl silyl protected benzoins 1 (Hunig. S.; Wehner. G. Chem. Ber. 112, 2062 1979).
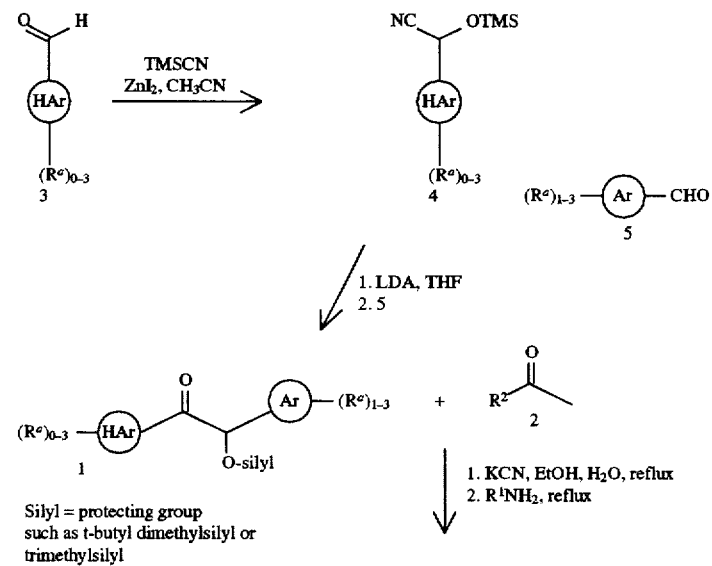

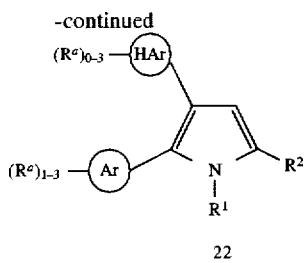

22

SCHEME II

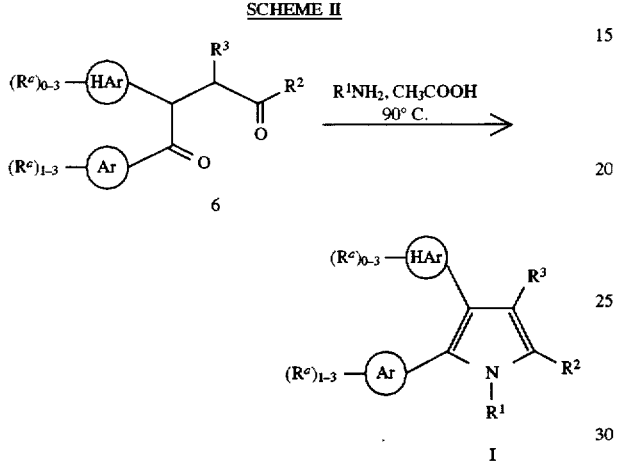

The condensation of a 1,4-diketone with ammonia gives rise to pyrroles (Paal Knor Synthesis). A 1,4-diketone such as 6 is reacted with ammonia (or a compound that gives rise to ammonia such as ammonium acetate) or a primary amine to provide compounds of formula 1 generally in the presence of an acid catalyst such as acetic acid or titanium tetrachloride (See Scheme II). 1,4-diketone 6 is thus regioselectively constructed so that the appropriate groups are present on the pyrrole ring.

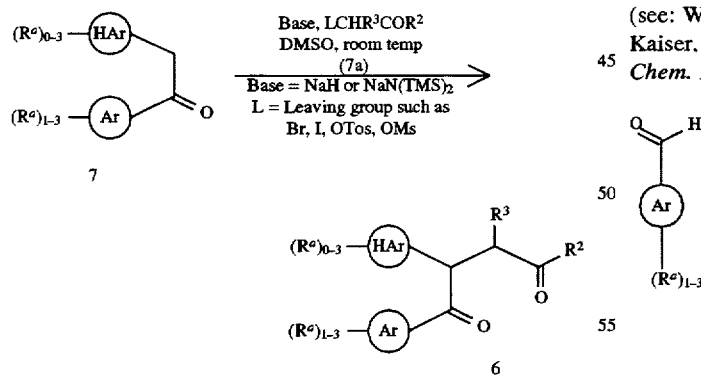

Alkylation of 1-aryl-2-heteroarylethanones 7 with an alpha-leaving group substituted ketone 7a provides 1,4 diketones 6 (Iyer, R. N.; Gopalachari, R. Ind. J. Chem. 11, 1260, (1973)). The alkylating agent 7a is prepared by various methods such as: free radical or acid catalyzed bromination of a ketone; halogenation of a ketone enolate; conversion of the hydroxyl group of an alpha-hydroxy ketone to a leaving group such as the bromide, triflate, tosylate or mesylate.

Ethanones 7 are prepared by addition of heteroaryl methyl anions 8 to activated benzoic acids 9 (for example esters, acid chlorides, nitrites and N-methoxy-N-methyl amides) (see: Wolfe, J. F. et al *J. Org. Chem.* 39, 2006 (1974) and Kaiser, E. M. et al *Synthesis* 705 (1975) and Ohsawa A. *Chem. Pharm. Bull.* 26, 3633, (1978)).

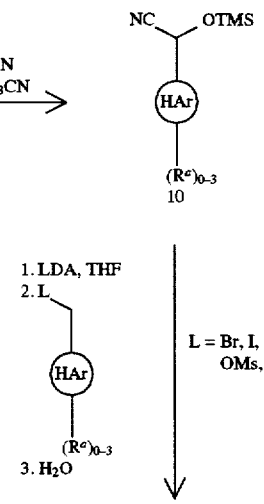

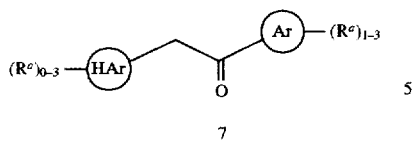

An alternative approach to Compound 7 is via alkylation of aryl trimethyl silyl protected cyanohydrins 10. Treatment of 10 with lithium diisopropyl amide in THF and addition of a heteroaryl methyl group functionalized with a leaving group L (for example: Br, I, Cl, tosylate, mesylate) followed by acid catalyzed hydrolysis of the silyl cyanohydrin group provides ethanone 7 (Deuchert, K.; Hertenstein, U.; Hunig, S.; Wehner, G. Chem. Ber. 112, 2045, (1979)).

SCHEME III

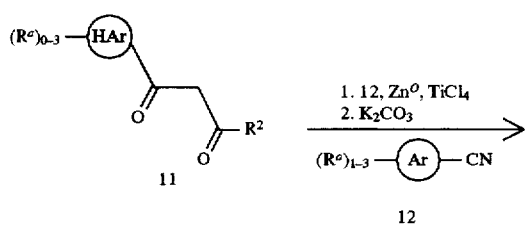

SCHEME III -continued

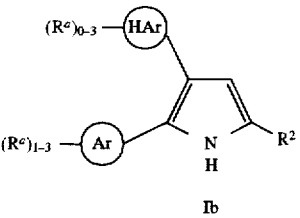

The reductive cross coupling of a 1,3 diketone 11 with a nitrile 12 in the presence of zinc and titanium tetrachloride gives rise to compounds of formula I (Gao, J. Hu, M.; Chen, J.; Yuan, S.; Chen, W. Tet Lett. 34, 1617, (1993)). The 1,3 diketone 11 is prepared by alkylation of 4 with bromoacetophenones (See Scheme III).

SCHEME IV

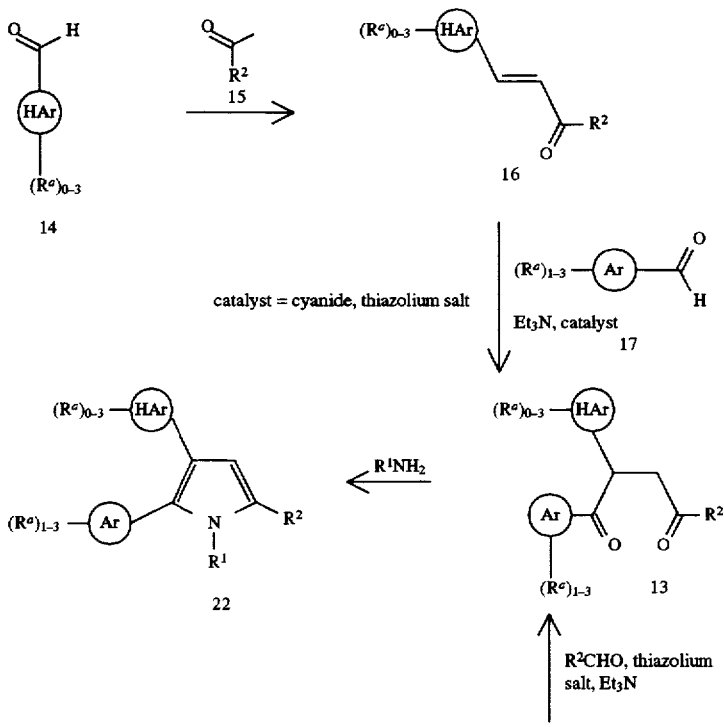

-continued
SCHEME IV

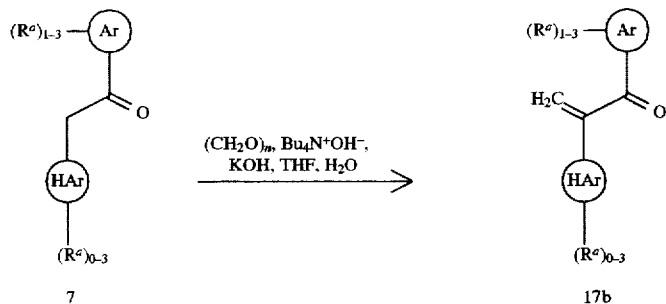

The 1,4-diketone 13 can also be prepared as described below in Scheme IV. A heteroaryl aldehyde 14 is condensed with a methyl ketone 15 to provide α,β-unsaturated ketone 16. In the presence of a catalyst such as cyanide or a thiazolium salt, the aryl aldehyde 17 reacts with 16 to give 13 (Stetter, H. J. et al Heterocyclic Chem. 14, 573, 1977 and Stetter, H. et. al. Organic Reactions, Vol 40, 407–496). Condensation of 13 with an amine provides compounds of formula I.

Alternatively, variations of $R^2$ may be introduced by addition of $R^2$ aldehydes to alkenes 17b that are readily available from the ketones 7 described above.

SCHEME V

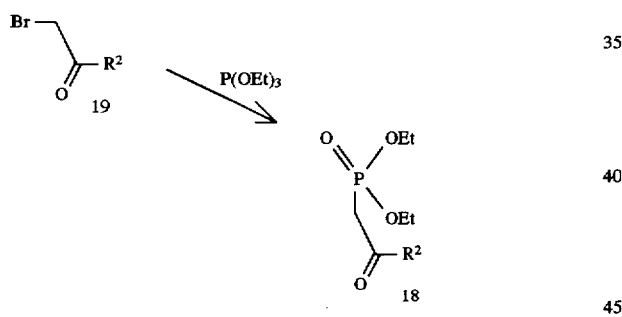

-continued
SCHEME V

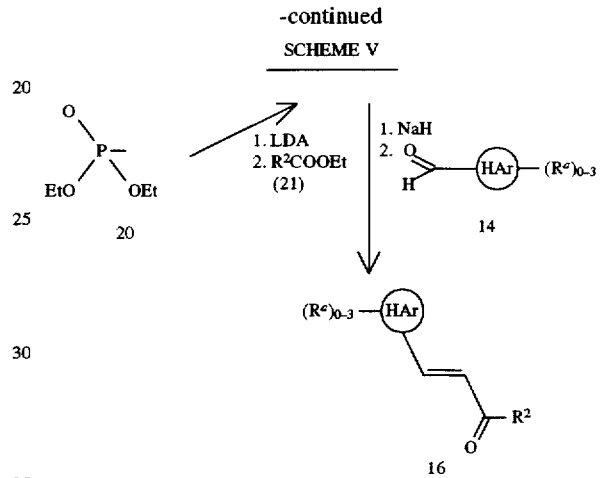

Intermediate 16 is prepared by a Horner-Emmons reaction of the anion of 18 with the heteroaryl aldehyde 14. The reagent 18 is prepared by reaction of the bromoketone 19 and triethyl phosphite or by reaction of the lithium salt of diethyl methylphosphonate with an ester 21.

SCHEME VI

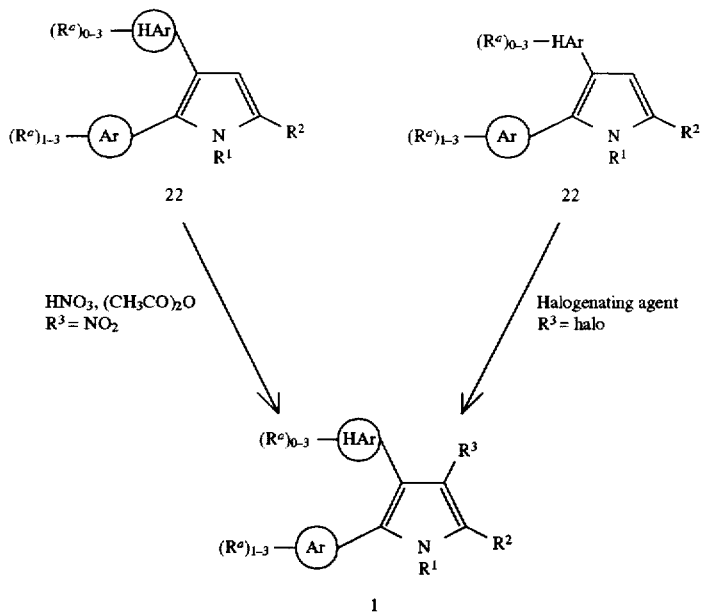

A nitro group is introduced into the pyrrole nucleus at the $R^3$ position (generic nomenclature) by electrophilic nitration of a compound such as 22 (or a less advanced intermediate) in the presence of fuming nitric acid and acetic anhydride.

Halogens may be introduced by electrophilic halogation with reagents such as $XeF_2$ ($R_3$=F), N-chlorosuccinimide in DMF ($R^3$=Cl), N-bromosuccinimide in DMF ($R^3$=Br), $I_2$ in KI ($R^3$=I). Other reagents are available to carry out this conversion, the choice of reagent being dependent on the presence of functional groups that may be sensitive to the reagent being utilized. See, e.g. Pyrroles Part 1, R. Alan Jones, ed., *Heterocyclic Compounds*, Vol 48 Part 1, John Wiley, New York, 1990. Pages 348–391.

Introduction of alkyl and heterocyclyl alkyl groups at the 3 position is described. Direct introduction is possible as described in the use of 1,4 diketone 6 as a precursor of compounds of formula Ia as described above. The preparation of the pyrrole 23 containing a hydroxymethyl group at position provides an intermediate that is readily elaborated into compounds of formula I.

Acylation of the hydroxyl group with activated acids an isocyanates provides esters and carbamates respectively of formula I. Conversion of the hydroxy group into a leaving group 24 (for example Br, I, Cl, triflate etc.) enables the introduction of alkyl, heterocyclyl and amines and thiol groups by displacement with a nucleophile. Suitable nucleo-

SCHEME VII

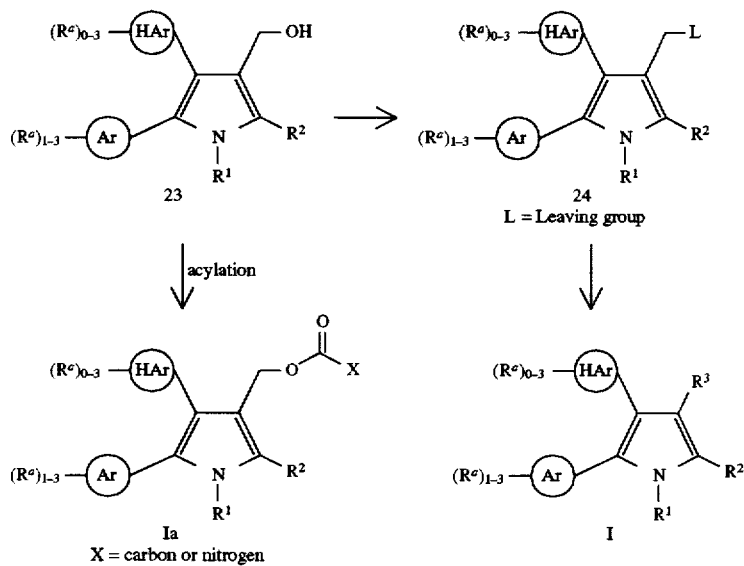

philes include, for example, an alkyl or heterocyclyl anion, a primary or secondary amine or a thiol.

1890). Alternatively a 2-amino ketone 28 reacts with a 3-keto ester 27 to produce 25.

SCHEME VIII

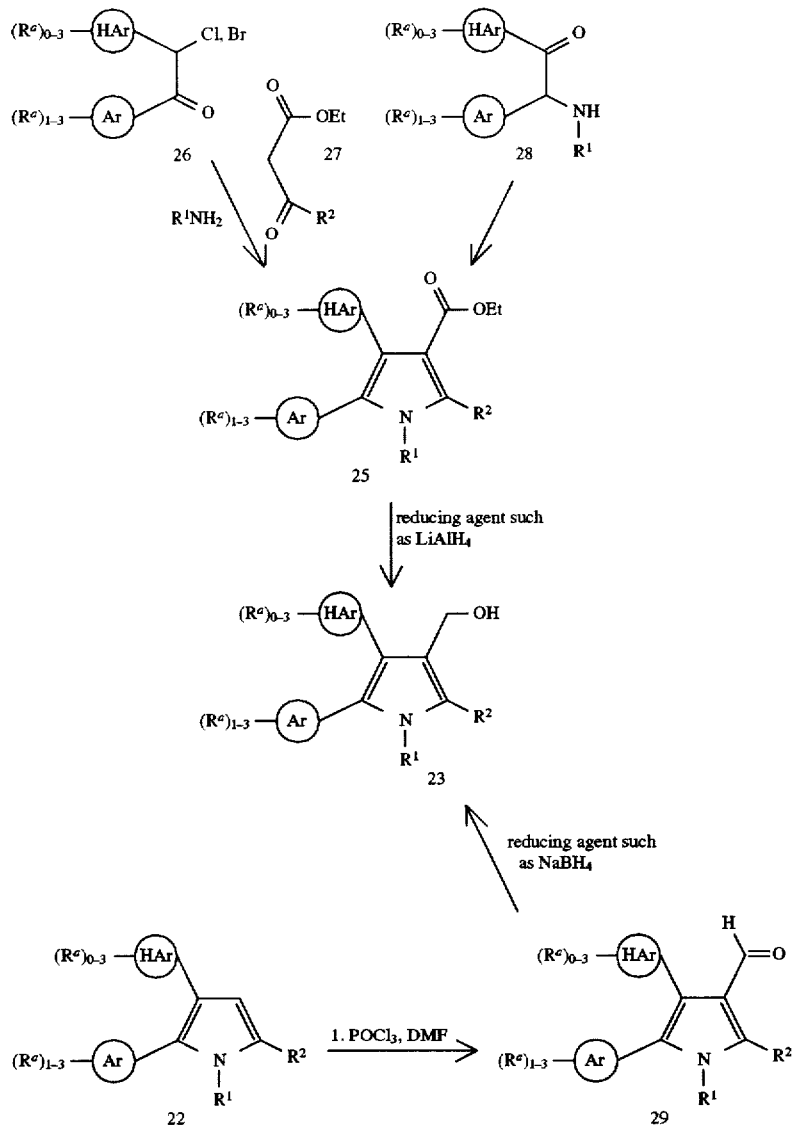

Hydroxymethyl substituted pyrroles 23 are prepared by reduction of esters 25 through the reaction with a reducing agent such as lithium aluminum hydride. The ester 25 are prepared by treatment of 1,2 -disubstituted-2 halo ketones 26 with 3-keto esters 27 and ammonia or an amine producing ester 25 (Hantzsch. Ber. Dtsch. Chem. Ges. 23, 1474, A further method of synthesis of 23 is the reduction of the aldehyde 29 with a reducing agent such as sodium borohydride. The aldehyde is prepared by treatment of the $R^3$-unsubstituted pyrrole with the Villsmeyer reagent ($POCl_3$/DMF).

SCHEME IX

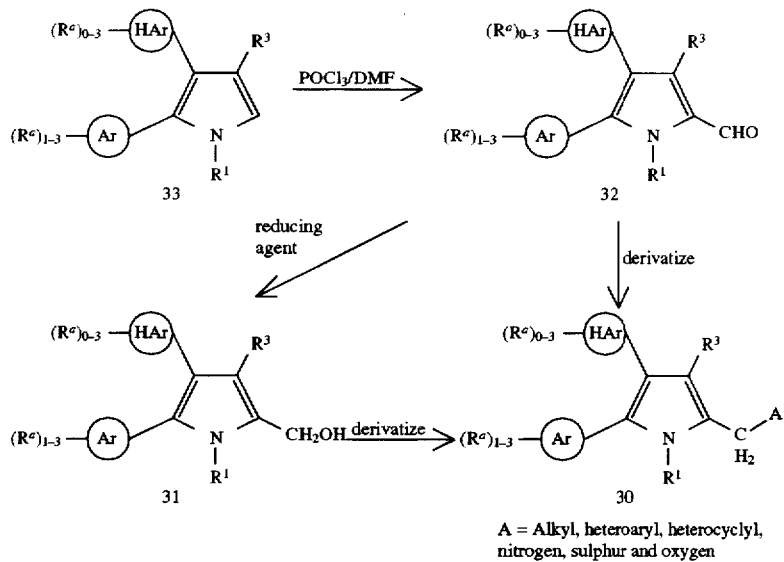

A = Alkyl, heteroaryl, heterocyclyl, nitrogen, sulphur and oxygen

Variation of $R^2$ groups may be achieved as shown in Scheme IX. Alkyl, heteroaryl, heterocyclyl and heteroatom and heteroatom substituted alkyl, heteroaryl, heterocyclyl groups are introduced through the displacement of a leaving group derived from the hydroxyl group in 31. The allylic nature of a leaving group (such as bromide, chloride, mesylate, tosylate and triflate etc.) at this position make it very prone to displacement by amines; thiols; alkoxides; aryl, alkyl, heteroaryl and heterocyclyl anions. Furthermore this type of functional group is utilized in organometallic coupling reactions. The alcohol is prepared from the aldehyde 32 by reduction with a reducing agent such as sodium borohydride. The aldehyde 32 is converted to 30 reductive alkylation (A=amino). The aldehyde 32 is reacted with alkyl, aryl, heteroaryl and heterocyclyl anions to give secondary alcohols. These are dehydrated and reduced to give further analogs of formula I. Aldehydes 32 are available by hydrolysis of acetals that have been introduced in one of the schemes above or via reaction of the unsubstituted pyrrole 33 with Villsmeyer reagent (DMF/POCl$_3$).

SCHEME X

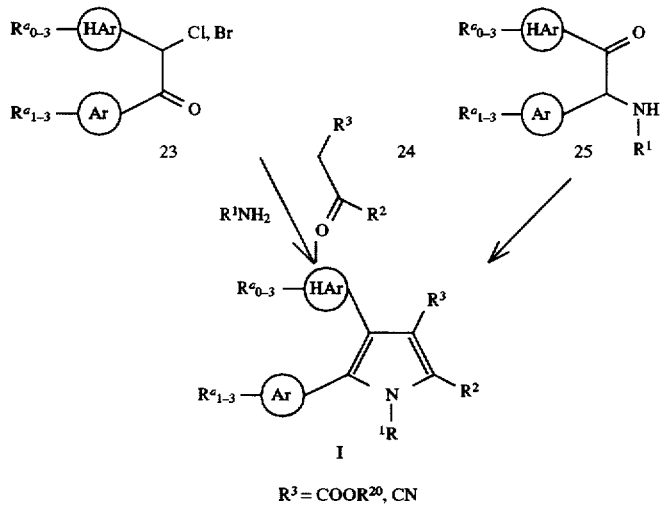

$R^3 = COOR^{20}, CN$

The ester and nitrile of formula I may be prepared as shown in Scheme X by treatment of 1,2 disubstituted-2 halo ketones 23 with 24 with ammonia or an amine producing ester I (Hantzsch. Ber. Dtsch. Chem. Ges. 23, 1474, 1890). Alternatively a 2-amino ketone 25 reacts with 24 to produce I.

SCHEME XI
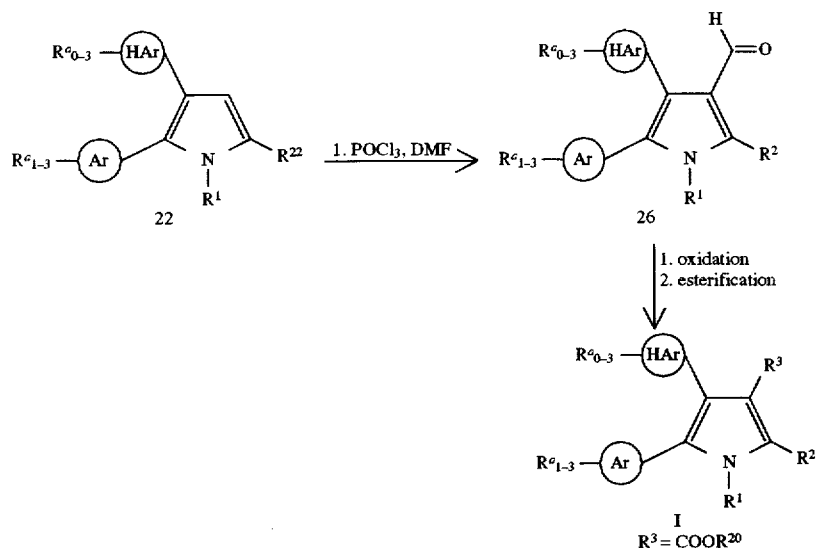
A further method of synthesis of Compounds of formula I is by oxidation and esterification of aldehyde 26. The aldehyde is prepared by treatment of the $R^3$-unsubstituted pyrrole 22 with the Villsmeyer reagent ($POCl_3$/DMF). See Scheme XI.
SCHEME XII
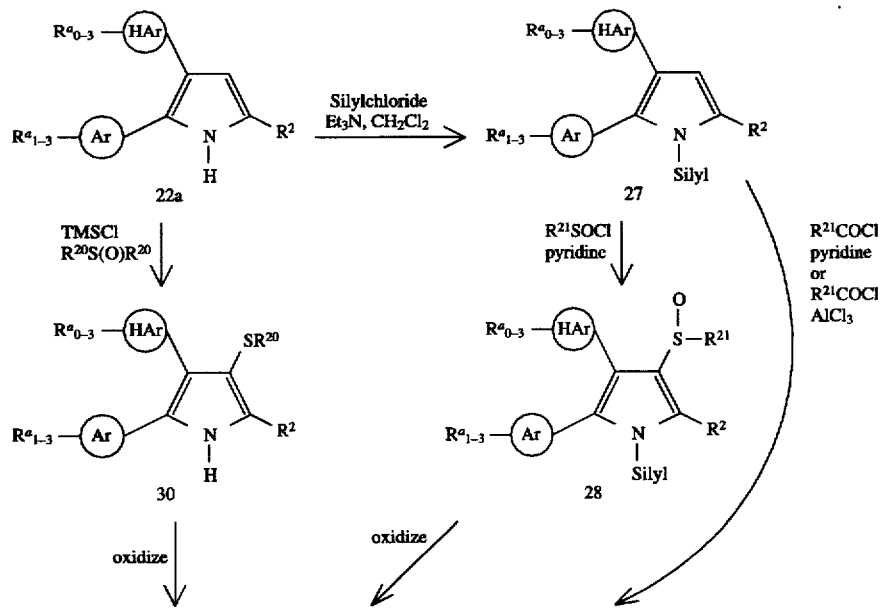

SCHEME XII -continued

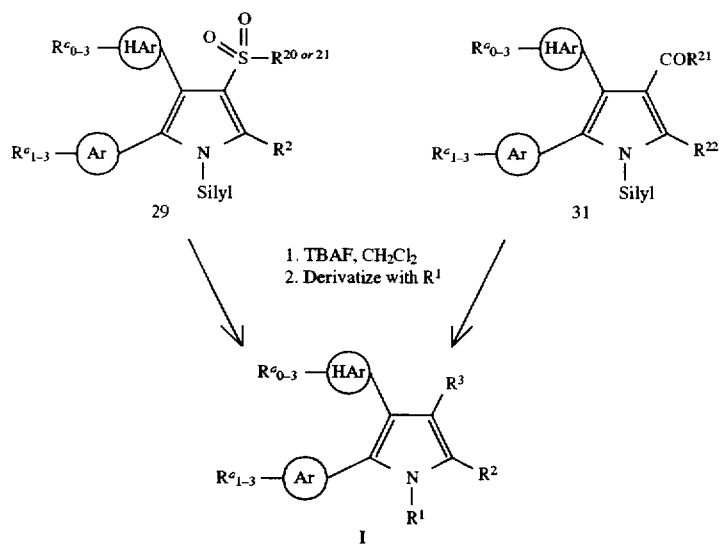

The pyrrole 22a may be silylated on nitrogen to give 27 by treatment with a silyl chloride and base in a solvent such as methylene chloride. The pyrrole 27 may then be sulphinylated with a sulphinylchloride under basic conditions to provide 28 (J. Org Chem 6317, 1990). Oxidation of 28 with a reagent such as m-chloroperoxybenzoic acid or potassium persulfate will give the sulphone 29. Removal of the silyl group and derivatization of the pyrrole will give compounds of Formula I. 22a may also be converted to the sulphide 30 by reaction of 22 with a symmetrical sulfoxide in the presence of trimethylsilylchloride to give 30. Oxidation of 30 with a reagent such as m-chloroperoxybenzoic acid will give 29. The silyl pyrrole 27 may also be acylated with an acid chloride to give the ketone 31. Removal of the silyl group from 31 and derivatization of the pyrrole will give compounds of Formula I. Pyrroles such as 22 may also be sulphinylated directly without N-protection, by treatment with sulphinyl chlorides in a solvent such as dichloromethane at 0° C. (J. Org. Chem. 5336, 1980). Oxidation as described above may provide pyrroles of Formula I where $R^3$ is $SO_2R^{21}$. See Scheme XII.

SCHEME XIII

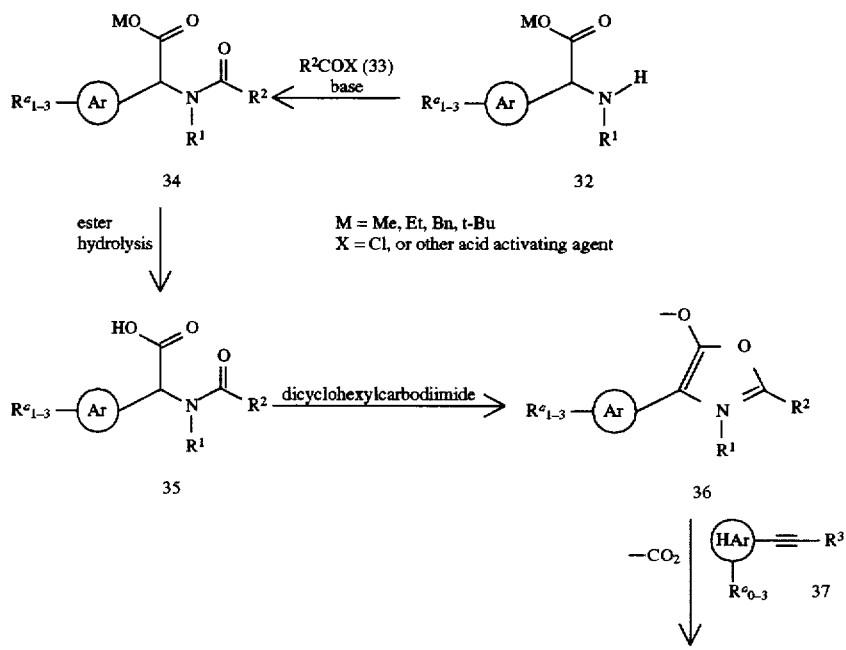

SCHEME XIII -continued

Note: R¹ may also be a protecting group that may be removed in the final step to give compounds where R¹ is H.

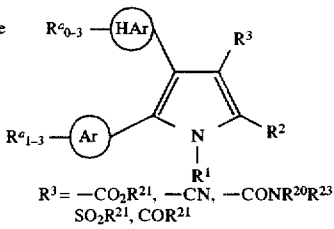

$R^3 = -CO_2R^{21}, -CN, -CONR^{20}R^{23}$
$SO_2R^{21}, COR^{21}$

I

The amino acid ester 32 may be acylated with an acid 33 that is suitably activated (acid chloride or other activating group used in amide coupling reactions) to give 34. Hydrolysis of the ester protecting group will provide 35. Cyclization by treatment with an acid activating group such as DCC will give the oxazolium species 36. Addition of an alkyne 37 to 36 may give a pyrrole of Formula I via a 3+2 cycloaddition followed by loss of carbon dioxide. Various $R^3$ groups may be incorporated in this manner. See Scheme XIII.

pattern. Lithium anions are prepared by metalation of a regioselectively halogenated pyrrole, or the regioselective deprotonation of the pyrrole preferably by the use of a directing functional group. The resulting anion may then be trapped by a trialkyl stannyl halide or a trialkyl borate or transmetalated to magnesium or zinc by treatment with appropriate halide salts. A further method used to incorporate a trialkyl stannyl group is the coupling of a bromo, iodo or triflate substituted pyrrole with hexaalkylditin in the presence of a palladium catalyst.

SCHEME XIV

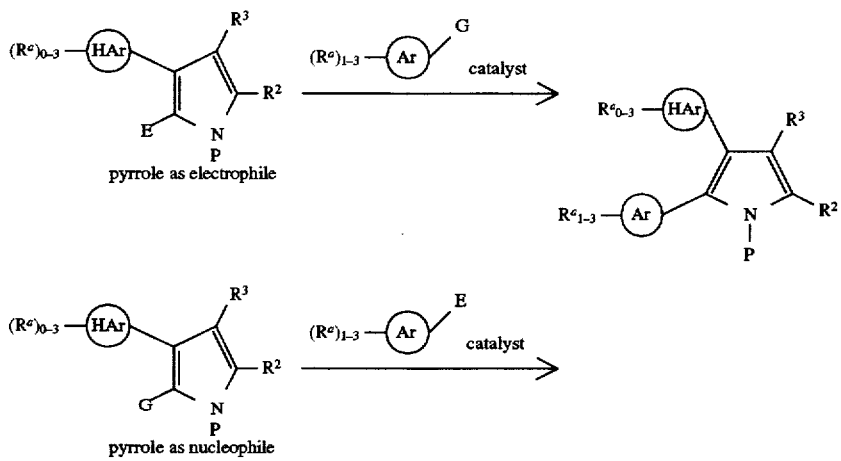

Aryl and heteroaryl rings are appended to the pyrrole ring system by utilization of organometallic coupling technology (Kalinin, V. Synthesis 413 1991). Two alternative approaches are utilized for appending aryl and heteroaryl rings to the pyrrole ring. The pyrrole ring functions as the electrophile or as the nucleophile.

Any of the two appended aromatic or heteroaromatic rings is attached to the pyrrole ring system. (Alvarez, A. J. et al J. Org. Chem. 1653, (1992) (use of boronic acid and tributyl stannanes for coupling to aromatic and heteroaromatic rings)). Attachment of pyrrole pendant groups is carried out with or without other Ar, HAr, $R^2$ or $R^3$ groups attached. $R^2$ groups are introduced through the use of the Heck reaction (Heck, R. F. Org. React. (1982), 27, 345) in which alkenes are coupled with heteroaryl halides. Alkynes are coupled with heteroaryl halides to give alkyne substituents at $R^2$. These $R^2$=alkene and alkyne groups may, in turn be reduced to alkanes by hydrogenation.

The synthesis of pyrroles containing nucleopilic groups for coupling reactions depends on the pyrrole substitution The synthesis of pyrroles incorporating electrophilic groups may be carried out by the regioselective halogenation of a pyrrole (Pyrroles Part 1, R. Alan Jones,ed., Heterocyclic Compounds, Vol 48 Part 1, John Wiley, New York, 349–391, (1990)). The regioselectivity of halogenation will depend on the size, nature and substitution position on the pyrrole ring as well as the presence or absence of the N-alkyl protecting group. Triflates may be prepared by acylation of hydroxy pyrroles with triflic anhydride.

The reaction conditions used will depend on the nature of the coupling species. In the case of magnesium, zinc and stannyl coupling reactions the solvent used is normally toluene or DMF under anhydrous conditions. In the case of boronic acid couplings, a heterogenous system is used of water, toluene, dimethoxyethane or ethanol in the presence of a base such as sodium carbonate or bicarbonate. In general the reaction takes place at an elevated temperature (80°–100° C.). Catalysts used depend on the structure of the components to be coupled as well as the functional groups.

Most commonly, tetrakistriphenylphosphinepalladium (0) or palladium bis triphenyl phosphine dichloride are utilized.

The preparation of 4-halo substituted pyrroles may be accomplished by treatment of 2,3,5, trisubstituted pyrroles with halogens. Alkyl substituents at the 4 position of the pyrrole may be introduced through the synthesis of the 1,2,3,4-tetrasubstituted 1,4-diketone followed by cyclization with ammonia or an amine. Alternatively, coupling of alkenes or alkynes with 4-halo pyrroles (Heck reaction, see Kalinin, V. Synthesis 413 (1991) for a review) will give rise to alkenyl and alkynyl substituted pyrroles that may be reduced or otherwise modified to provide compounds of formula I.

Functional groups such as halogens, sulfides, nitro groups, ethers and other groups stable to the reaction conditions used in the linear synthesis of the pyrroles are incorporated in the initial steps of the reaction sequence. Sulfides may be oxidized to sulfoxides and sulfones with reagents such as m-chloroperbenzoic acid. Sulfides may also be converted to sulfonyl chlorides by oxidation and chlorination by chlorine in water.

Primary amines are prepared from nitro groups by catalytic (Pd/C, $H_2$ or Raney Nickel, $H_2$) or chemical means ($CoCl_2$, $NaBH_4$). Alkylation of amines to give secondary and tertiary amines is achieved by reductive alkylation (aldehyde, $NaCNBH_4$) or alkylation with an alkyl group substituted with a leaving group in the presence of a base such as $K_2CO_3$. Tertiary amines may, alternatively, be carried through the reaction sequence to the pyrroles. Acylation of primary or secondary amines with activated acids, chloroformates, isocyanates and chlorosulfonates will give rise to amides, carbamates, ureas and sulfonamides, respectively.

Other methods of preparing amides and ureas are useful; such as for example, treatment of the amine with phosgene, or an equivalent thereof, followed by acylation of an alcohol or amine with the intermediate activated chloroformamide.

Carboxylic acids are best introduced as esters early in the synthesis. Saponification will provide carboxylic acids. Transesterification or esterification of the acids will give esters. Carboxylic acids may be converted to amides by activation and reaction with amines. Phenols are best introduced in a protected form early in the synthetic sequence to the pyrrole. Removal of the protecting group provides a phenol which may subsequently be alkylated in the presence of an alkylating agent and base to give an ether, or acylated with an isocyanate to give carbamates. Phenols may be converted to aryl ethers by reaction with an aryl bismuthane in the presence of copper II acetate.

Aryl and heteroaryl groups may be attached to pyrrole pendant aryl and heteroaryl groups by application of coupling chemistry technology as outlined above.

All of the above secondary conversions are well known to one skilled in the art. The sequence and conditions of the reaction steps is dependent on the structure and functional groups present. Protecting groups may be necessary and may be chosen with reference to Greene, T. W., et al., *Protective Groups in Organic Synthesis*, John Wiley & Sons, Inc., 1991. The blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with fluoride ion, treatment with a transition metal catalyst and a nucleophile, and catalytic hydrogenation.

Examples of suitable hydroxyl protecting groups are: trimethylsilyl, triethylsilyl, o-nitrobenzyloxycarbonyl, p-nitrobenzyloxycarbonyl, t-butyldiphenylsilyl, t-butyldimethylsilyl, benzyloxycarbonyl, t-butyloxycarbonyl, 2,2,2-trichloroethyloxycarbonyl, and allyloxycarbonyl. Examples of suitable carboxyl protecting groups are benzhydryl, o-nitrobenzyl, p-nitrobenzyl, 2-naphthylmethyl, allyl, 2-chloroallyl, benzyl, 2,2,2-trichloroethyl, trimethylsilyl, t-butyldimethylsilyl, t-butldiphenylsilyl, 2-(trimethylsilyl)ethyl, phenacyl, p-methoxybenzyl, acetonyl, p-methoxyphenyl, 4-pyridylmethyl and t-butyl.

The following examples are illustrative and are not limiting of the compounds of this invention.

EXAMPLE 1

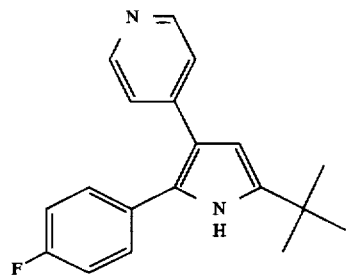

2-(4-fluorophenyl)-5-(t-butyl)-3-(4-pyridyl)-pyrrole

Step 1

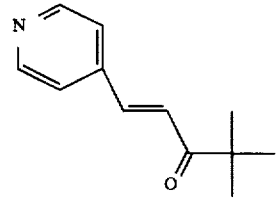

To a solution of 10 g (0.25 m) of sodium hydroxide in 150 ml of ethanol was added a mixture of 5 g (0.05 m) pinacolone and 5.35 g (0.05 m) of 4-pyridaldehyde in 10 ml of ethanol. After 3 hours the reaction mixture was diluted with 300 mL of EtOAc and 100 ml of water. The phases were separated and the organic phase was washed with water (2×100 ml) and brine (100 ml) and dried over $MgSO_4$. The mixture was filtered and the filtrate was dried in vacuo. The product was purified by crystallization from ethanol and water.

$H^1$-NMR ($CDCl_3$, 300 MHz): 1.22 (s, 9H); 7.26 (d, 1H); 7.41 (m, 2H); 7.56 (d, 1H); 8.74 (m, 1H).

Step 2

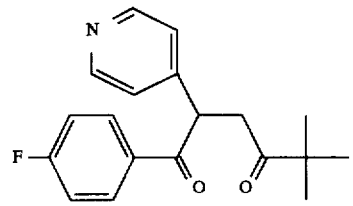

A mixture of 0.15 g (0.79 mmol) of the product of Step 1, above, 0.098 g ( 0.79 mmol) of 4-fluorobenzaldehyde, 20 mg of 3,4-dimethyl-5-(2-hydroxyethyl)-thiazolium iodide and 0.05 g (0.39 mmol) of triethylamine was heated to 80° C. for 3 hours. The reaction mixture was diluted with water and extracted with EtOAc. The combined organic extracts were washed with brine and dried over MgSO₄. The mixture was filtered and the filtrate was concentrated in vacuo. The product was purified by medium pressure liquid chromatography over silica gel to give the product.

H¹-NMR (CDCl₃, 300 MHz): 1.17 (s, 9H); 2.82 (dd, 1H); 3.67 (dd, 1H); 5.04 (dd, 1H); 7.06 (t, 2H); 7.19 (d, 2H); 7.97 (dd, 2H); 8.50 (d, 2H).

Step 3

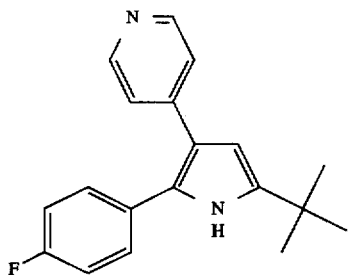

The product of Step 2 was dissolved in 1.0 mL of acetic acid (AcOH) and was treated with 0.5 g of ammonium acetate. The reaction mixture was heated to 110° C. for 1 hour. The reaction mixture was cooled to room temperature and diluted with 25 mL of ethyl acetate and was washed with 3×10 mL of water and 1×10 mL of brine. The organic phase was dried over MgSO₄, filtered and concentrated in vacuo. The residue was purified by rotary chromatography over silica gel eluting with 2% MeOH/CH₂Cl₂.

H¹-NMR (CDCl₃, 300 MHz): 1.35 (2, 9H); 6.19 (d, 1H); 7.05 (t, 2H); 7.20, m, 2H); 7.25–7.36 (m, 2H); 8.03, bs, 1H); 8.41 (d, 2H).

EXAMPLE 2

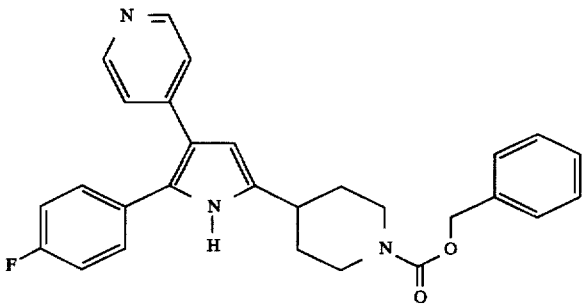

2-(4-fluorophenyl)-5-(n-(CBz)-piperidin-4-yl)-3-(4-pyridyl)-pyrrole

Step 1
1-(4-fluorophenyl)-2-(4-pyridyl)-ethanone

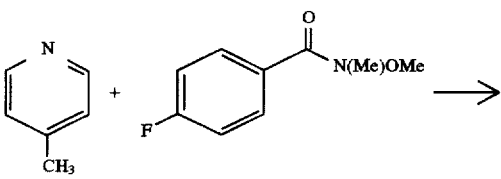

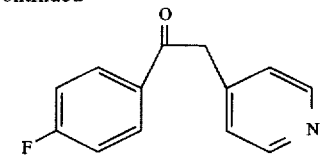

To a solution of lithium diisopropyl amide (Aldrich Chemical Co. 2.0M in heptane, THF ethyl benzene) 3.1 mL (6.3 mmol) in 6 mL of anhydrous THF at −78° C. under nitrogen was added 0.5 g (5.3 mmol) of 4-picoline dropwise. The reaction mixture was stirred for 20 minutes and then treated with a solution of 0.9 g (5.3 mmol) of 4-fluoro-(N-methyl-N-methoxy)-benzamide in THF. The reaction mixture was warmed to 0° C. and quenched by addition of 10 mL of brine. The mixture was extracted with ethyl acetate (3×10 mL) and the combined organic phases were dried over MgSO₄. The mixture was filtered and the filtrate was concentrated in vacuo to give the title compound as an orange solid.

H¹ NMR (CDCl₃ 300 MHz): 4.23 s (d, 2H), 7.1–7.18 m (4H), 8.02 (dd, 2H), 8.55 (dd, 2H).

Step 2

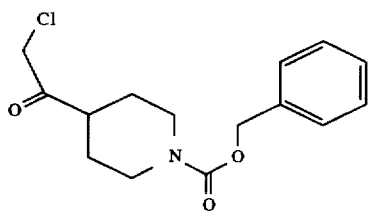

To a solution of N-carboxybenzyl-piperidine-4 carboxylic acid (2.0 g (7.6 mmol)) in 15 ml of dry toluene at room temperature was added 2 drops of DMF followed by the dropwise addition of 1.05 g of oxalyl chloride. The reaction mixture was stirred overnight at room temperature. Vacuum was applied to draw off excess HCl and oxalyl chloride and the solution was concentrated in vacuo to provide the acid chloride. The material was dissolved in 20 ml of ether and was cooled to 0° C. in a dry Erlenmeyer flask. The solution was treated with an ethereal solution of diazomethane prepared from 5 g of N-nitrosomethylurea. The solution was stirred for 20 minutes and was then treated with 8 ml of a 1M solution of HCl in ether. The reaction mixture was stirred for 30 minutes and was then diluted with 20 ml of ethyl acetate and 10 ml of a saturated solution of NaHCO₃. The phases were seperated and the organic phase was washed with water and brine and was dried over MgSO₄. The mixture was filtered and the filtrate was concentrated in vacuo to give the desired product.

H¹-NMR (CDCl₃, 300 MHz): 1.56 (m, 2H); 1.85 (bm, 2H); 2.87 (m, 3H); 4.12 (s, 2H); 4.20 (bs, 1H); 5.12 (bs, 2H); 7.35 (m, 5H).

Step 3

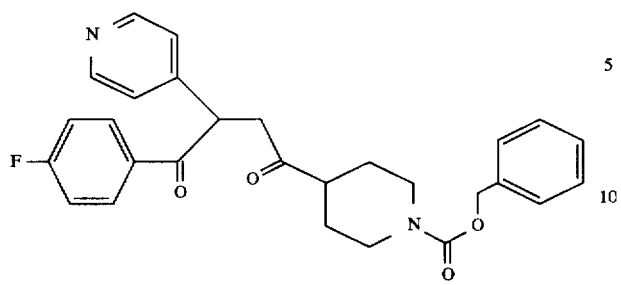

To a solution of the product of Step 1 (0.5 g (2.3 mmol)) in 5.0 ml of dry DMSO was added 2.4 ml (2.4 mmol) of a 1M solution of sodium hexamethyldisilazide in THF. After 10 minutes, a solution of 0.72 g (2.4 mmol) of the product of Step 2 was added in 1 ml DMSO dropwise. The reaction mixture was stirred for 2 hours, diluted with EtOAc (20 ml) and washed with water (3×10 ml). The combined organic phases were washed with brine and dried over $MgSO_4$. The mixture was filtered and the filtrate was concentrated in vacuo. The residue was purified by MPLC over silica gel eluting with 2% $MeOH/CH_2Cl_2$ to give the desired product.

FAB ms: C28H27N2O4F: 474; Observed: 475 (M$^+$+1).

Step 4

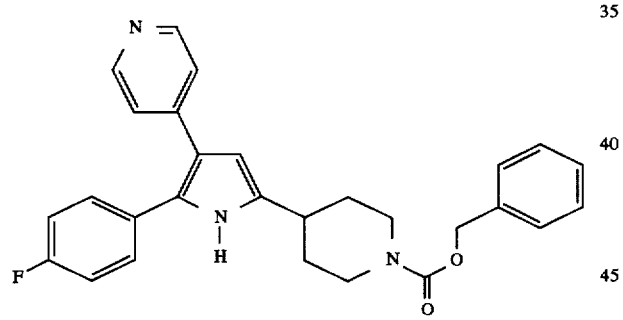

The product of Step 3 was heated in 5 ml of acetic acid in the presence of 2.0 g ammonium acetate at 110° C. for 1.5 hours. The reaction mixture was diluted with EtOAc (10 mL) and washed with water. The combined organic phases were washed with brine and dried over $MgSO_4$. The mixture was filtered and the filtrate was concentrated in vacuo. The residue was purified by MPLC over silica gel eluting with 2% $MeOH/CH_2Cl_2$ to give the desired product.

H$^1$-NMR (CDCl$_3$, 300 MHz): 1.67 (m, 2H); 2.02 (bd, 2h); 2.75–3.0 (m, 3H); 4.29 bd, 2H); 5.12 (s, 2H); 6.19 (d, 1H); 7.03 (t, 2H); 7.18 (dd, 2H); 7.25–7.39 (m, 6H); 8.39 (dd, 2H); 8.52 (bs, 1H). FAB ms: C28H26N3O2F:455; Observed: 456 (M$^+$+1).

EXAMPLE 3

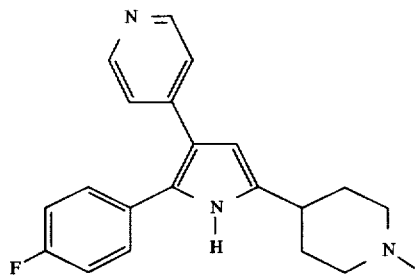

2-(4-fluorophenyl)-5-(N-methylpiperidin-4-yl)-3-(4-pyridyl)-pyrrole

To a solution of the product of Example 2 (0.032 g (0.07 mmol) in 1 ml of dry THF at room temperature was added 0.14 ml (0.14 mmol) of a 1M solution of lithium aluminum hydride in THF. The reaction mixture was heated at reflux for 2 hours. 3 ml of water was added cautiously and the mixture was extracted with ethyl acetate (3×4 ml). The combined organic extracts were dried over $MgSO_4$, filtered and concentrated in vacuo.

H$^1$-NMR (CDCl$_3$, 300 MHz): 1.81 (m, 2H); 1.95–2.12 (m, 4H); 2.30 (s, 3H); 2.59 (m, 1H); 2.95 (bd, 2H); 6.19 (d, 1H); 7.04 (t, 2H); 7.18 (dd, 2H); 7.27–7.38 (m, 4H); 8.39 (dd, 2H). FAB ms: C$_{21}$H$_{22}$N$_3$F:335; Observed: 336 (M$^+$+1).

EXAMPLE 4

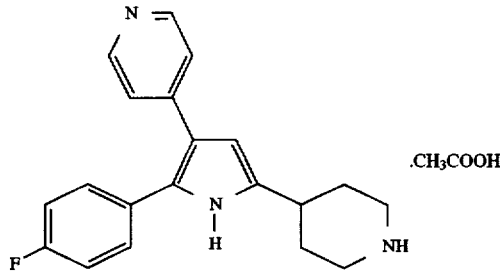

2-(4-fluorophenyl)-5-(piperidin-4-yl)-3-(4-pyridyl)-pyrrole 183 mg of the product of Example 2 was dissolved in 5 ml of acetic acid. The solution was hydrogenated over 25 hours at atmospheric pressure in the presence of 10 mg of 10% Pd/C. The mixture was filtered and the filtrate was concentrated in vacuo to give the product.

FAB ms: C$_{20}$H$_{20}$N$_3$F: 321; Observed: 322 (M$^+$+1).

EXAMPLE 5

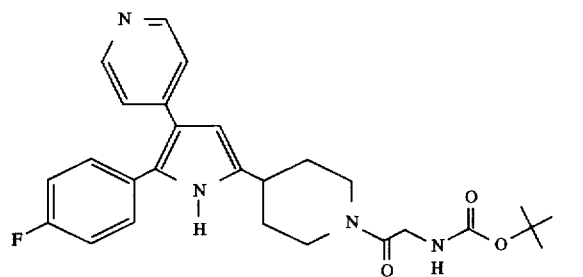

2-(4-fluorophenyl)-5-(N-(COCH$_2$NHCO$_2$-t-butyl)-piperidin-4-yl)-3-(4-pyridyl)-pyrrole To a solution of 35 mg (0.086 mmol) of the product of Example 4 in 5 ml of CH$_2$Cl$_2$ at 0° C. was added 15 mg (0.086 mmol) of N-Boc glycine, 11.7 mg (0.086 mmol) of N-hydroxybenzotriazole, 9.5 µL (0.086 mmol) of N-methylmorpholine and 24.8 mg (0.12 mmol) of EDC. After stirring overnight at room temperature, the reaction mixture was diluted with water and extracted with ethyl acetate. The combined organic phase was washed with brine and dried over MgSO$_4$. The mixture was filtered and concentrated in vacuo and the residue was purified by preparatory TLC eluting with 5% MeOH/CH$_2$Cl$_2$.

H$^1$-NMR (CDCl$_3$, 300 MHz): 1.44 (s, 9H); 1.55–1.70 (m, 2H); 2.08 (m 2H); 2.71–2.91 (m, 2H); 3.13 (t, 1H); 3.80 (d, 1H); 3.98 (m, 2H); 4.67 (d, 1H); 5.51 (bs, 1H); 6.19 (s, 1H); 7.05 (t, 2H); 7.18–7.31 (m, 4H); 8.08 (s, 1H); 8.41 (d, 2H). FAB ms: C$_{27}$H$_{31}$N$_4$O$_3$F: 478; Observed: 479 (M$^+$+1).

EXAMPLE 6

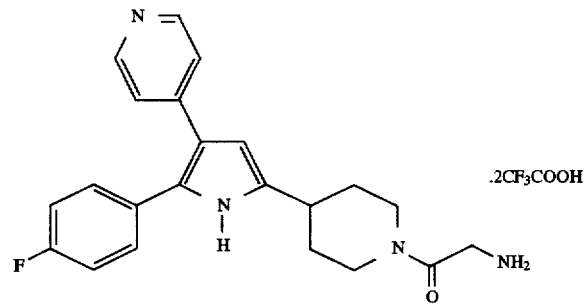

2-(4-fluorophenyl)-5-(N-glycyl)piperidin-4-yl)-3-(4-pyridyl)-pyrrole 9.8 mg of the product prepared in Example 5 was stirred overnight in 50% trifluoroacetic acid in methylene chloride. The reaction mixture was concentrated in vacuo to provide the desired product.

FAB ms: C$_{22}$H$_{23}$N$_4$OF: 378; Observed: 379 (M$^+$+1).

EXAMPLE 7

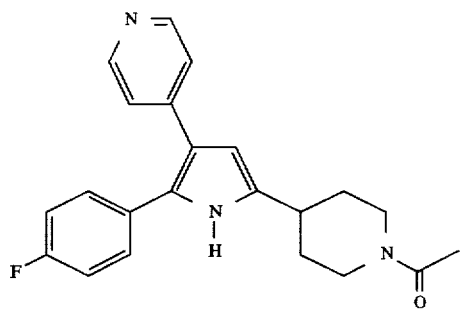

2-(4-fluorophenyl)-5-(N-acetyl-piperidin-4-yl)-3-(4-pyridyl)-pyrrole

A solution of 10.0 mg of the product of Example 4 was dissolved in 0.5 ml of pyridine and treated with 2.6 µL of acetic anhydride. The solution was stirred overnight and diluted with 5 ml water and was extracted with ethyl acetate (2×5 ml). The combined organic phase was dried over MgSO$_4$, filtered and concentrated in vacuo to give the title compound.

FAB ms: C$_{22}$H$_{22}$N$_3$OF: 363; Observed: 364 (M$^+$+1).

EXAMPLE 8

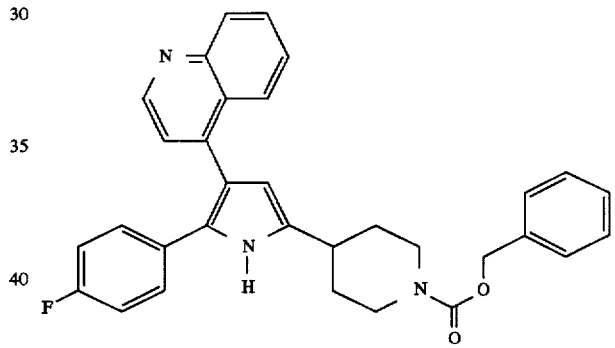

2-(4-fluorophenyl)-5-(N-(CBz)-piperidin-4-yl)-3-(4-quinolinyl)-pyrrole

Step 1

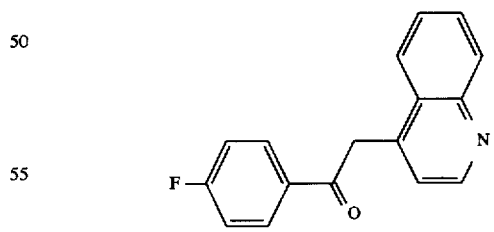

To a solution of 1.94 g of diisopropylamine in 20 ml of THF at −78° C. was added 9.37 g of a 1.6M solution of n-butyl lithium in hexane. After 30 minutes 1.43 g of 4-methylquinoline was added dropwise to give a dark red solution. After 1 hour, 2.26 g of N-methyl-N-methoxy-4-fluorobenzamide in 10 ml of THF was added dropwise. The solution was allowed to warm to room temperature over 1.5 hours. The reaction mixture was diluted with 20 ml of water and extracted with ethyl acetate (3×15 ml). The combined

47 organic extracts were washed with water (1×15 ml) and dried over MgSO$_4$. The mixture was filtered and concentrated in vacuo and the residue was purified by flash chromatography over silica gel eluting with 2% MeOH/CH$_2$Cl$_2$ to provide the desired compound.

Step 2

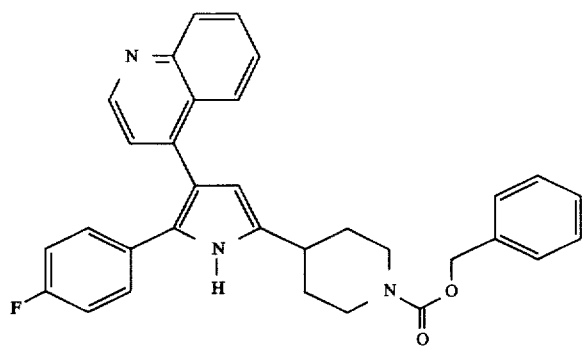

The procedure described in Example 2, step 4 was followed to give the desired product.

H$^1$-NMR (CDCl$_3$, 300 MHz): 1.7 (m, 4H); 2.05 (bm, 2H); 2.80–3.05 (m, 3H); 4.30 9 bm, 2H); 5.12 (s, 2H); 6.12 (s, 1H); 6.81 (t, 2H); 7.02–7.45 (m, 8H); 7.65 (t, 1H); 8.00 (d, 1H); 8.10 (s, 1H); 8.42 (s, 1H); 8.75 (d, 1H). FAB ms: C$_{32}$H$_{28}$N$_3$O$_2$F: 505; Observed: 506 (M$^+$+1).

EXAMPLE 9

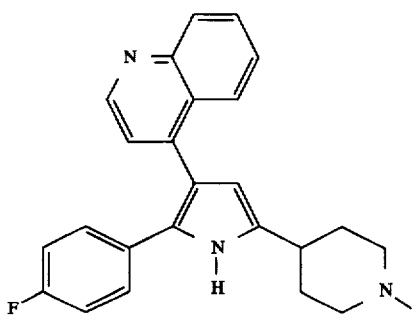

2-(4-fluorophenyl)-5-(4-methylpiperidin-4-yl)-3-(4-quinolinyl)-pyrrole

The product of Example 8 was converted into the title compound by application of the conditions described for Example 4.

H$^1$-NMR (CDCl$_3$, 300 MHz): 1.90 (m, 2H); 2.02–2.18 (m, 4H); 2.35 (s, 3H); 2.68 (m, 2H); 3.0 (d, 2H); 6.14 (s, 1H); 6.82 (t, 2H); 7.03 (m, 2H); 7.19 (d, 1H); 7.38 (m, 2H); 7.64 (t, 1H); 8.02 (d, 1H); 8.09 (d, 1H); 8.30 (bs, 1H); 8.75 (d, 1H). FAB ms: C$_{25}$H$_{24}$N$_3$F: 385; Observed: 386 (M$^+$+1).

Employing the procedures described above, the compounds appearing in the Table below are prepared.

48

TABLE I (structure shown with (R$^a$)$_{0-3}$—HAr, (R$^a$)$_{1-3}$—Ar, and R$^2$ substituents on pyrrole)

| Ex. # | R$^2$ | (R$^a$)$_{1-3}$—Ar | (R$^a$)$_{0-3}$—HAr |
|---|---|---|---|
| 10 | t-butyl | Ph-4-F | 3-methyl-4-pyridyl |
| 11 | t-butyl | Ph-4-F | 4-quinolinyl |
| 12 | t-butyl | Ph-4-F | 2-methyl-4-pyridyl |
| 13 | N-Bn-piperidin-4-yl | Ph-4-F | 4-pyridyl |
| 14 | N-Ph-piperidin-4-yl | Ph-4-F | 4-pyridyl |
| 15 | N-Me-piperidin-4-yl | Ph-4-Cl | 4-pyridyl |
| 16 | N-Me-piperidin-4-yl | Ph-3,4-di-F | 4-pyridyl |
| 17 | N-Me-piperidin-4-yl | Ph-3-Cl | 4-pyridyl |
| 18 | t-butyl | Ph-2-OMe | 4-pyridyl |
| 19 | t-butyl | Ph-3-OMe | 4-pyridyl |
| 20 | t-butyl | Ph-4-OMe | 4-pyridyl |
| 21 | t-butyl | Ph-4-Cl | 4-pyridyl |
| 22 | t-butyl | Ph-3-Cl | 4-pyridyl |
| 23 | t-butyl | Ph-3,4-di-F | 4-pyridyl |
| 24 | t-butyl | Ph-3,4-di-Cl | 4-pyridyl |
| 25 | t-butyl | Ph-3-CF$_3$ | 4-pyridyl |
| 26 | t-butyl | Ph-4-SMe | 4-pyridyl |
| 27 | t-butyl | Ph-4-S(O)Me | 4-pyridyl |
| 28 | 4-piperidinyl | Ph-4-F | 4-pyridyl |
| 29 | N-Me-piperidin-3-yl | Ph-4-F | 4-pyridyl |
| 30 | t-butyl | Ph-4-NO$_2$ | 4-pyridyl |
| 31 | t-butyl | Ph-4-NMe$_2$ | 4-pyridyl |
| 32 | t-butyl | Ph-2-Cl | 4-pyridyl |
| 33 | N-Me-piperidin-4-yl | Ph-3-CF$_3$ | 4-quinolinyl |
| 34 | 4-piperidinyl | Ph-3-CF$_3$ | 4-quinolinyl |
| 35 | N—CBz-piperidin-4-yl | Ph-2-CF$_3$ | 4-(2-F)-pyridyl |
| 36 | N-methylpiperidin-4-yl | Ph-4-F | 2-methylpyridin-4-yl |
| 37 | N-methylpiperidin-4-yl | Ph-3-CF$_3$ | 2-methylpyridin-4-yl |

Me = methyl, CBz = benzyloxycarbonyl Bn = benzyl Ph = phenyl Boc = butoxycarbonyl

EXAMPLE 38

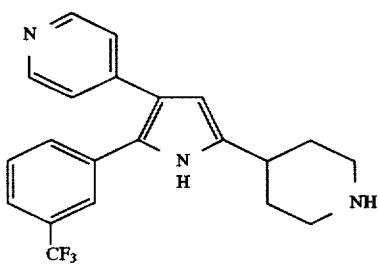

2-(3-trifluoromethylphenyl)-5-(4-piperidyl)-3-(4-pyridinyl)-pyrrole

Step 1: 4-acetyl-1-(benzyloxycarbonyl)piperidine

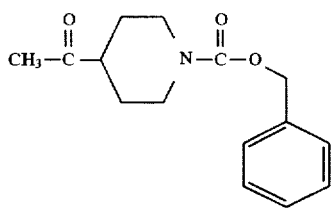

To a stirred solution of 4-acetylpiperidine hydrochloride (22.6 g, 0.138 mol) in saturated aqueous $Na_2CO_3$ (100 mL), cooled to 5° C., was added benzyl chloroformate (23.6 mL, 0.166 mol) dropwise over 10–15 min. The resulting suspension was stirred for ½ hour and was filtered. The solid was recrystallized from hexane (200 mL) and ethyl acetate (20 mL) producing 30.5 g of the title compound as a white solid.
M.P. 87°–89° C.

Step 2: 1-(1-benzyloxycarbonyl-4-piperidinyl)-3-(4-pyridinyl)-2-propen-1-one

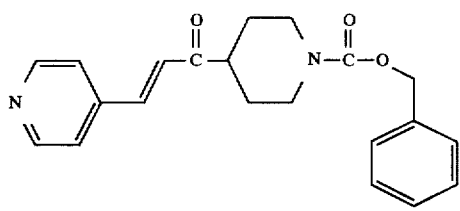

To a solution of 4-pyridinecarboxaldehyde (5.89 g, 0.055 mol), 4-acetyl-1-(N-benzyloxycarbonyl)piperidine (13.07 g, 0.05 mol) and piperidine (4.26 g, 0.005 mol) was added 15 mL of pyridine. The mixture was stirred in an oil bath at 100° C. for 20 hours, and the volatile components were removed in vacuo. The residual oil was chromatographed on silica gel, eluting with ethyl acetate to produce the title compound (3.78 g) as a colorless oil, which formed a pale yellow solid.
M. P. 106°–112° C.

Step 3: 4-(1-benzyloxycarbonylpiperidin-4-yl)-2-(4-pyridyl)-1-(3-trifluoromethylphenyl)butane-1,4-dione

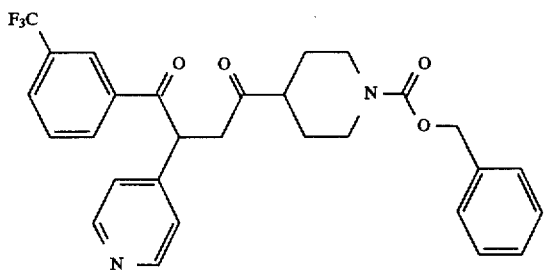

To m-trifluoromethylbenzaldehyde (2.44 g, 0.014 mol) in 5 mL of DMF was added NaCN (0.147 g, 0.003 mol) and the mixture was stirred under argon for 1 hour. This solution was added to 1-(1-benzyloxycarbonyl-4-piperidinyl)-3-(4-pyridyl)-2-propen-1-one in 10 mL of DMF. The mixture was stirred at 65°–75° C. for 20 hours. The volatile components were removed in vacuo. The residual oil was taken up in EtOAc and sat'd NaCl. The EtOAc extract was separated, dried, filtered and concentrated in vacuo to form an oil. The crude oil was chromatographed on silica gel eluting with ethyl acetate, producing 3.45 g of the title compound as a yellow foam.

Step 4: 5-(1-benzyloxycarbonyl-4-piperidinyl)-3-(4-pyridyl)-2-(3-trifluoromethylphenyl)-pyrrole

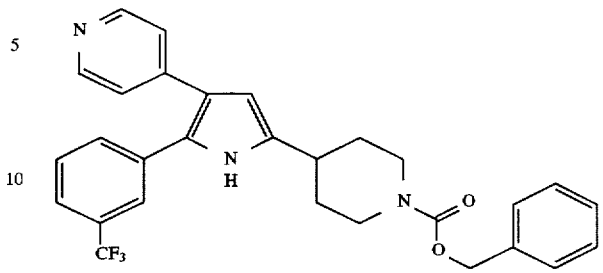

The 1,4-diketone from step 3 (3.45 g, 6.6 mmol) was reacted with ammonium acetate (20.3 g, 0.264 mol) and 50 mL of acetic acid using the procedure of Example 1, step 3, producing 3.28 g of the title compound.

M. P. 180°–181° C.

Step 5: 3-(4-pyridyl)-5-(4-piperidinyl)-2-(3-trifluoromethylphenyl)pyrrole

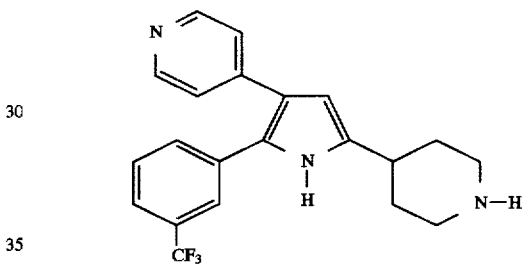

The product from step 4 (3.0 g, 0.006 mol) was debenzylated in 5 mL of 30% HBr in acetic acid and 5 mL of methylene chloride, producing the title compound as a solid.

M. P. 238°–240° C.

EXAMPLE 39

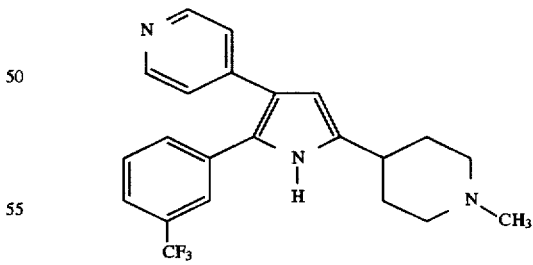

The product from Example 38, Step 4 (1.15 g, 2.27 mmol) was reduced with lithium aluminum hydride (0.86 g, 2.27 mmol) using the procedure of Example 3. The N-methylpiperidinyl analog was obtained.

M. P. 221°–222° C.

EXAMPLE 40

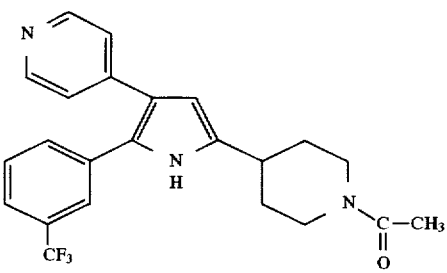

The N-acetylpiperidinyl analog was prepared from the product of Example 38 was prepared using acetyl chloride and triethylamine in THF in place of acetic anhydride and pyridine, as described in Example 7, producing the target compound as a solid.

M. P. 196°–198° C.

EXAMPLE 41

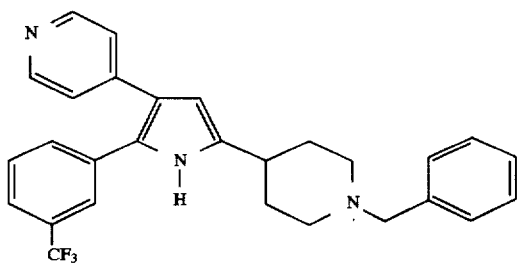

The product of Example 38 (111 mg, 0.3 mmol) was reacted with benzaldehyde (35 mg, 0.33 mmol) in a reductive amination using sodium triacetoxyborohydride (95 mg, 0.45 mmol) in 3 mL of 1,2-dichloroethane and 2 mL of THF, producing the target compound as a solid.

M. P. 212°–214° C.

EXAMPLE 42

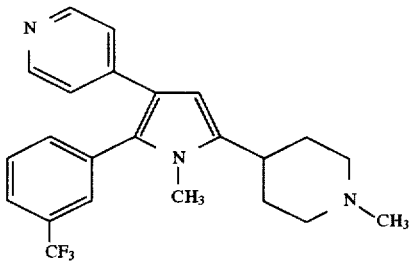

Powdered KOH (78 mg, 1.39 mmol) was stirred in 1 mL of DMSO for 5 min. The product of Example 54 (134 mg, 0.348 mmol) was added and the mixture was stirred for ¾ hour. Methyl iodide (49 mg, 0.348 mmol) was added and the solution was stirred for 1¼ hours at room temperature. Another 49 mg of methyl iodide was added. After ½ hour, 10 mL of water was added and the mixture was extracted with ethyl acetate. The crude product isolated from ethyl acetate was chromatographed on silica gel, eluting with 20% methanol-chloroform, to produce the target compound as a solid.

EXAMPLE 43

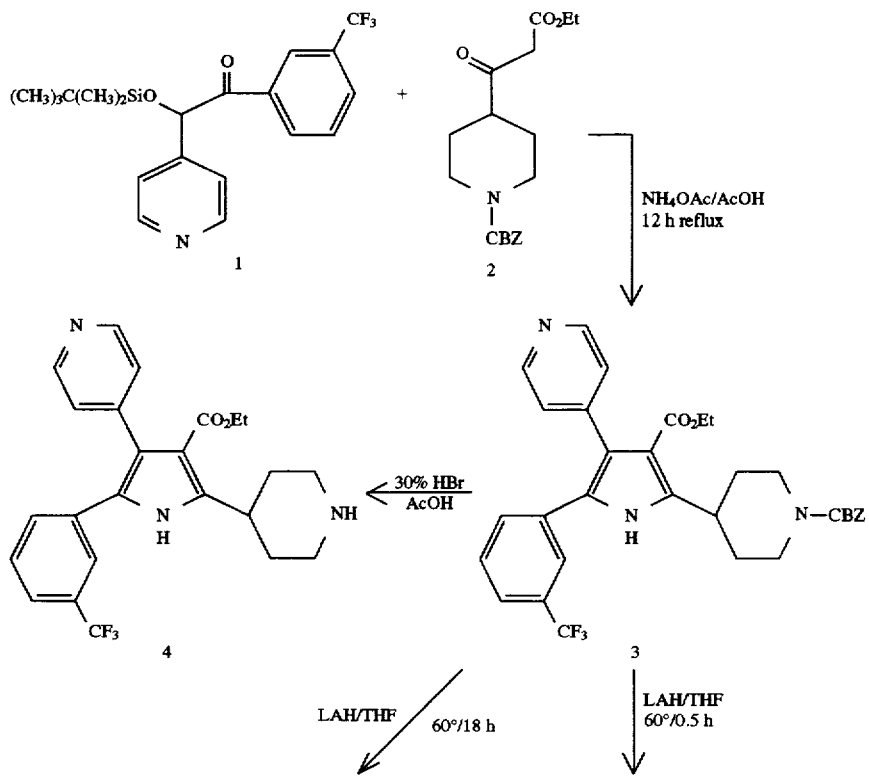

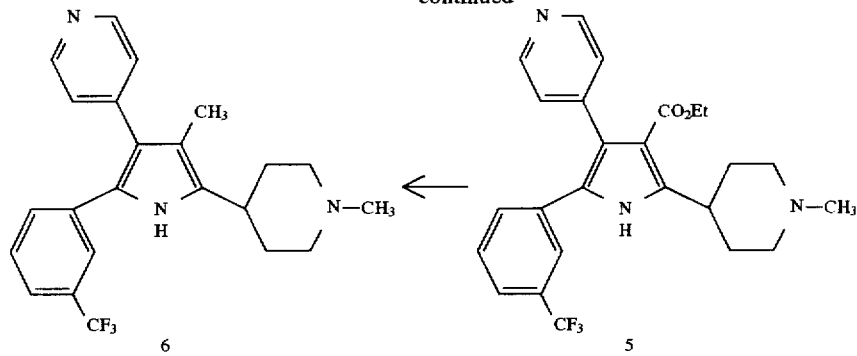

CBZ = carboxybenzyl

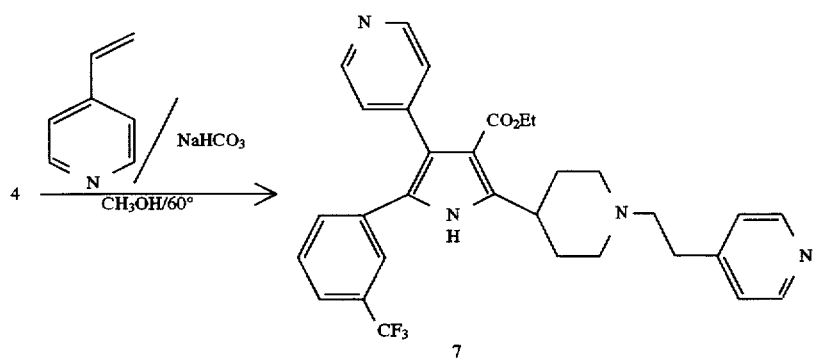

Preparation of 3-trifluoromethyl-2-(4-pyridyl)-2-tert butyldimethylsilyloxyacetophenone (1)

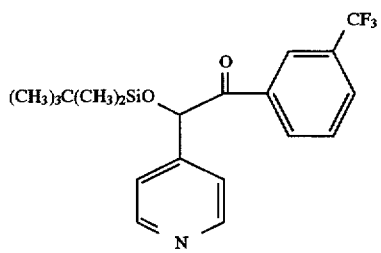

To a 2 liter 3-neck flask equipped with a mechanical stirrer under $N_2$ was added 54.6 g (0.59 m) of diisopropylethylamine and 150 mL of THF. The solution was cooled to −20° C. and treated with 268 mL (0.67 m) of 2.5M n-butyl lithium over 20 min. To the reaction mixture was added 125 g (0.56 m) of 4-(t-butyldimethylsilyloxymethyl)pyridine in 100 mL of THF over 30 min. The reaction mixture was stirred for 1 hr. at −15° C. and then treated dropwise with a solution of 108 g (0.59 m) of 3-trifluoromethylbenzaldehyde dissolved in 100 mL of THF. The reaction was warmed to 0° C., stirred for 1 hr. warmed to room temperature and then quenched by the addition of 1 L of 20% $NH_4Cl$ solution. The aqueous phase was extracted with EtOAc (3×500 mL).

The combined organic phases were washed with water (1×500 mL), 1×500 mL brine and then dried over $MgSO_4$. The mixture was filtered and the filtrate was concentrated in vacuo to give a dark oil. The product was purified by flash chromatography over silica gel eluting with 10–20% EtOAc/hexanes.

Preparation of 5-[(N-benzyloxycarbonyl)piperidin-4-yl]-4-carboethoxy-3-(4-pyridyl)-2-(3-trifluoromethylphenyl) pyrrole (3)

A mixture of compound 2, prepared in accordance with J. Med. Chem. Vol. 38, p. 3293 (1995), 0.7 equivalents of the product of Step 1, and 4 equivalents of ammonium acetate are heated in acetic acid at reflux. The reaction mixture is diluted with ethyl acetate, washed with water and brine, and dried over $MgSO_4$. The mixture is filtered and then concentrated in vacuo, and the residue is purified by chromatography over silica gel to give the desired product.

Preparation of 5-[piperidin-4-yl]-4-carboethoxy-3-(4-pyridyl)-2-(3-trifluoromethylphenyl)pyrrole (4)

A mixture of 3 (0.4 g, 0.69 mmol) and 4 mL of 30% HBr in AcOH was stirred under $N_2$ for 1 hour. The mixture was then treated with EtOAc-Et$_2$O-1N HCl and the phases were separated. The aqueous layer was extracted with EtOAc, neutralized with saturated $NaHCO_3$ and extracted with EtOAc (3×). The organic extracts were dried, filtered and concentrated to dryness. The residue was chromatographed on a column (40 mm) and the product eluted with 5% $CH_3OH$—$CHCl_3$ saturated with ammonia. M.P. 233°–5° C. (EtOAc-Hexanes).

Analysis calculated for $C_{24}H_{24}F_3N_3O_2 \cdot 0.5\ H_2O$: C, 63.70; H, 5.57; N, 9.29 Found: C, 63.98; H, 5.46; N, 9.20.

$^1$H NMR (CDCl$_3$ 300 MHz) 1.0 (t,3H); 1.85 (m, 5H); 2.8 (t, 2H); 3.2 (d, 2H) 3.7(t, 1H); 4.1(q, 2H); 7.16 (d, 3H); 7.3 (t, 1H), 7.4(s, 1H); 7.46 (d, 1H); 8.52 (d, 2H); and 8.94 (bs, exch 1H).

Preparation of 5-[N-methylpiperidin-4-yl]-4-carboethoxy-3-(4-pyridyl)-2-(3-trifluoromethylphenyl)pyrrole (5)

Under Ar, a solution of 3 in THF (70 ml) was treated at room temperature with 1N LAH (30 ml, 30 mmol) and then heated to 60° C. After 0.5 h, the reaction mixture was cooled to room temperature and treated with saturated $Na_2SO_4$. The suspension was filtered and the precipitate washed with EtOAc. Water was added to the filtrate, the liquid phases separated and the aqueous fraction was extracted with 2 additional EtOAc washes. The combined organic extracts were washed with brine, dried, filtered and concentrated to dryness. The residue was chromatographed on a column (40 mm) and the product eluted with 10% CH$_3$OH—CHCl$_3$ saturated with ammonia.

M.P. 223°–5° C. (EtOAc-Hexanes).

Analysis calculated for C$_{25}$H$_{26}$F$_3$N$_3$O$_2$.0.25H$_2$O: C, 64.99; H, 5.78; N, 9.10 Found: C, 65.08; H, 5.70; N, 9.06.

$^1$H NMR (CDCl$_3$ 300 MHz) 1.0 (t, 3H); 1.8 (m, 2H); 2.1 (m, 4H); 2.15 (s, 3H); 3.0 (d, 2H), 3.6 (m, 1H); 4.05 (q, 2H); 7.16 (d, 3H); 7.3 (t, 1H); 7.38 (s, 1H); 7.45 (d, 1H); 8.55 (d, 2H); 8.81 (bs, 1H).

Preparation of 5-(N-methylpiperidin-4-yl)-4-methyl-3-(4-pyridyl)-2-(3-trifluoromethylphenyl)pyrrole (6)

Using the procedure described for the preparation of 5 and refluxing the mixture overnight provided 6.

M.P. 245°–7° C. (CH$_2$Cl$_2$-Hexanes).

Under Ar, a mixture of 4 (0.25 g, 0.56 mmol), NaHCO$_3$ (100 mg, 1.2 mmol), CH$_3$OH (5 ml) and 4-vinylpyridine (0.47 g, 4.6 mmol) was heated at reflux. After 18 hours, the reaction was poured into a saturated NaHCO$_3$ solution and extracted with EtOAc (3×). The organic extracts were dried, filtered and concentrated to dryness. The residue was chromatographed on a column (40 mm) and the product eluted with CHCl$_3$ saturated with NH$_3$.

M.P. 176°–7° C. (EtOAc-Hexanes).

Analysis calculated for C$_{31}$H$_{31}$F$_3$N$_4$O$_2$: C, 67.87; H, 5.70; N, 10.21 Found: C, 67.67; H, 5.60; N, 10.21.

EXAMPLE 44

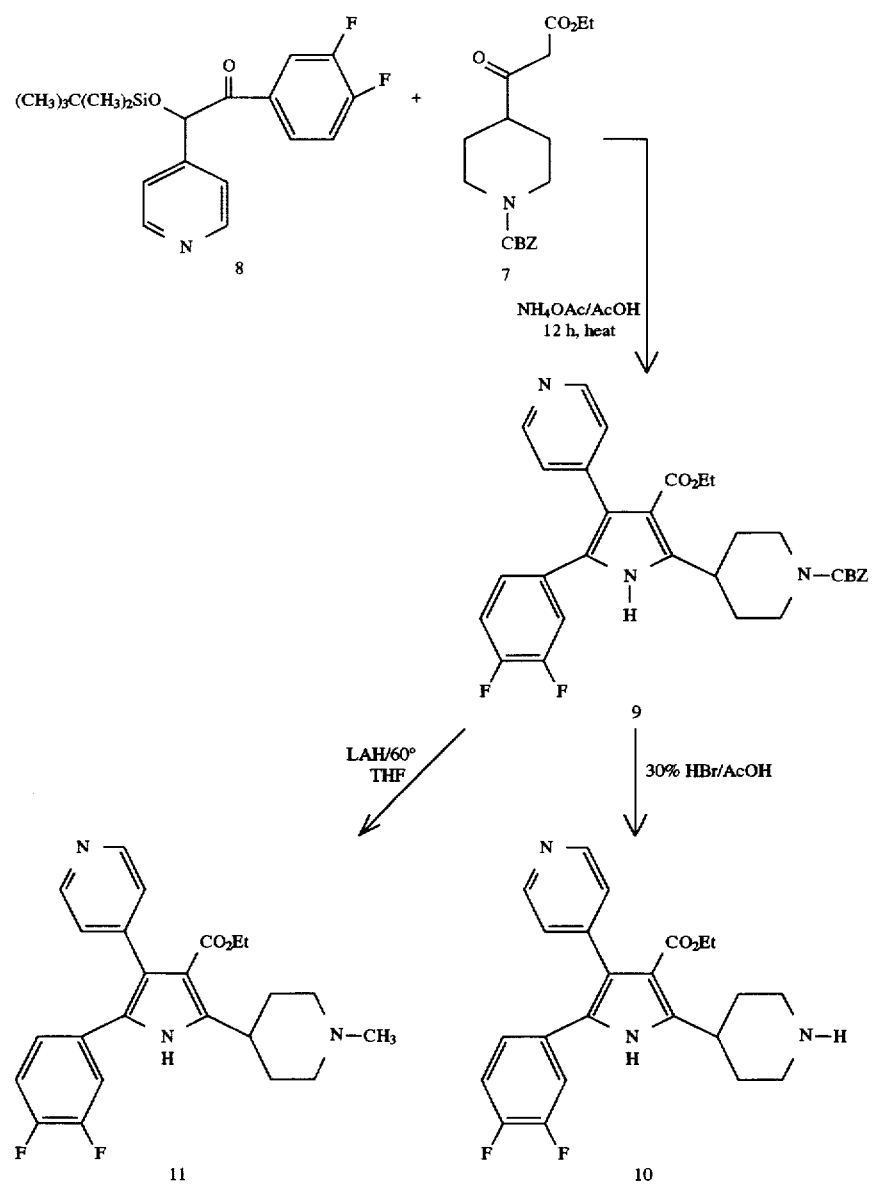

Analysis calculated for: C$_{23}$H$_{24}$F$_3$N$_3$: C, 69.15; H, 6.06; N, 10.52 Found: C, 68.78; H, 5.97; N, 10.56.

Preparation of 5-[N-(2-ethylpyridin-4-yl) piperidin-4-yl]-4-carboethoxy-3-(4-pyridyl)-2-(3-trifluoromethylphenyl) pyrrole (7)

Preparation of 3,4-difluoro-2-(4-pyridyl)-2-tert butyldimethylsilyloxyacetophenone (8)

Using the procedure described in Example 43, Step 1, compound 8 was prepared by substituting 3,4-difluoro-(N- methyl-N-methoxy)benzamide in place of 4-fluoro-(N-methyl-N-methoxy)benzamide.

Preparation of 5-|(N-benzyloxycarbonyl)piperidin-4-yl|-4-carboethoxy-3-(4-pyridyl)-2-(3,4-difluoromethylphenyl)pyrrole (9)

Using the procedure described in Example 43, Step 2, compound 9 was prepared.

Preparation of 5-(piperidin-4-yl)-4-carboethoxy-3-(4-pyridyl)-2-(3,4-difluorophenyl)pyrrole (10)

Using the procedure described in Example 43 to prepare 4, compound 10 was prepared.

M.P. 261°–2° C. (EtOAc).

Analysis calculated for $C_{23}H_{23}F_2N_3O_2 \cdot 0.5\ H_2O$: C, 65.70; H, 5.75; N, 9.99 Found: C, 65.97; H, 5.51; N, 9.88.

$^1$H NMR (DMSO-$d_6$ 300 MHz) 0.95 (t, 3H); 1.75 (m, 4H); 2.5 (m, 4H); 3.05 (d, 2H); 3.5 (m, 1H); 3.95 (q, 2H); 6.9 (d, 1H); 7.15 (d, 2H); 7.3 (m, 3H); 8.45 (d, 2H); 11.5 (bs, 1H).

Preparation of 5-|N-methylpiperidin-4-yl|-4-carboethoxy-3-(4-pyridyl)-2-(3,4-difluorophenyl)pyrrole (11)

Using the procedure described in Example 43 to prepare 5, the title compound 11 was prepared.

M.P. 262°–5° C. (EtOAc).

Analysis calculated for $C_{24}H_{25}F_2N_3O_2$: C, 67.75; H, 5.92; N, 9.88 Found: C, 67.61; H, 5.92; N, 9.67.

$^1$NMR (CDCl$_3$ 300 MHz) 1.0 (t, 3H); 1.8 (m, 2H); 2.1 (m, 4H); 2.35 (s, 3H); 3.0 (d, 2H); 3.6 (m, 1H); 4.05 (q, 2H); 7.16 (d, 3H); 7.31 (t, 1H); 7.38 (s, 1H); 7.45 (d, 1H); 8.51 (d, 2H); and 8.82 (bs, 1H).

EXAMPLE 45

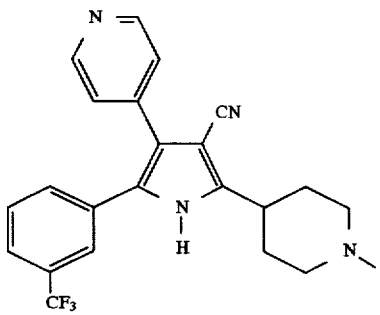

A mixture of 1-(4-N-methylpiperidinyl)-2-cyanoethanone, 0.7 equivalents of the reaction product of Example 43, Step 1, and 4 equivalents of ammonium acetate are heated in acetic acid at reflux until the benzoin is consumed. The reaction mixture is diluted with EtOAc and washed with water and brine and dried over MgSO$_4$. The mixture is filtered and the filtrate is concentrated in vacuo. The residue is purified by chromatography over silica gel to give the desired product.

EXAMPLE 46

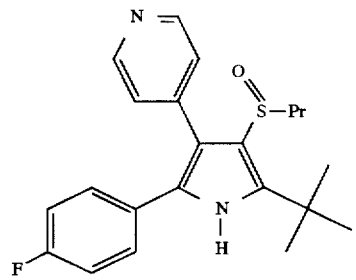

The product of Example 1 is dissolved in methylene chloride and treated with 1.05 equivalents of n-propylsulfinyl chloride at 0° C. under nitrogen. After 30 minutes triethylamine is added to neutralize the reaction mixture. The reaction mixture is diluted with ethyl acetate and washed with water and brine and dried over MgSO$_4$. The mixture is filtered and the filtrate is concentrated in vacuo and the residue is purified by chromatography over silica gel to give the desired product.

EXAMPLE 47

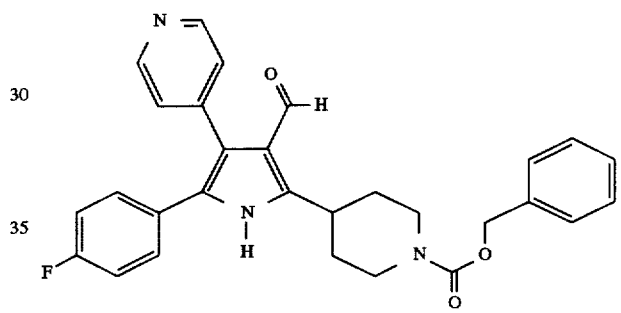

To 5 ml of DMF at room temperature under nitrogen is added 0.3 g (2 mmol) of POCl$_3$ dropwise. After 15 minutes a solution of 0.37 g (0.86 mmol) of the product of Example 2 is added dropwise. The solution was warmed at 60° C. until the starting material had been consumed. The reaction mixture was cooled to room temperature and then poured into ice water (20 ml). The mixture was made basic by addition of saturated sodium carbonate solution and then stirred in the presence of 20 mL of chloroform. The chloroform phase was separated and the aqueous phase was extracted with chloroform (2×10 mL). The combined organic phase is washed with water and brine and dried over MgSO$_4$. The mixture is filtered and the filtrate is concentrated in vacuo and the residue is purified by chromatography over silica gel to give the desired product.

EXAMPLE 48

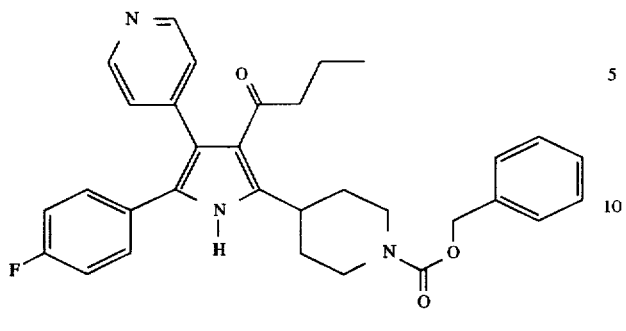

To 5 ml of N,N-dimethylbutyramide at room temperature under nitrogen is added 0.3 g (2 mmol) of POCl$_3$ dropwise. After 15 minutes a solution of 0.37 g (0.86 mmol) of the product of Example 2 is added dropwise. The solution is warmed at 60° C. until the starting material had been consumed. The reaction mixture is cooled to room temperature and then poured into ice water (20 ml). The mixture is made basic by addition of saturated sodium carbonate solution and then stirred in the presence of 20 mL of chloroform. The chloroform phase is seperated and the aqueous phase extracted with chloroform (2×10 ml). The combined organic phase is washed with water and brine and dried over MgSO$_4$. The mixture is filtered and the filtrate is concentrated in vacuo. The residue is purified by chromatography over silica gel to give the desired product.

EXAMPLE 49

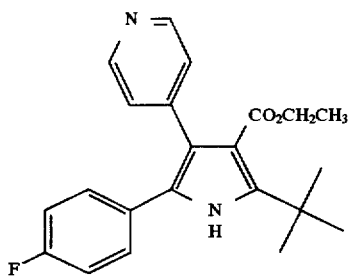

Using the procedure set forth in Example 43, substitute EtO$_2$CCH$_2$C(O)C(CH$_3$)$_3$ for compound 2 to produce the desired compound.

EXAMPLE 50

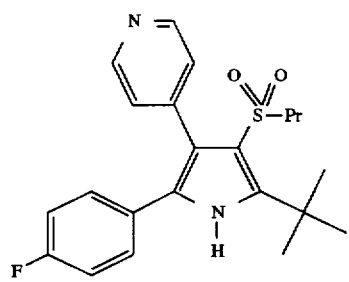

The product of Example 1 is reacted with 1.05 equivalents of meta-chloroperoxybenzoic acid in CH$_2$Cl$_2$ at 0° C. The reaction mixture is stirred overnight at room temperature. The solution is diluted with EtOAc and washed with saturated sodium bicarbonate solution followed by brine. The solution is dried over MgSO$_4$, filtered and concentrated in vacuo. The residue is purified by silica gel chromatography to produce the desired product.

EXAMPLE 51

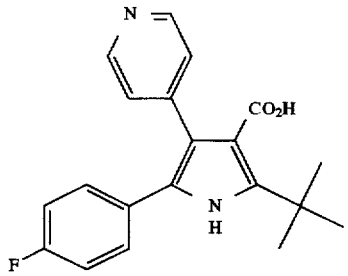

The product of Example 49 is heated with excess lithium hydroxide in DME/water at reflux until the conversion to the acid is complete. The reaction mixture is acidified with acetic acid and extracted with ethyl acetate to give the desired product.

EXAMPLE 52

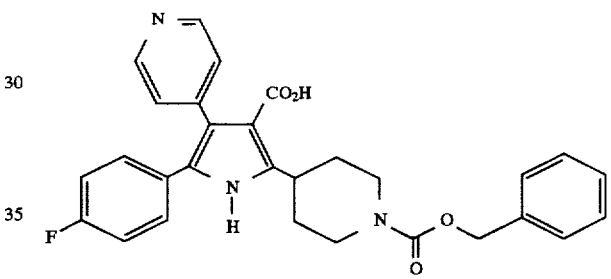

The product of Example 47 is dissolved in t-butyl alcohol and methyl 2- butene (6:1 ratio). The solution is then treated with 1.5 eq of monobasic sodium phosphate and an aqueous solution of sodium chlorate. The reaction mixture is stirred at room temperature until the starting material is consumed. The pH is adjusted to 5.5 with dilute HCl. The product is extracted with ethyl acetate and the combined organic phase is washed with water and brine and dried over MgSO$_4$. The mixture is filtered and the filtrate is concentrated in vacuo to give the desired product.

EXAMPLE 53

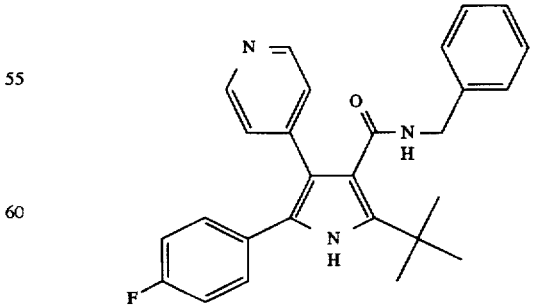

The product of Example 51 is dissolved in DMF and treated with 1-(3-dimethylaminopropyl)-3- ethylcarbodiimide hydrochloride, benzylamine, Hunig's base and a catalytic amount of DMAP. The mixture is stirred overnight at room temperature. The solution is diluted with water and extracted with ethyl acetate. The organic phase is washed with water and brine and is dried over $MgSO_4$, filtered and trated in vacuo. The residue is purified by chromatography.

EXAMPLES 54–109

Employing the procedures described above, the following unds of Formula I can be prepared.

TABLE II

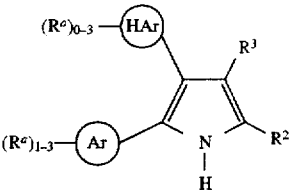

| Ex. # | $R^2$ | $(R^a)_{1-3}$—Ar | $(R^a)_{0-3}$—HAr | $R^3$ |
|---|---|---|---|---|
| 54 | t-butyl | Ph-4-F | 2-methyl-4-pyridyl | CN |
| 55 | t-butyl | Ph-4-F | 2-methyl-4-pyridyl | COMe |
| 56 | t-butyl | Ph-4-F | 2-methyl-4-pyridyl | CONHMe |
| 57 | t-butyl | Ph-4-F | 2-methyl-4-pyridyl | SO₂Et |
| 58 | t-butyl | Ph-4-F | 2-methyl-4-pyridyl | COOEt |
| 59 | t-butyl | Ph-4-F | 4-quinolinyl | CN |
| 60 | t-butyl | Ph-4-F | 2-quinolinyl | CN |
| 61 | t-butyl | Ph-4-F | 2-pyrinidinyl | CN |
| 62 | t-butyl | Ph-4-F | 4-pyrimidinyl | CN |
| 63 | t-butyl | Ph-4-F | 3-pyridazinyl | CN |
| 64 | t-butyl | Ph-4-F | 2-pyrazinyl | CN |
| 65 | t-butyl | Ph-4-F | 2-pyrimidinyl | CN |
| 66 | t-butyl | Ph-4-F | 4-pyrimidinyl | CN |
| 67 | t-butyl | Ph-4-F | 2-imidazo-(4,5-b)-pyridinyl | CN |
| 68 | t-butyl | Ph-4-F | 4-(2-amino)-pyridyl | CN |
| 69 | t-butyl | Ph-4-F | 4-(2-N-benzyl-amino)-pyridyl | CN |
| 70 | t-butyl | Ph-4-F | 4-(2-acetylamino)-pyridyl | COMe |
| 71 | t-butyl | Ph-4-F | 4-pyridyl | CN |
| 72 | t-butyl | Ph-4-F | 4-pyridyl | CONH-iBu |
| 73 | t-butyl | Ph-4-F | 4-pyridyl | COMe |
| 74 | i-butyl | Ph-4-F | 4-pyridyl | CN |
| 75 | N-Me-piperidin-4-yl | Ph-4-F | 4-pyridyl | COMe |
| 76 | N-Bn-piperidin-4-yl | Ph-4-F | 4-pyridyl | COMe |
| 77 | N-Ph-piperidin-4-yl | Ph-4-F | 4-pyridyl | COMe |
| 78 | CH₂-4-(N-Me)-piperazinyl | Ph-4-F | 4-pyridyl | CN |
| 79 | N-Me-piperidin-4-yl | Ph-4-F | 4-pyridyl | CN |
| 80 | N-Me-piperidin-4-yl | Ph-4-Cl | 4-pyridyl | CN |
| 81 | t-butyl | Ph-2-OMe | 4-pyridyl | CN |
| 82 | t-butyl | Ph-3-OMe | 4-pyridyl | CN |
| 83 | t-butyl | Ph-4-OMe | 4-pyridyl | CN |
| 84 | t-butyl | 4-(4-(N—COCH₃)-piperazinyl)-Ph | 4-pyridyl | CN |
| 85 | t-butyl | 4-(morpholinyl)-Ph | 4-pyridyl | CN |
| 86 | t-butyl | Ph-4-Cl | 4-pyridyl | CN |
| 87 | t-butyl | Ph-3-Cl | 4-pyridyl | CN |
| 88 | t-butyl | Ph-3,4-di-Cl | 4-pyridyl | CN |
| 89 | t-butyl | Ph-3-CF₃ | 4-pyridyl | CN |
| 90 | t-butyl | Ph-4-S-Me | 4-pyridyl | CN |
| 91 | t-butyl | Ph-4-S(O)-Me | 4-pyridyl | CN |
| 92 | 4-piperidinyl | Ph-4-F | 4-pyridyl | CN |
| 93 | 3-N-Me-piperidinyl | Ph-4-F | 4-pyridyl | CN |
| 94 | CH₂-morpholin-1-yl | Ph-4-F | 4-pyridyl | CN |
| 95 | t-butyl | Ph-4-NO₂ | 4-pyridyl | CN |
| 96 | t-butyl | Ph-4-NMe₂ | 4-pyridyl | CN |
| 97 | t-butyl | Ph-2-Cl | 4-pyridyl | CN |
| 98 | 4-piperidinyl | Ph-4-F | 4-pyridyl | CN |
| 99 | t-butyl | Ph-4-F | 2-pyridyl | CN |
| 100 | t-butyl | Ph-4-F | 2-methyl-4-pyridyl | CN |
| 101 | t-butyl | Ph-4-F | 3-methyl-4-pyridyl | CN |
| 102 | cyclohexyl | Ph-4-F | 4-pyridyl | CN |
| 103 | i-propyl | Ph-4-F | 4-pyridyl | CN |
| 104 | 1-cyclo-propyl-ethyl | Ph-4-F | 4-pyridyl | CN |
| 105 | t-butyl | Ph-4-F | 2,4-dimethylpyridin-4-yl | CN |
| 106 | 4-(N—Cbz)-piperidinyl | Ph-4-F | 4-pyridyl | H |
| 107 | 4-(N—Cbz)-piperidinyl | Ph-4-F | 4-quinolinyl | H |
| 108 | 4-(N—Cbz)-piperidinyl | 3-(CF₃)-Ph | 4-(2-F)-pyridyl | |
| 109 | t-butyl | Ph-4-F | 2,6-dimethylpyridyl | CN |

EXAMPLE 110

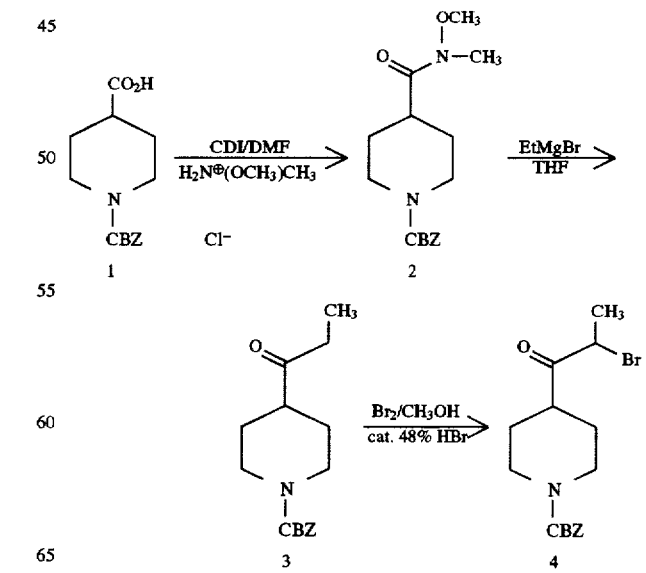

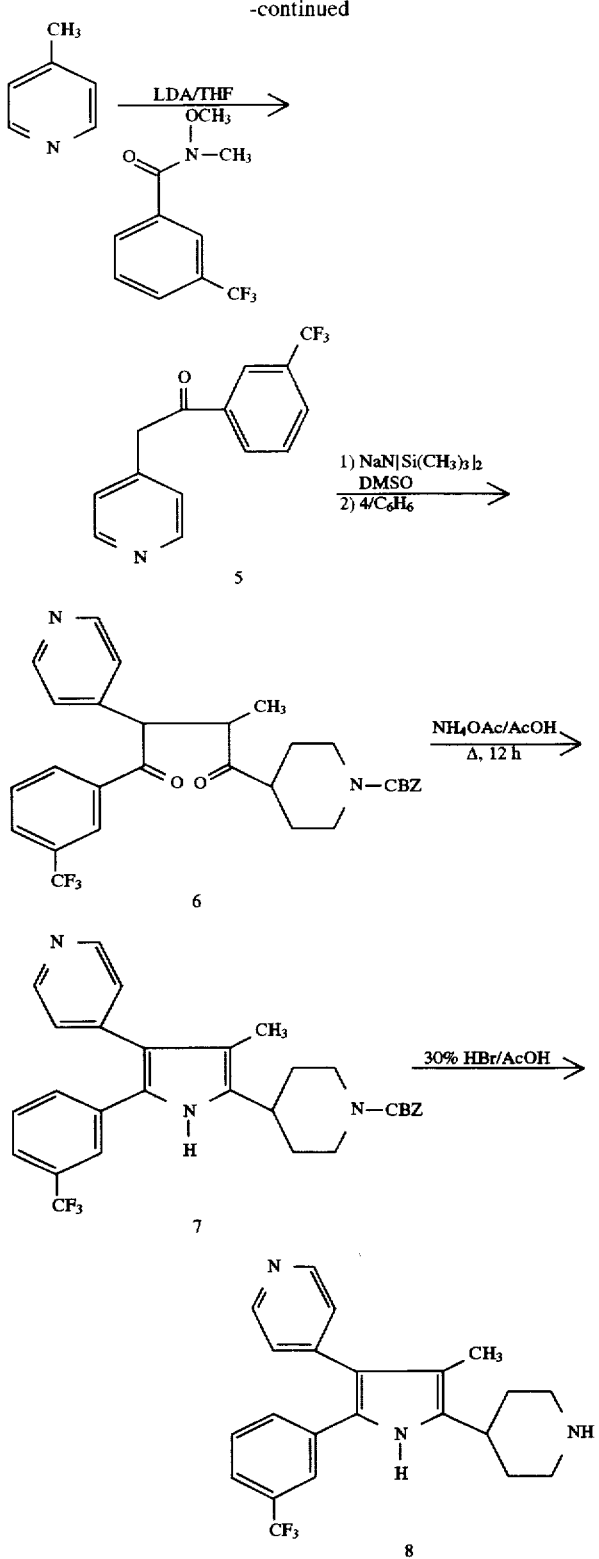

reaction mixture was poured in 1.5N HCl and then extracted with EtOAc (3×). The organic extracts were backwashed with saturated NaHCO$_3$, dried, filtered and concentrated to dryness. The residue was chromatographed on a column (90 mm) and the product eluted with 50–60% EtOAc-Hexanes to yield 2.

Preparation of 3-(N-benzyloxycarbonylpiperidin-4-yl)-3-oxopropane (3)

To a cooled solution at −10° C. of 2 (4.0 g, 13 mmol) in THF (75 ml) was added dropwise under N$_2$ a solution of 3M ethyl-magnesium bromide in Et$_2$O (11 ml, 33 mmol). After addition, the ice bath was removed and allowed to stir to room temperature. After 0.5 h, the reaction was poured into 3N HCl and the aqueous mixture was extracted with EtOAc (3×). The combined organic extracts were washed with brine, saturated NaHCO$_3$, dried, filtered and concentrated to dryness to yield 3.6 g of 3.

Preparation of 2-bromo-3-(N-benzyloxycarbonylpiperidin-4-yl)-3-oxopropane (4)

To a solution of 3 (3.3 g, 11.6 mmol) in CH$_3$OH (50 ml) under Ar with 48% HBr (100 µL) was added dropwise at room temperature bromine (1.9 g, 11.8 mmol). After stirring overnight, the solution was poured in saturated NaHCO$_3$ and the aqueous solution extracted with EtOAc (3×). The combined organic extracts were backwashed with brine, dried, filtered and concentrated to dryness to yield 4.3 g of 4.

Preparation of 3-trifluoromethyl-2-(4-pyridyl)acetophenone (5)

Under Ar, a solution of diisopropylamine (9.5 g, 0.094 mol) in THF (100 mL) was cooled to −78° C. and 38 mL of 2.5M n-Bu Li in hexane (0.094 mol) was added dropwise. After 10 min at −78° C., 4-picoline (5.9 g, 0.064 mol) was added.

The solution was stirred for 15 min at −78° C. and then 3-trifluoromethyl-(N-methyl-N-methoxy)benzamide (15 g, 0.064 mol) in THF (60 mol) was added dropwise at −78° C. After 15 min, the reaction was allowed to stir at room temperature. After 3 hours, the reaction was poured into saturated NH$_4$Cl and extracted with EtOAc (3×). The combined organic extracts were washed with brine, dried, filtered and concentrated to dryness to yield 17 g of the title compound 5.

Preparation of 5-[(N-benzyloxycarbonyl)piperidin-4-yl)-4-methyl-3-(4-pyridyl)-2-(3-trifluoromethylphenyl)pyrrole (7)

To a solution of 5 (1.5 g, 5.7 mmol) in DMSO (10 mL) was added under Ar at room temperature 1.0M sodium bistrimethyl silyamide in THF (6 mmol). After 0.5 hours, a solution of 4 (2.0 g, 5.6 mmol) in DMSO (5 mL) was added dropwise. After 5.5 hours, 2N AcOH (50 mL) was added and the resulting solution extracted with EtOAc (3×). The combined organic extracts were washed with water, brine, dried, filtered and concentrated to dryness to yield crude 6. The residue was treated with NH$_4$OAc (3.0 g, 39 mmol) and acetic acid (25 mL) and heated to reflux. After 12 hours, the reaction was poured into H$_2$O and extracted with EtOAc (3×). The combined organic extracts were backwashed with H$_2$O, saturated Na$_2$CO$_3$, dried, filtered and concentrated to dryness. The residue was chromatographed on a column (60 mm) and the product eluted with 30–50% EtAOc/Hexanes to yield 370 mg of compound 7.

Preparation of 5-(piperidin-4-yl)-4-methyl-3-(4-pyridyl)-2-(3-trifluormethylphenyl)pyrrole (8)

Under Ar, a mixture of 7 (370 mg, 0.7 mmol) in 30% HBr-acetic acid (4 mL) was stirred at room temperature. After 1 hour, the reaction was partitioned between 2N HCl-EtOAc. The aqueous layer was poured into saturated Na$_2$CO$_3$ and extracted with EtOAc (3×). The combined Preparation of N-benzyloxycarbonylpiperidin-4-(N-methyl-N-methoxy)carboxamide (2)

To a solution of 1 (6.6 g, 0.025 mol) in DMF (20 ml) stirred at room temperature under N$_2$ was added carbonyl-diimidazole (6.8 g, 0.042 mol). After stirring for 0.5 h, N,O-dimethylhydroxylamine.HCl (4.4 g, 0.045 mol) was added. After stirring overnight at room temperature, the organic extracts were dried, filtered and concentrated to dryness to yield 79 mg of compound 8.

M.P. 239°–241° C. (EtOAc).

¹H NMR (DMSO 300 MHz) 1.8 (m, 4H); 2.0 (s, 3H); 2.8 (m, 3H); 3.2 (d, 2H); 3.35 (bs, exch); 7.15 (d, 2 h); 7.45 (m, 4 h); 8.45 (d, 2 h), 11.0 (br, 1 exch).

Analysis calculated for $C_{22}H_{22}F_3N_3$·2.25 $H_2O$: C, 62.03; H, 6.27; N, 9.87. Found: C, 62.08; H, 5.60; N, 966.

Utilizing the procedures described in the preceeding examples, the following compounds were prepared.

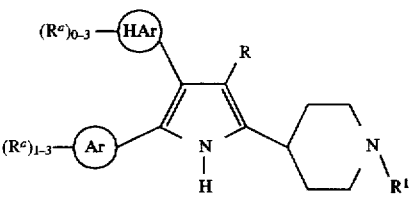

| Ex. | $(R^e)_{1-3}$—Ar | $(R^a)_{0-3}$—HAr | R | $R^1$ | M.P. °C. | Solvent |
|---|---|---|---|---|---|---|
| 111 | 3,4-di-F—$C_6H_3$ | 4-$C_5H_4N$ | $CH_3$ | $CH_3$ | >300 | MeOH/EtOAc |
| 112 | 3-$CF_3$—$C_6H_4$ | 4-$C_5H_4N$ | Ethyl | $CH_3$ | 229–31 | — |
| 113 | 3,4-di-Cl-$C_6H_4$ | 4-$C_5H_4N$ | $CH_3$ | $CH_3$ | | triturate Hxns |
| 114 | 3,4-di-Cl-$C_6H_4$ | 4-$C_5H_4N$ | $CH_3$ | H | | EtOAc/Hxns |
| 115 | 3-$CF_3$—$C_6H_4$ | 4-$C_5H_4N$ | $CH_3$ | $SO_2C_6H_5$ | 237–9 | EtOAc/Hxns |

EXAMPLE 116

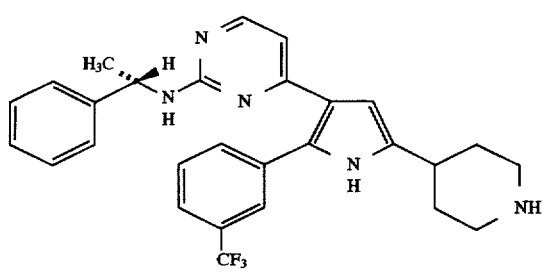

Step 1

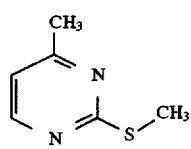

2-Mercapto-4-methylpyrimidine hydrochloride (100 g, 0.617 mol), dimethylformamide dimethylacetal (100 mL, 0.754), diisopropylethylamine (161 mL, 0.926 mol), and toluene (200 mL) were combined under argon and heated to reflux for 4 h. The contents of the reaction flask were evaporated in vacuo. Saturated $NaHCO_3$ was added, and the aqueous layer was extracted with ether. The combined ether extracts were washed with brine, then dried with $Na_2SO_4$. Vacuum distillation afforded the product.

Step 2

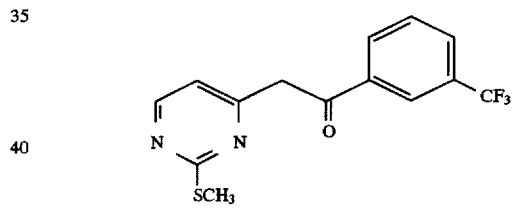

The target compound was prepared using the procedure set forth in Example 2, Step 1, replacing 4-picoline with the product of Step 1 and 4-fluoro-[N-methyl-N-methoxy] benzamide with 3-trifluoromethyl-(N-methyl-N-methoxy) benzamide.

Step 3

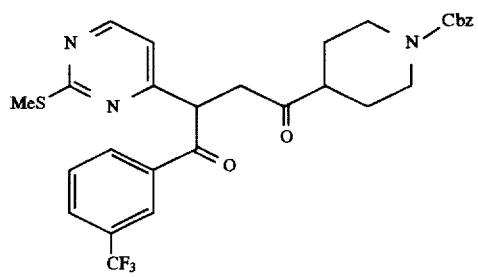

The target compound was prepared using the procedure set forth in Example 2, Step 3, using the product of Step 2.

Step 4

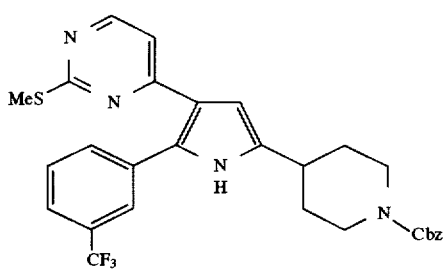

The target compound was prepared using the procedure of Example 2, Step 4 and the product of Step 3.

Step 5

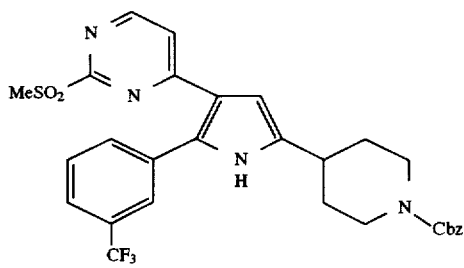

The product of step 4 (10.34 g, 18.7 mmol), sodium tungstonate (618 mg, 1.87 mmol), methanol (20 mL), ethyl acetate (100 mL), and 30% hydrogen peroxide (8.50 mL, 74.8 mmol) were combined under argon and heated to reflux. Saturated NaHCO₃ was added and the mixture was extracted with ethyl acetate. The combined organic extracts were washed with brine, then dried with Na₂SO₄. The mixture was evaporated in vacuo. The residue was flash chromatographed using ethyl acetate:hexane (60:40) to give the product.

Step 6

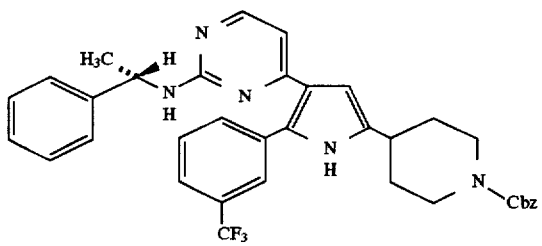

The product of Step 5 (998 mg, 1.71 mmol) and s-(−)-alpha-methylbenzylamine (2.20 mmol, 17.1 mmol) were combined and heated to 125° C. for 24 hrs. The reaction was poured into sat. NaHCO₃. The aqueous fraction was extracted with methylene chloride, washed with brine, dried with Na₂SO₄ then flash chromatographed using ethyl acetate:hexane (60:40) to yield product.

Step 7

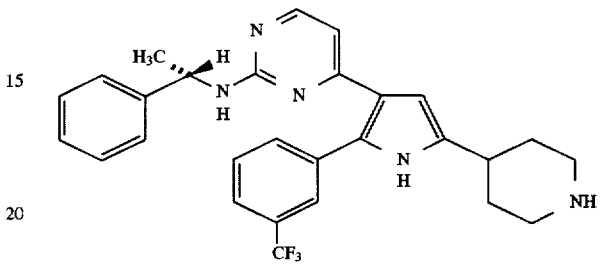

The product of step 6 (818 mg, 1.34 mmol) and 3N hydrochloric acid (10 mL) were combined and heated to reflux for 24 hrs. The solution was cooled, and washed with ether. The aqueous layer was made basic with NaOH (aq) then extracted with ethyl acetate. The combined organic extracts were washed with brine, dried with Na₂SO₄ then flash chromatographed using methylene chloride:methanol:ammonium hydroxide (80:20:2) to produce the target compound as a solid.

M. P. 123°–127° C.

¹H NMR (300 MHz, CD₃OD) δ: 7.95 (d, 1H); 7.75–7.50 (m, 4H); 7.30–7.10 (m, 5H); 6.52 (d, 1H); 6.34 (s, 1H); 4.80 (s, br, 1H); 3.40–3.20 (m, 3H); 3.00–2.80 (m, 3H); 2.15 (d, br, 2H); 1.90–1.70 (m, 2H); 1.38 (d, 3H).

EXAMPLE 117

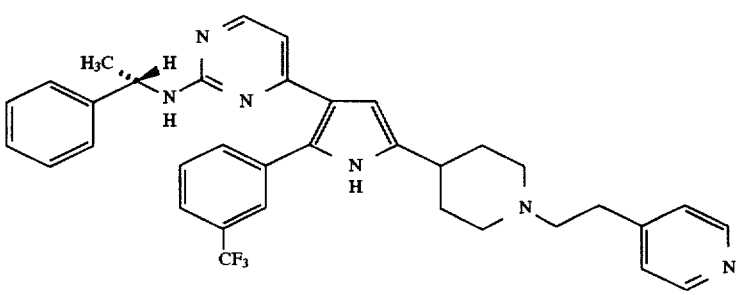

The compound of Example 116 (322 mg, 0.660 mmol), NaHCO₃ (61 mg, 0.727 mmol), 4-vinylpyridine (0.5 mL, 4.64 mmol), and methanol (4 mL) were heated at reflux. The reaction mixture was poured into sat NaHCO₃. The aqueous layer was extracted with methylene chloride, washed with brine, then dried with Na₂SO₄. Flash column chromatography using methylene chloride:methanol:ammonium hydroxide (95:5:0.5) yielded the product. Triturated with ether to get a solid.

M.P. 99°–109° C.

¹H NMR (300 MHz, CDCl₃): 8.50 (d, 2H); 8.40 (s, br, 1H); 8.06 (d, 1H); 7.75 (s, 1H); 7.65–7.55 (m, 2H); 7.49–7.39 (t, 1H); 7.35–7.14 (m, 7H); 6.48 (d, 1H); 6.39 (d, 1H); 5.25 (d, 1H); 5.00 (s, br, 1H); 3.10 (d, 2H); 2.90–2.80 (m, 2H); 2.70–2.58 (m, 3H); 2.22–2.10 (m, 2H); 2.08–1.75 (m, 5H); 1.45 (d, 3H).

EXAMPLE 118

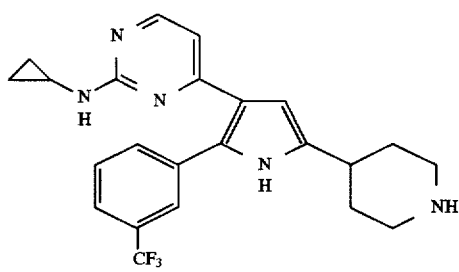

Step 1

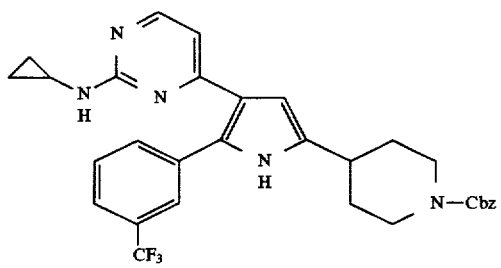

The target compound was prepared using steps 1–5 in Example 116, followed by reaction with cyclopropylamine using the procedure of Example 116, Step 6.

Step 2

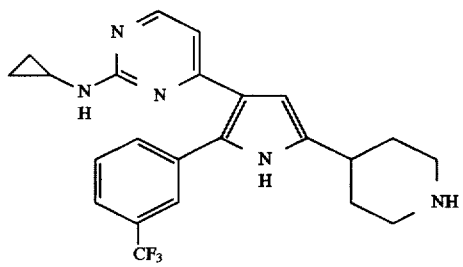

The product of Step 1 (500 mg, 0.886 mmol), methylene chloride (15 mL), and 30% hydrogen bromide in acetic acid (1.82 mL, 8.86 mmol) were combined with ice cooling under argon. After 2 hrs, the reaction solution was washed with ether. The aqueous layer was made basic with 2N sodium hydroxide, then extracted with ethyl acetate. The product was dried with Na₂SO₄ and crystallized using hexane:ethyl acetate (80:20).

M.P. 208°–209° C.

¹H NMR (300 MHz, CDCl₃): 8.30 (s, 1H); 8.10 (d, 2H); 7.90 (m, 1H); 7.70 (m, 1H); 7.60 (m, 1H); 7.50 (m, 1H); 6.59 (d, 1H); 6.44 (s, 1H); 5.20 (s, 1H); 3.20 (m, 2h); 2.80–2.60 (m, 4H); 2.05–1.95 (m, 2H); 1.80–1.60 (m, 4H); 0.80–0.60 (m, 2H); 0.50–0.40 (m, 2H).

EXAMPLE 119

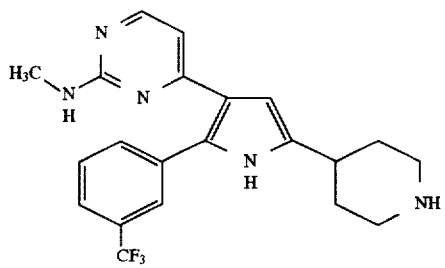

The target compound is prepared the procedure of Example 116, substituting methylamine in step 6.

M.P. 139°–141° C.

¹H NMR (300 MHz, CDCl₃): 8.35 (s, 1H); 8.10 (d, 1H); 7.80 (s, 1H); 7.70–7.40 (m, 3H); 6.50 (m, 2H); 4.90 (s, 1H); 3.25 (d, 2H); 2.90–2.70 (m, 6H); 2.10–1.90 (m, 3H); 1.80–1.60 (m, 2H).

EXAMPLE 120

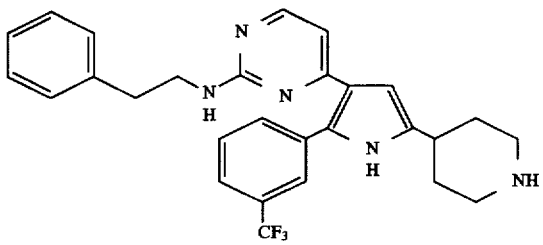

The target compound is prepared using the procedure of Example 116, substituting phenethylamine in Step 6.

M. P. 177°–178° C.

¹H NMR (300 MHz, CDCl₃): 8.30 (s, 1H); 8.10 (d, 1H); 7.75 (s, 1H); 7.65 (d, 1H); 7.50 (d, 1H); 7.45 (t, 1H); 7.33–7.10 (m, 4H); 6.50 (d, 1H); 6.45 (d, 1H); 4.95 (m, 1H); 3.60–3.40 (m, 2H); 3.20 (m, 2H); 2.85–2.66 (m, 5H); 2.00 (m, 2H); 1.80–1.60 (m, 2H).

EXAMPLE 121

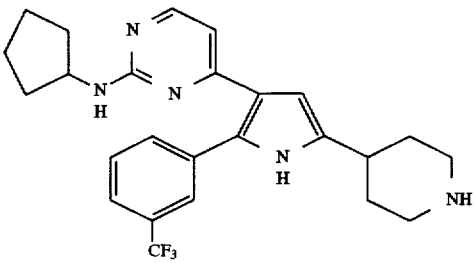

The target compound was prepared using the procedure of Example 116, substituting cyclopentylamine in Step 6.

M.P. 231°–232° C.

CHN anal for $C_{25}H_{28}F_3N_5 \cdot 0.15\ H_2O$: Calc C 65.52, H 6.23, N 15.28. Found: C 65.60, H 6.39, N 14.89.

EXAMPLE 122

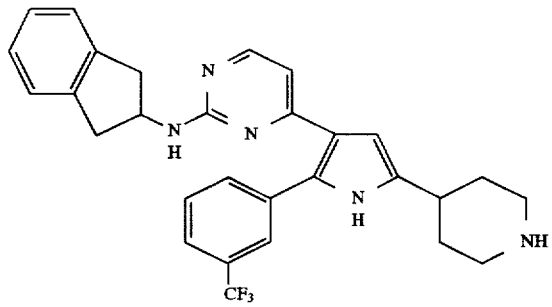

The target compound was prepared using the procedure of Example 116, substituting 2-aminoindane in Step 6.

M. P. 193°–194° C.

CHN anal for $C_{29}H_{28}F_3N_5 \cdot 0.20\ H_2O$: Calc C 68.67, H 5.64, N 13.81. Found: C 68.63, H 5.65, N 13.67.

The following compounds were prepared using the procedures set forth in Example 3.

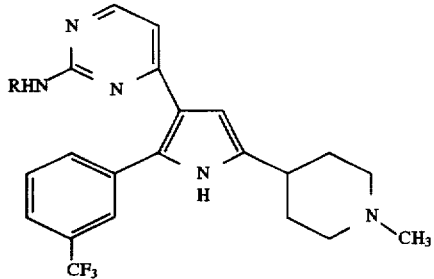

| EXAMPLE | R | M.P. (°C.) |
|---|---|---|
| 123 | cyclopropyl | 180–200 |
| 124 | methyl | 121–123 |
| 125 | phenethyl | 115–117 |
| 126* | s-α-Me-benzyl | 195–205 |

*Characterization data for Example 126 (dihydrochloride salt):

$^1$H NMR (300 MHz, CD$_3$OD): 11.70 (s, br, 1H); 7.96 (d, 1H); 7.85–7.62 (m, 4H); 7.30–7.18 (m, 3H); 7.10–6.90 (s, br, 3H); 6.68 (s, 1H); 4.60 (s, br, 1H); 3.65 (d, 2H); 3.30 (m, 3H); 3.25–3.10 (t, 2H); 3.00 (m, 1H); 2.30 (d, 2H); 2.00 (m, 2H); 1.40 (m, 2H). CHN anal. Calculated for C29H30F3N5.2HCl.1.0 H$_2$O: C. 58.39; H. 5.75; N. 11.74. Found: C. 58.56; H. 5.90; N. 11.35.

EXAMPLE 127

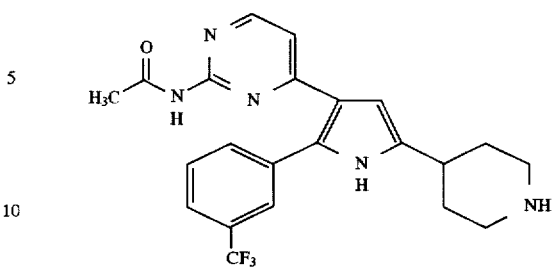

The target compound was prepared using the procedure set forth in Example 116, Steps 1–5, followed by reaction with ammonia in accordance with Example 116, Step 6.

Step 2

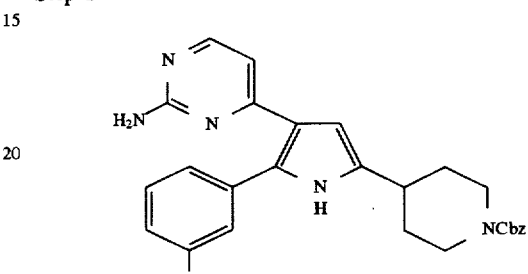

The product of step 1 (1.37 g, 2.62 mmol) and methylene chloride (10 mL) were cooled in an ice bath under argon. Acetic anhydride (0.344 mL, 3.65 mmol) and diisopropylethylamine (1.26 mL, 7.30 mmol) were added. The reaction was warmed to room temperature and then heated to reflux. The reaction was poured into sat'd. NaHCO$_3$. The aqueous fraction was extracted with methylene chloride, dried with Na$_2$SO$_4$ then flash chromatographed using ethyl acetate hexane (70:30) to yield a yellow foam.

Step 3

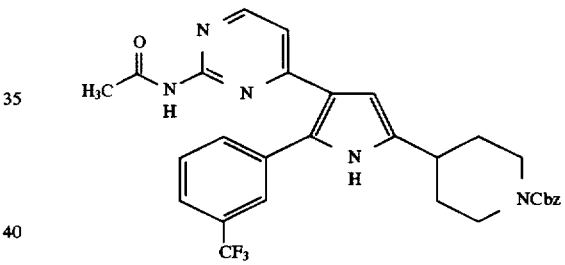

The target compound was prepared using the procedure of Example 118, Step 2.

M.P. 130°–140° C.

EXAMPLE 128

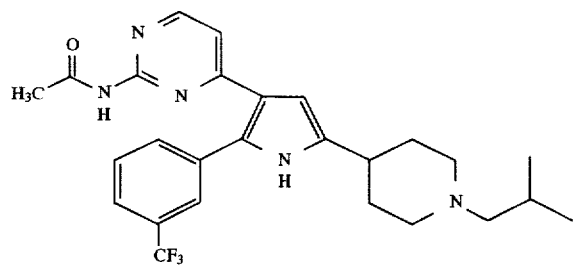

The compound of Example 127 (150 mg, 0.350 mmol), 1-bromo-2-methylpropane (0.053 mL, 0.490 mmol), NaHCO₃ (82 mg, 0.980 mmol) and acetonitrile (4 mL) were combined under argon and heated to 90° C. The mixture was poured into sat'd. NaHCO₃ and extracted with methylene chloride. The combined organic extracts were dried with Na₂SO₄ then flash chromatographed using methylene chloride:methanol:ammonium hydroxide (98:2:0.2). The target compound was crystallized from ethyl acetate.

M. P. 170°–180° C.

EXAMPLE 129

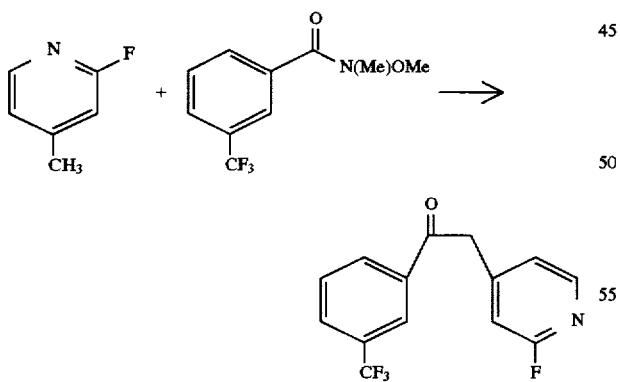

Step 1

The procedure described in Example 2, Step 1, but instead using 2-fluoro-4-picoline and 3-trifluoromethyl-(N-methyl-N-methoxy)-benzamide, was followed to give the desired product.

H¹ NMR (CDCl₃ 300 MHz): 4.38 (s, 2H), 6.83 (s, 1H), 7.05 (d, 1H), 7.68 (dd, 1H), 7.89 (d, 1H), 8.20 (dd, 2H), 8.25 (s, 1H).

Step 2

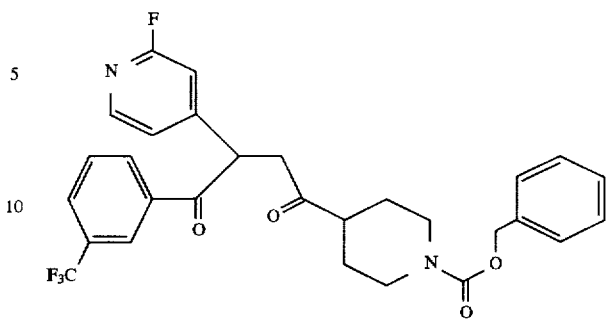

The procedure described in Example 2, step 3, but using sodium hydride (60% dispersion in mineral oil) in place of a 1M solution of sodium hexamethyldisilazide in THF, was followed to give the desired product.

H¹-NMR (CDCl₃, 300 MHz): 1.56 (bm, 2H); 1.85 (bm, 2H); 2.58 (m, 1H); 2.81 (dd, 1H); 2.89 (m, 2H); 3.66 (dd, 1H); 4.18 (bm, 2H); 5.14 (m, 3H); 6.84 (s, 1H); 7.10 (d, 1H), 7.35 (m, 5H) 7.58 (dd, 1H), 7.81 (d, 1H), 8.09 (d, 1H), 8.18 (dd, 2H).

Step 3

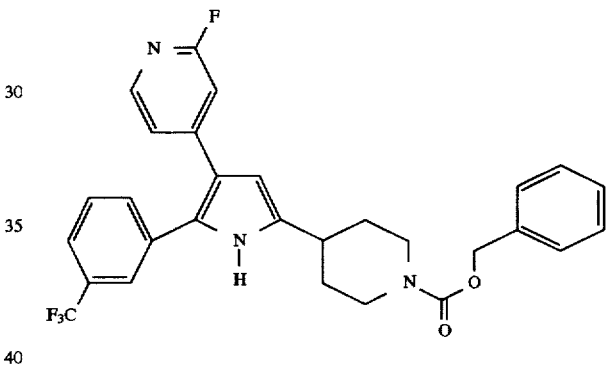

The procedure described in Example 2, Step 4 was followed, giving the desired product.

M. P. 184°–185° (ethyl acetate-hexanes).

Anal. Calcd. for C₂₉H₂₅F₄N₃O₂: C, 66.53; H, 4.81; N, 8.03. Found: C, 66.49; H, 4.85; N, 7.87.

EXAMPLE 130

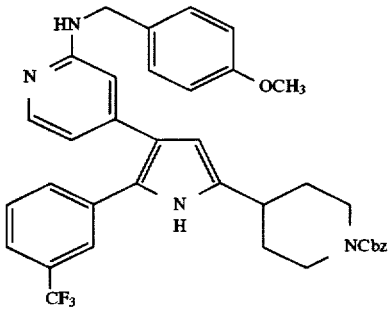

The compound of Example 129 (1.00 g, 1.91 mmol), and p-methoxybenzylamine (3.0 mL, 23.0 mmol) were combined under argon and heated to 130° C. for five days. The mixture was poured into sat'd. NaHCO₃ and extracted with methylene chloride. The combined organic extracts were dried with Na₂SO₄. Flash chromatography using hexane- :ethyl acetate (60:40) yielded an oil, which was crystallized using methanol.

M.P. 179°–180° C.

CHN anal. Calculated: C, 69.36; H, 5.51; N, 8.74. Found: C, 69.45; H, 5.58; N, 8.83.

EXAMPLE 131

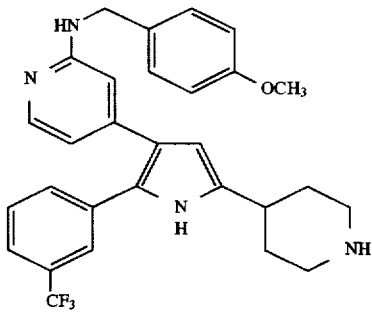

The compound of Example 130 (200 mg, 0.313 mmol) and palladium hydroxide (220 mg) were combined and hydrogenated at 55 psi. After 24 hrs the mixture was filtered and the filtrate evaporated in vacuo. Flash column chromatography using methylene chloride:methanol:ammonium hydroxide (95:5:0.5) yielded the target compound as a white solid.

M.P. 159°–160° C.

CHN anal. Calculated for C29H29F3N4O.0.20 H2O: C, 68.27; H, 5.81; N, 10.98. Found: C, 68.21; H, 5.63; N, 11.05.

EXAMPLE 132

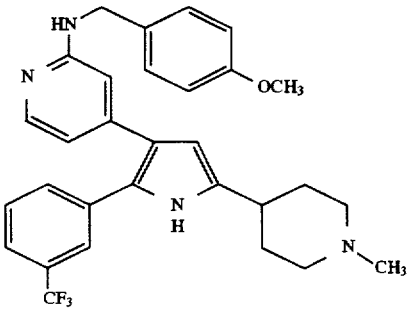

The target compound was prepared using the procedure of Example 3, substituting the compound from Example 130.

M.P. 205°–206° C.

CHN anal. Calculated for $C_{30}H_{31}F_3N_4O.0.35\ H_2O$: C, 68.38; H, 6.06; N, 10.63. Found: C, 68.44; H, 6.02; N, 10.49.

EXAMPLE 133

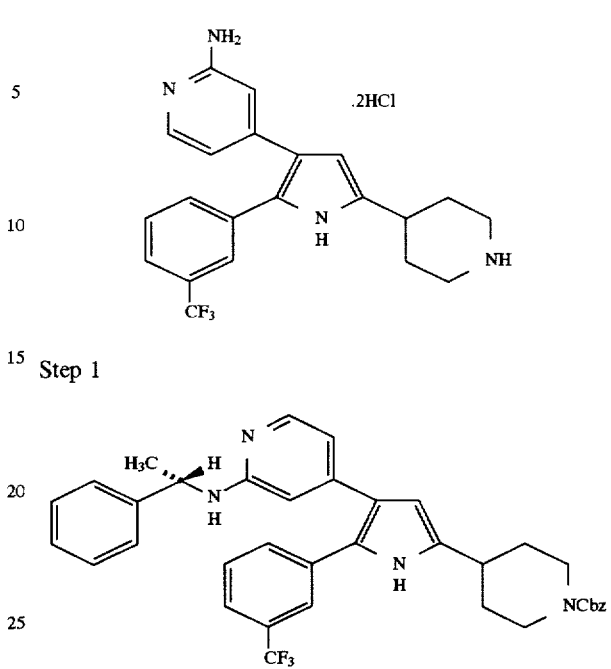

Step 1

The target compound was prepared using the procedure of Example 130, substituting s-(–)-alpha-benzylmethylamine. Step 2

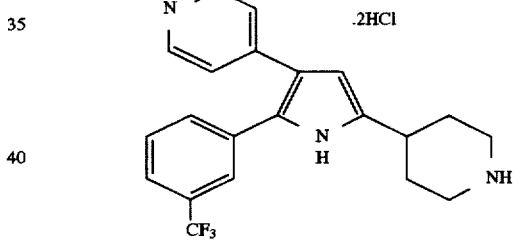

The target compound as the free base was prepared using the procedure of Example 132, Step 7. The dihydrochloride salt was prepared using 6N hydrogen chloride in ethanol.
M.P. 119°–135° C.

CHN anal. Calculated for $C_{21}H_{21}F_3N_4.0.45\ H_2O$: C, 53.95; H, 5.15; N, 11.99. Found: C, 54.01; H, 5.41; N, 11.99.

BIOLOGICAL ASSAYS

The ability of compounds of the present invention to inhibit cytokines can be demonstrated by the following in vitro assays.

Lipopolysaccharide mediated production of cytokines

Human peripheral blood mononuclear cells (PBMC) are isolated from fresh human blood according to the procedure of Chin and Kostura, *J. Immunol.* 151, 5574–5585 (1993). Whole blood is collected by sterile venipuncture into 60 mL syringes coated with 1.0 mL of sodium-heparin (Upjohn, 1000 U/mL) and diluted 1:1 in Hanks Balanced Salt Solution (Gibco). The erythrocytes are separated from the PBMC's by centrifugation on a Ficoll-Hypaque lymphocyte separation media. The PBMC's are washed three times in Hanks Balanced Salt Solution and then resuspended to a final concentration of $2\times10^6$ cell/mL in RPMI containing 10% fresh autologous human serum, penicillin streptomycin (10 U/mL) and 0.05% DMSO. Lipopolysaccharide (Salmonella type Re545; Sigma Chemicals) is added to the cells to a final concentration of 100 ng/mL. An aliquot (0.1 mL) of the cells is quickly dispensed into each well of a 96 well plate containing 0.1 mL of the test compound, at the appropriate dilution, and incubated for 24 hours. at 37° C. in 5% $CO_2$. At the end of the culture period, cell culture supernatants are assayed for IL-1$\beta$, TNF-$\alpha$, IL-6 and $PGE_2$ production using specific ELISA.

IL-1 mediated cytokine production

Human peripheral blood mononuclear cells are isolated from fresh human blood according to the procedure of Chin and Kostura. *J. Immunol.* 151, 5574–5585 (1993). Whole blood is collected by sterile venipuncture into 60 mL syringes coated with 1.0 mL of sodium-heparin (Upjohn, 1000 U/mL) and diluted 1:1 in Hanks Balanced Salt Solution (Gibco). The erythrocytes are separated from the PBMC's by centrifugation on a Ficoll-Hypaque lymphocyte separation media. The PBMC's are washed three times in Hanks Balanced Salt Solution and then resuspended to a final concentration of $2\times10^6$ cell/mL in RPMI cell culture medium containing 10% fresh autologous human serum, penicillin streptomycin (10 U/mL) and 0.05% DMSO. Endotoxin free recombinant human IL-1$\beta$ is then added to a final concentration of 50 pMolar. An aliquot (0.1 mL) of the cells is quickly dispensed into each well of a 96 well plate containing 0.1 mL of the compound at the appropriate dilution, and are incubated for 24 hours at 37° C. in 5% $CO_2$. At the end of the culture period, cell culture supernatants are assayed for TNF-$\alpha$, IL-6 and $PGE_2$ synthesis using specific ELISA.

Determination of IL-1$\beta$, TNF-$\alpha$, IL-6 and prostanoid production from LPS or IL-1 stimulated PBMC's IL-1$\beta$ ELISA Human IL-1$\beta$ can be detected in cell-culture supernatants or whole blood with the following specific trapping ELISA. Ninety-six well plastic plates (Immulon 4; Dynatech) are coated for 12 hours at 4° C. with 1 mg/mL protein-A affinity chromatography purified mouse anti-human IL-1b monoclonal antibody (purchased as an ascites preparation from LAO Enterprise, Gaithersburg, Md.) diluted in Dulbecco's phosphate-buffered saline (—$MgCl_2$, —$CaCl_2$). The plates are washed with phosphate buffered saline (PBS)-Tween (Kirkegaard and Perry) then blocked with 1% BSA diluent and blocking solution (Kirkegaard and Perry) for 60 minutes at room temperature followed by washing with PBS Tween.

IL-1$\beta$ standards are prepared from purified recombinant IL-1$\beta$ produced from *E. coli*. The highest concentration begins at 10 ng/mL followed by 11 two-fold serial dilutions. For detection of IL-1$\beta$ from cell culture supernatants or blood plasma, 10–25 mL of supernatant is added to each test well with 75–90 mL of PBS Tween. Samples are incubated at room temperature for 2 hours then washed 6 times with PBS Tween on an automated plate washer (Dennly). Rabbit anti-human IL-1$\beta$ polyclonal antisera diluted 1:500 in PBS-Tween is added to the plate and incubated for 1 hour at room temperature followed by six washes with PBS-Tween. Detection of bound rabbit anti-IL-1$\beta$ IgG is accomplished with Fab' fragments of Goat anti-rabbit IgG-horseradish peroxidase conjugate (Accurate Scientific) diluted 1:10,000 in PBS-Tween. Peroxidase activity was determined using TMB peroxidase substrate kit (Kirkegaard and Perry) with quantitation of color intensity on a 96-well plate Molecular Devices spectrophotometer set to determine absorbance at 450 nM. Samples are evaluated using a standard curve of absorbance versus concentration. Four-parameter logistics analysis generally is used to fit data and obtain concentrations of unknown compounds.

TNF-$\alpha$ ELISA

Immulon 4 (Dynatech) 96-well plastic plates are coated with a 0.5 mg/mL solution of mouse anti-human TNF-$\alpha$ monoclonal antibody. The secondary antibody is a 1:2500 dilution of a rabbit anti-human TNF-$\alpha$ polyclonal serum purchased from Genzyme. All other operations are identical to those described above for IL-1b. The standards are prepared in PBS-Tween+10% FBS or HS (human serum). Eleven 2 fold dilutions are made beginning at 20 ng/mL TNF-$\alpha$.

IL-6 ELISA

Levels of secreted human IL-6 are also determined by specific trapping ELISA as described previously in Chin and Kostura. *J. Immunol.* 151, 5574–5585 (1993). (Dynatech) ELISA plates are coated with mouse anti-human IL-6 monoclonal antibody diluted to 0.5 mg/ml in PBS. The secondary antibody, a rabbit anti-human IL-6 polyclonal antiserum, is diluted 1:5000 with PBS-Tween. All other operations are identical to those described above for IL-1$\beta$. The standards are prepared in PBS-Tween+10% FBS or HS. Eleven 2 fold dilutions are made beginning at 50 ng/mL IL-6.

$PGE_2$ production

Prostaglandin $E_2$ is detected in cell culture supernatants from LPS or IL-1 stimulated PBMC's using a commercially available enzyme immunoassay. The assay purchased from the Cayman Chemical (Catalogue number 514010) and is run exactly according to the manufacturers instructions.

Interleukin8 (IL-8)

The present compounds can also be assayed for IL-8 inhibitory activity as discussed below. Primary human umbilical cord endothelial cells (HUVEC) (Cell Systems, Kirland, Wash.) are maintained in culture medium supplemented with 15% fetal bovine serum (FBS) and 1% CS-HBGF (hemoglobin growth factor) consisting of aFGF (acid fibroblast growth factor) and heparin. The cells are then diluted 20-fold before being plated (250 µl) into gelatin coated 96-well plates. Prior to use, culture medium is replaced with fresh medium (200 µl). Buffer or test compound (25 µl, at appropriate concentrations) is then added to each well in quadruplicate wells and the plates incubated for 6 h in a humidified incubator at 37° C. in an atmosphere of 5% $CO_2$. At the end of the incubation period, supernatant is removed and assayed for IL-8 concentration using an IL-8 ELISA kit obtained from R&D Systems (Minneapolis, Minn.). All data is presented as mean value (ng/ml) of multiple samples based on the standard curve. $IC_{50}$ values where appropriate are generated by non-linear regression analysis.

The following non-limiting compounds are found to inhibit one or more cytokines at $IC_{50}$ concentrations of less than 100 µM.

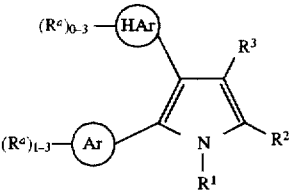

I

| $R^1$ | $(R^a)_{1-3}$—Ar | $(R^a)_{0-3}$—HAr | $R^3$ | $R^2$ |
|---|---|---|---|---|
| H | 4-F-Ph | 4-pyridyl | H | t-Bu |
| H | 4-F-Ph | 4-pyridyl | H | 4-(N—Cbz)-piperidinyl |
| H | 4-F-Ph | 4-pyridyl | H | 4-(N-Me)-piperidinyl |
| H | 4-F-Ph | 4-quinolinyl | H | 4-(N—Cbz)-piperidinyl |
| H | 4-F-Ph | 4-pyridyl | H | 4-piperidinyl |
| H | 4-F-Ph | 4-quinolinyl | H | 4-(N-Me)-piperidinyl |
| H | 4-F-Ph | 4-pyridyl | H | 4-(N—COCH$_2$NH$_2$)-piperidinyl |
| H | 4-F-Ph | 4-pyridyl | H | 4-(N—COCH$_3$)-piperidinyl |
| H | 4-F-Ph | 4-pyridyl | H | 4-(N—COCH$_2$NH-CO$_2$tBu)piperidinyl |
| H | 3-(CF$_3$)-Ph | 4-pyridyl | H | 4-(N—CBz)-piperidinyl |
| H | 3-(CF$_3$)-Ph | 4-pyridyl | H | 4-piperidinyl |
| H | 3-(CF$_3$)-Ph | 4-pyridyl | H | 4-(N-Me)-piperidinyl |
| H | 3-(CF$_3$)-Ph | 4-(2-F)-pyridyl | H | 4-(N—CBz)-piperidinyl |
| H | 3-(CF$_3$)-Ph | 4-pyridyl | H | 4-(N—CBz)-piperidinyl |
| H | 3-(CF$_3$)-Ph | 4-pyridyl | Me | 4-[N-SO$_2$Ph]-piperidinyl |
| H | 3-(CF$_3$)-Ph | 4-pyridyl | H | 4-(N-acetyl)-piperidinyl |
| H | 3,4-di-F-Ph | 4-pyridyl | Et | 4-(N-Me)-piperidinyl |
| H | 3,4-di-F-Ph | 4-pyridyl | Me | 4-(N-Me)-piperidinyl |
| H | 3,4-di-F-Ph | 4-pyridyl | —CO$_2$Et | 4-(N-Me)-piperidinyl |
| H | 3-(CF$_3$)-Ph | 4-pyridyl | —CO$_2$Et | 4-(N-Me)-piperidinyl |
| H | 3-(CF$_3$)-Ph | 4-pyridyl | CH$_3$ | 4-(N-Me)-piperidinyl |
| H | 3-(CF$_3$)-Ph | 4-pyridyl | CH$_3$ | 4-piperidinyl |
| H | 3-(CF$_3$)-Ph | ![structure: phenyl-CH(Me)-NH-C(=N)-N=CH-CH=C(Me)] | H | 4-piperidinyl |
| H | 3-(CF$_3$)-Ph | ![structure: phenyl-CH(Me)-NH-C(=N)-N=CH-CH=C(Me)] | H | ![structure: 4-piperidinyl-N-CH$_2$CH$_2$-4-pyridyl] |
| H | 3-(CF$_3$)-Ph | ![structure: cyclopropyl-NH-C(=N)-N=CH-CH=C(Me)] | H | 4-piperidinyl |
| H | 3-(CF$_3$)-Ph | ![structure: H$_3$CHN-C(=N)-N=CH-CH=C(Me)] | H | 4-piperidinyl |

-continued
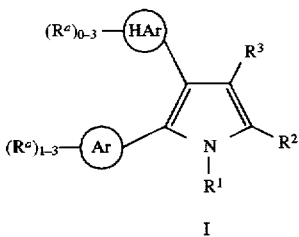
I
| R¹ | (Rᵃ)₁₋₃―Ar | (Rᵃ)₀₋₃―HAr | R³ | R² |
|---|---|---|---|---|
| H | 3-(CF₃)-Ph | 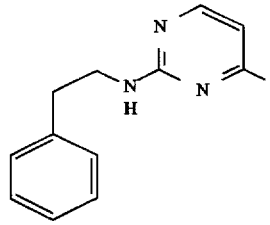 | H | 4-piperidinyl |
| H | 3-(CF₃)-Ph | 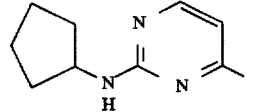 | H | 4-piperidinyl |
| H | 3-(CF₃)-Ph | 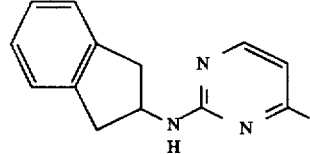 | H | 4-piperidinyl |
| H | 3-(CF₃)-Ph | 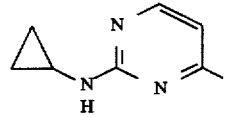 | H | N-methyl-piperidin-4-yl |
| H | 3-(CF₃)-Ph | 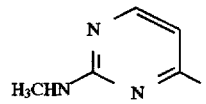 | H | N-methyl-piperidin-4-yl |
| H | 3-(CF₃)-Ph | 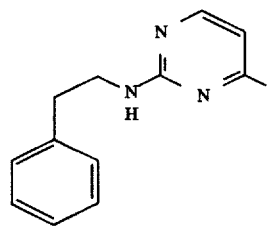 | H | N-methyl-piperidin-4-yl |
| H | 3-(CF₃)-Ph | 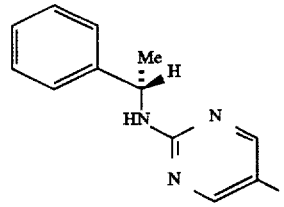 | H | N-methyl-piperidin-4-yl |

-continued

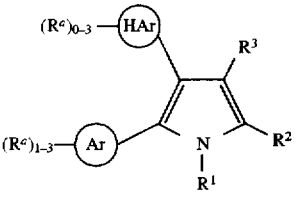

I

| R¹ | (Rᵃ)₁₋₃—(Ar) | (Rᵃ)₀₋₃—(HAr) | R³ | R² |
|---|---|---|---|---|
| H | 3-(CF₃)-Ph | 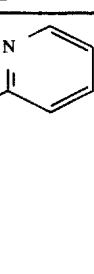 | H | 4-piperidinyl |
| H | 3-(CF₃)-Ph |  | H | 4-(N-Me)-piperidinyl |
| H | 3-(CF₃)-Ph | 4-pyridyl | —CO₂Et | 4-piperidinyl |
| H | 3-(CF₃)-Ph | 4-pyridyl | —CO₂Et | N-(2-ethylpyridin-4-yl)piperidin-4-yl |
| H | 3,4-di-F-phenyl | 4-pyridyl | —CO₂Et | 4-piperidinyl |
| CH₃ | 3-(CF₃)-Ph | 4-pyridyl | H | 4-(N-Me)-piperidinyl |

What is claimed is:

1. A compound represented by formula I:

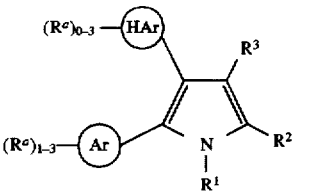

I or a pharmaceutically acceptable salt thereof, wherein:

(Ar) represents a $C_{5-10}$ aryl or pyridyl group substituted with 1-3 groups selected from $R^a$;

represents pyridyl unsubstituted or substituted with 1-3 $R^a$ groups;

each $R^a$ independently represents a member selected from the group consisting of: halo; CN, $NO_2$, $R^{21}$; $OR^{23}$; $SR^{23}$; $S(O)R^{21}$; $SO_2R^{21}$; $NR^{20}R^{23}$; $NR^{20}COR^{21}$; $NR^{20}CO_2R^{21}$; $NR^{20}CONR^{20}R^{23}$; $NR^{20}SO_2R^{21}$; $NR^{20}C(NR^{20})NHR^{20}$, $CO_2R^{23}$; $CONR^{20}R^{23}$; $SO_2NR^{20}R^{23}$; $SO_2NR^{20}COR^{21}$; $SO_2NR^{20}CONR^{20}R^{23}$; $OCONR^{20}R^{23}$; $OCONR^{20}SO_2R^{20}C(NR^{20})NR^{20}R^{23}$; $CONR^{20}SO_2R^{21}$ and $SO_2NR^{20}CO_2R^{21}$;

$R^1$ is selected from the group consisting of: H; $C_{1-15}$ alkyl, $C_{2-15}$ alkenyl, $C_{2-15}$ alkynyl, aryl and piperidinyl, said alkyl, alkenyl, aryl, alkynyl and piperidinyl being optionally substituted with from one to three members selected from the group consisting of: aryl, pyridyl, $OR^{20}$, $SR^{20}$, $N(R^{20})_2$, $S(O)R^{21}$, $SO_2R^{21}$, $SO_2N(R^{20})_2$, $SO_2NR^{20}COR^{21}$, $SO_2NR^{20}CONR^{20}R^{23}$, $NR^{20}COR^{21}$, $NR^{20}CO_2R^{21}$, $NR^{20}CONR^{20}R^{23}$, $N(R^{20})C(NR^{20})NHR^{20}$, $CO_2R^{20}$, $CONR^{20}R^{23}$, $CONR^{20}SO_2R^{21}$, $NR^{20}SO_2R^{21}$, $SO_2NR^{20}CO_2R^{21}$, $OCONR^{20}R^{23}$, $OCONR^{20}SO_2R^{21}$, and $C(O)OCH_2OC(O)R^{20}$;

$R^2$ is selected from the group consisting of: $C_{1-15}$ alkyl, $C_{2-15}$ alkenyl, $C_{2-15}$ alkynyl and piperidinyl, said alkyl, alkenyl and alkynyl optionally interrupted by 1-2 oxo or heteroatoms selected from O, S, S(O), $SO_2$ or $NR^{24}$; and said alkyl, alkenyl, alkynyl and piperidinyl being optionally substituted with from 1-3 of halo, piperidinyl, aryl($R^a$)₀₋₃, pyridyl, $OR^{20}$, $SR^{20}$, $NR^{20}R^{23}$, $S(O)R^{23}$, $SO_2R^{23}$, $SO_2NR^{20}R^{23}$, $SO_2NR^{20}COR^{21}$, $SO_2NR^{20}CONR^{20}R^{21}$, $NR^{20}COR^{23}$, $NR^{20}CO_2R^{23}$, $NR^{20}CONR^{20}R^{23}$, $N(R^{20})C(NR^{20})NHR^{20}$, $CO_2R^{20}$, $CONR^{20}R^{23}$, $CONR^{20}SO_2R^{21}$, $NR^{20}SO_2R^{21}$, $SO_2NR^{20}CO_2R^{21}$, $OCONR^{20}SO_2R^{23}$ and $OCONR^{20}R^{21}$;

$R^3$ is selected from the group consisting of: H, $C_{1-15}$ alkyl, $C_{2-15}$ alkenyl, $C_{2-15}$ alkynyl, halo, $CF_3$, $OCF_3$, $NO_2$, piperidinyl, CN, $S(O)R^{21}$, $SO_2R^{21}$, $COR^{20}$, $SO_2NR^{20}R^{23}$, $SO_2NR^{20}COR^{21}$, $SO_2NR^{20}CONR^{20}R^{23}$, $CO_2R^{20}$, $CONR^{20}R^{23}$, $CONR^{20}SO_2R^{21}$ and $SO_2NR^{20}CO_2R^{21}$; said alkyl, alkenyl, alkynyl and piperidinyl being optionally substituted with from one to three members selected from the group consisting of: halo, CN, aryl, pyridyl, $OR^{20}$, $SR^{20}$, $NR^{20}R^{23}$, $S(O)R^{21}$, $SO_2R^{21}$, $SO_2NR^{20}R^{23}$, $SO_2NR^{20}COR^{21}$, $SO_2NR^{20}CONR^{20}R^{23}$, $NR^{20}COR^{21}$, $NR^{20}CO_2R^{21}$, $NR^{20}CONR^{20}R^{23}$, $NR^{20}C(NR^{20})NHR^{20}$, $CO_2R^{20}$, $CONR^{20}R^{23}$, $CONR^{20}SO_2R^{21}$, $NR^{20}SO_2R^{21}$, $SO_2NR^{20}CO_2R^{21}$, $OCONR^{20}SO_2R^{21}$ and $OCONR^{20}R^{23}$;

$R^{20}$ represents a member selected from the group consisting of: H, $C_{1-15}$ alkyl, $C_{2-15}$ alkenyl, $C_{2-15}$ alkynyl, piperidinyl, aryl and pyridyl, said alkyl, alkenyl, aryl, pyridyl, piperidinyl and alkynyl being optionally substituted with 1–3 groups selected from halo, aryl and pyridyl;

$R^{21}$ represents a member selected from the group consisting of: $C_{1-15}$ alkyl, $C_{2-15}$ alkenyl, $C_{2-15}$ alkynyl, piperidinyl, aryl and pyridyl, said alkyl, alkenyl and alkynyl optionally interrupted by oxo and/or 1–2 heteroatoms selected from O, S, S(O), $SO_2$ or $NR^{24}$; said alkyl, alkenyl, alkynyl, aryl, piperidinyl and pyridyl being optionally substituted with from 1–3 of halo, piperidinyl, aryl, pyridyl, CN, $OR^{20}$, $O((CH_2)_n O)_m R^{20}$, $NR^{20}((CH_2)_n O)_m R^{20}$ wherein n represents an integer of from 2 to 4, and m represents an integer of from 1 to 3; $SR^{20}$, $NR^{20}R^{23}$, $S(O)R^{22}$, $SO_2R^{22}$, $SO_2NR^{20}R^{23}$, $SO_2NR^{20}COR^{22}$, $SO_2NR^{20}CONR^{20}R^{23}$, $NR^{20}COR^{22}$, $NR^{20}CO_2R^{22}$, $NR^{20}CONR^{20}R^{23}$, $NR^{22}C(NR^{22})NHR^{22}$, $CO_2R^{20}$, $CONR^{20}R^{23}$, $CONR^{20}SO_2R^{22}$, $NR^{20}SO_2R^{22}$, $SO_2NR^{20}CO_2R^{22}$, $OCONR^{20}SO_2R^{22}$, and $OCONR^{20}R^{23}$;

$R^{22}$ is selected from the group consisting of: $C_{1-15}$ alkyl, $C_{2-15}$ alkenyl, $C_{2-15}$ alkynyl, piperidinyl, aryl and pyridyl, said alkyl, alkenyl, and alkynyl being optionally substituted with 1–3 halo, aryl or pyridyl groups;

$R^{23}$ is $R^{21}$ or H;

$R^{24}$ is selected from aryl, $COR^{22}$, $CO_2R^{22}$, $CON(R^{20})_2$, $R^{23}$ and $SO_2R^{22}$;

and when two $R^{20}$ groups are present, when $R^{20}$ and $R^{21}$ are present, or when $R^{20}$ and $R^{23}$ are present, said two $R^{20}$ groups, $R^{20}$ and $R^{21}$ or said $R^{20}$ and $R^{23}$ may be taken in combination with the atoms to which they are attached and any intervening atoms and represent a piperidine ring.

2. A compound in accordance with claim 1 wherein $R^2$ represents a member selected from one of the following groups:

a) —$C_{1-7}$-straight or branched alkyl optionally interrupted by oxo or $NR^{24}$ and optionally substituted by 1–3 groups selected from the group consisting of: halo, piperidinyl, aryl($R^a)_{0-3}$, pyridyl, $OR^{20}$, $SR^{20}$, $NR^{20}R^{23}$, $S(O)R^{23}$, $SO_2R^{23}$, $SO_2NR^{20}R^{23}$, $SO_2NR^{20}COR^{21}$, $SO_2NR^{20}CONR^{20}R^{21}$, $NR^{20}COR^{23}$, $NR^{20}CO_2R^{23}$, $NR^{20}CONR^{20}R^{23}$, $N(R^{20})C(NR^{20})NHR^{20}$, $CO_2R^{20}$, $CONR^{20}R^{23}$, $CONR^{20}SO_2R^{21}$, $NR^{20}SO_2R^{21}$, $SO_2NR^{20}R^{21}$, $OCONR^{20}SO_2R^{23}$ and $OCONR^{20}R^{21}$;

b) —$C_{4-7}$-cycloalkyl optionally interrupted by oxo or $NR^{24}$ and optionally substituted by 1–3 groups selected from the group consisting of: halo, piperidinyl, aryl$(R^a)_{0-3}$, pyridyl, $OR^{20}$, $SR^{20}$, $NR^{20}R^{23}$, $S(O)R^{23}$, $SO_2R^{23}$, $SO_2NR^{20}R^{23}$, $SO_2NR^{20}COR^{21}$, $SO_2NR^{20}CONR^{20}R^{21}$, $NR^{20}COR^{23}$, $NR^{20}CO_2R^{23}$, $NR^{20}CONR^{20}R^{23}$, $N(R^{20})C(NR^{20})NHR^{20}$, $CO_2R^{20}$, $CONR^{20}R^{23}$, $CONR^{20}SO_2R^{21}$, $NR^{20}SO_2R^{21}$, $SO_2NR^{20}CO_2R^{21}$, $OCONR^{20}SO_2R^{23}$ and $OCONR^{20}R^{21}$;

c) —$C_{1-4}$-alkyl-aminoacyl-$C_{2-6}$-alkyl, the alkyl portions thereof being optionally interrupted by oxo or $NR^{24}$, and optionally substituted by 1–3 groups selected from the group consisting of: halo, piperidinyl, aryl$(R^a)_{0-3}$, pyridyl, $OR^{20}$, $SR^{20}$, $NR^{20}R^{23}$, $S(O)R^{23}$, $SO_2R^{23}$, $SO_2NR^{20}R^{23}$, $SO_2NR^{20}COR^{21}$, $SO_2NR^{20}CONR^{20}R^{21}$, $NR^{20}COR^{23}$, $NR^{20}CO_2R^{23}$, $NR^{20}CONR^{20}R^{23}$, $N(R^{20})C(NR^{20})NHR^{20}$, $CO_2R^{20}$, $CONR^{20}R^{23}$, $CONR^{20}SO_2R^{21}$, $NR^{20}SO_2R^{21}$, $SO_2NR^{20}CO_2R^{21}$, $OCONR^{20}SO_2R^{23}$ and $OCONR^{20}R^{21}$;

d) —$C_{1-4}$-alkyl-aminoacyl-$C_{4-7}$-cycloalkyl, the alkyl portions thereof being optionally interrupted by oxo or $NR^{24}$, and optionally substituted by 1–3 groups selected from the group consisting of: halo, piperidinyl, aryl$(R^a)_{0-3}$, pyridyl, $OR^{20}$, $SR^{20}$, $NR^{20}R^{23}$, $S(O)R^{23}$, $SO_2R^{23}$, $SO_2NR^{20}R^{23}$, $SO_2NR^{20}COR^{21}$, $SO_2NR^{20}CONR^{20}R^{21}$, $NR^{20}COR^{23}$, $NR^{20}CO_2R^{23}$, $NR^{20}CONR^{20}R^{23}$, $N(R^{20})C(NR^{20})NHR^{20}$, $CO_2R^{20}$, $CONR^{20}R^{23}$, $CONR^{20}SO_2R^{21}$, $NR^{20}SO_2R^{21}$, $SO_2NR^{20}CO_2R^{21}$, $OCONR^{20}SO_2R^{23}$ and $OCONR^{20}R^{21}$;

e) —$C_{1-4}$-alkyl-aminoacylamino-$C_{2-6}$-alkyl, the alkyl portions thereof being optionally interrupted by oxo or $NR^{24}$, and optionally substituted by 1–3 groups selected from the group consisting of: halo, piperidinyl, aryl$(R^a)_{0-3}$, pyridyl, $OR^{20}$, $SR^{20}$, $NR^{20}R^{23}$, $S(O)R^{23}$, $SO_2R^{23}$, $SO_2NR^{20}R^{23}$, $SO_2NR^{20}COR^{21}$, $SO_2NR^{20}CONR^{20}R^{21}$, $NR^{20}COR^{23}$, $NR^{20}CO_2R^{23}$, $NR^{20}CONR^{20}R^{23}$, $N(R^{20})C(NR^{20})NHR^{20}$, $CO_2R^{20}$, $CONR^{20}R^{23}$, $CONR^{20}SO_2R^{21}$, $NR^{20}SO_2R^{21}$, $SO_2NR^{20}CO_2R^{21}$, $OCONR^{20}SO_2R^{23}$ and $OCONR^{20}R^{21}$; and f) —$C_{1-4}$-alkyl-aminoacylamino-$C_{4-7}$-cycloalkyl, the alkyl portions thereof being optionally interrupted by oxo or $NR^{24}$, and optionally substituted by 1–3 groups selected from the group consisting of: halo, piperidinyl, aryl$(R^a)_{0-3}$, pyridyl, $OR^{20}$, $SR^{20}$, $NR^{20}R^{23}$, $S(O)R^{23}$, $SO_2R^{23}$, $SO_2NR^{20}R^{23}$, $SO_2NR^{20}COR^{21}$, $SO_2NR^{20}CONR^{20}R^{21}$, $NR^{20}COR^{23}$, $NR^{20}CO_2R^{23}$, $NR^{20}CONR^{20}R^{23}$, $N(R^{20})C(NR^{20})NHR^{20}$, $CO_2R^{20}$, $CONR^{20}R^{23}$, $CONR^{20}SO_2R^{21}$, $NR^{20}SO_2R^{21}$, $SO_2NR^{20}CO_2R^{21}$, $OCONR^{20}SO_2R^{23}$ and $OCONR^{20}R^{21}$.

3. A compound in accordance with claim 1 wherein:

(Ar) is selected from phenyl and pyridyl;

$R^a$ represents a member selected from the group consisting of: halo, CN, $R^{21}$, $OR^{23}$, $CO_2R^{23}$ and $CONR^{20}R^{23}$;

(HAr)

is pyridyl, $R^1$ is:

a) H or b) $C_{1-15}$ alkyl unsubstituted or substituted with 1–3 groups selected from the group consisting of: aryl, pyridyl, $OR^{20}$, $SR^{20}$, $N(R^{20})_2$, $S(O)R^{21}$, $SO_2R^{21}$, $SO_2N(R^{20})_2$, $SO_2NR^{20}COR^{21}$, $SO_2NR^{20}CONR^{20}R^{23}$, $NR^{20}COR^{21}$, $NR^{20}CO_2R^{21}$, $NR^{20}CONR^{20}R^{23}$, $N(R^{20})C(NR^{20})NHR^{20}$, $CO_2R^{20}$, $CONR^{20}R^{23}$, $CONR^{20}SO_2R^{21}$, $NR^{20}SO_2R^{21}$, $SO_2NR^{20}CO_2R^{21}$, $OCONR^{20}R^{23}$, $OCONR^{20}SO_2R^{21}$ and $C(O)OCH_2OC(O)R^{20}$;

$R^2$ is selected from the group consisting of:
a) —$C_{1-7}$-straight or branched alkyl optionally interrupted by oxo or $NR^{24}$, and optionally substituted by 1–3 groups selected from the group consisting of: halo, piperidinyl, aryl($R^a)_{0-3}$, pyridyl, $OR^{20}$, $SR^{20}$, $NR^{20}R^{23}$, $S(O)R^{23}$, $SO_2R^{23}$, $SO_2NR^{20}R^{23}$, $SO_2NR^{20}COR^{21}$, $SO_2NR^{20}CONR^{20}R^{21}$, $NR^{20}COR^{23}$, $NR^{20}CO_2R^{23}$, $NR^{20}CONR^{20}R^{23}$, $N(R^{20})C(NR^{20})NHR^{20}$, $CO_2R^{20}$, $CONR^{20}R^{23}$, $CONR^{20}SO_2R^{21}$, $NR^{20}SO_2R^{21}$, $SO_2NR^{20}CO_2R^{21}$, $OCONR^{20}SO_2R^{23}$ and $OCONR^{20}R^{21}$;

b) —$C_{4-7}$-cycloalkyl optionally interrupted by oxo or $NR^{24}$, and optionally substituted by 1–3 groups selected from the group consisting of: halo, piperidinyl, aryl($R^a)_{0-3}$, pyridyl, $OR^{20}$, $SR^{20}$, $NR^{20}R^{23}$, $S(O)R^{23}$, $SO_2R^{23}$, $SO_2NR^{20}R^{23}$, $SO_2NR^{20}COR^{21}$, $SO_2NR^{20}CONR^{20}R^{21}$, $NR^{20}COR^{23}$, $NR^{20}CO_2R^{23}$, $NR^{20}CONR^{20}R^{23}$, $N(R^{20})C(NR^{20})NHR^{20}$, $CO_2R^{20}$, $CONR^{20}R^{23}$, $CONR^{20}SO_2R^{21}$, $NR^{20}SO_2R^{21}$, $SO_2NR^{20}CO_2R^{21}$, $OCONR^{20}SO_2R^{23}$ and $OCONR^{20}R^{21}$;

c) —C1-4-alkyl-aminoacyl-$C_{2-6}$-alkyl, the alkyl portions thereof being optionally interrupted by oxo or $NR^{24}$, and optionally substituted by 1–3 groups selected from the group consisting of: halo, piperidinyl, aryl($R^a)_{0-3}$, pyridyl, $OR^{20}$, $SR^{20}$, $NR^{20}R^{23}$, $S(O)R^{23}$, $SO_2R^{23}$, $SO_2NR^{20}R^{23}$, $SO_2NR^{20}COR^{21}$, $SO_2NR^{20}CONR^{20}R^{21}$, $NR^{20}COR^{23}$, $NR^{20}CO_2R^{23}$, $NR^{20}CONR^{20}R^{23}$, $N(R^{20})C(NR^{20})NHR^{20}$, $CO_2R^{20}$, $CONR^{20}R^{23}$, $CONR^{20}SO_2R^{21}$, $NR^{20}SO_2R^{21}$, $SO_2NR^{20}CO_2R^{21}$, $OCONR^{20}SO_2R^{23}$ and $OCONR^{20}R^{21}$;

d) —$C_{1-4}$-alkyl-aminoacyl-$C_{4-7}$-cycloalkyl, the alkyl portions thereof being optionally interrupted by oxo or $NR^{24}$, and optionally substituted by 1–3 groups selected from the group consisting of: halo, piperidinyl, aryl($R^a)^{0-3}$, pyridyl, $OR^{20}$, $SR^{20}$, $NR^{20}R^{23}$, $S(O)R^{23}$, $SO_2R^{23}$, $SO_2NR^{20}R^{23}$, $SO_2NR^{20}COR^{21}$, $SO_2NR^{20}CONR^{20}R^{21}$, $NR^{20}COR^{23}$, $NR^{20}CO_2R^{23}$, $NR^{20}CONR^{20}R^{23}$, $N(R^{20})C(NR^{20})NHR^{20}$, $CO_2R^{20}$, $CONR^{20}R^{23}$, $CONR^{20}SO_2R^{21}$, $NR^{20}SO_2R^{21}$, $SO_2NR^{20}CO_2R^{21}$, $OCONR^{20}SO_2R^{23}$ and $OCONR^{20}R^{21}$;

e) —$C_{1-4}$-alkyl-aminoacylamino-$C_{2-6}$-alkyl, the alkyl portions thereof being optionally interrupted by oxo or $NR^{24}$, and optionally substituted by 1–3 groups selected from the group consisting of: halo, piperidinyl, aryl($R^a)_{0-3}$, pyridyl, $OR^{20}$, $SR^{20}$, $NR^{20}R^{23}$, $S(O)R^{23}$, $SO_2R^{23}$, $SO_2NR^{20}R^{23}$, $SO_2NR^{20}COR^{21}$, $SO_2NR^{20}CONR^{20}R^{21}$, $NR^{20}COR^{23}$, $NR^{20}CO_2R^{23}$, $NR^{20}CONR^{20}R^{23}$, $N(R^{20})C(NR^{20})NHR^{20}$, $CO_2R^{20}$, $CONR^{20}R^{23}$, $CONR^{20}SO_2R^{21}$, $NR^{20}SO_2R^{21}$, $SO_2NR^{20}CO_2R^{21}$, $OCONR^{20}SO_2R^{23}$ and $OCONR^{20}R^{21}$, and f) —$C_{1-4}$-alkyl-aminoacylamino-$C_{4-7}$-cycloalkyl, the alkyl portions thereof being optionally interrupted by oxo or $NR^{24}$, and optionally substituted by 1–3 groups selected from the group consisting of: halo, piperidinyl, aryl($R^a)_{0-3}$, pyridyl, $OR^{20}$, $SR^{20}$, $NR^{20}R^{23}$, $S(O)R^{23}$, $SO_2R^{23}$, $SO_2NR^{20}R^{23}$, $SO_2NR^{20}COR^{21}$, $SO_2NR^{20}CONR^{20}R^{21}$, $NR^{20}COR^{23}$, $NR^{20}CO_2R^{23}$, $NR^{20}CONR^{20}R^{23}$, $N(R^{20})C(NR^{20})NHR^{20}$, $CO_2R^{20}$, $CONR^{20}R^{23}$, $CONR^{20}SO_2R^{21}$, $NR^{20}SO_2R^{21}$, $SO_2NR^{20}CO_2R^{21}$, $OCONR^{20}SO_2R^{23}$ and $OCONR^{20}R^{21}$;

and $R^3$ is selected from the group consisting of:
a) H,
b) alkyl,
c) halo,
d) $CO_2R^{20}$,
e) $CONR^{20}R^{23}$ and
f) CN.

4. A compound in accordance with claim 1 wherein:

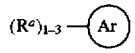

is selected from the group consisting of:
4-fluorophenyl,
4-chlorophenyl,
3-fluorophenyl,
3-chlorophenyl,
3-methylphenyl,
3,4-dichlorophenyl,
3-hydroxyphenyl,
2-chlorophenyl,
4-aminomethylphenyl,
4-nitrophenyl,
3,4-difluorophenyl,
2-methoxyphenyl,
3-methoxyphenyl,
4-methoxyphenyl,
4-methylsulfinylphenyl, and
4-methylsulfonylphenyl;

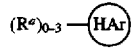

is selected from the group consisting of:
4-pyridyl,
4-(2-methylpyridyl),
4-(2-aminopyridyl),
4-(2-methoxypyridyl),
4-(3-methylpyridyl),
2-(N-t-butoxycarbonylamino)-4-pyridyl,
4-(2-N-acetylamino)-pyridyl,
4-(2-N-benzolylamino-3-methyl)-pyridyl and
4-(2-N-benzolylamino)-pyridyl;

$R^1$ is: H;
$R^2$ is selected from the group consisting of:
isopropyl,
tert-butyl,
phenethyl,
benzyl,
2-amino-2,2-dimethylethyl,
4-aminomethylbenzyl,
piperidin-4-yl,
piperidin-3-yl,
N-methylpiperidin-4-yl,
N-benzylpiperidin-4-yl,
N-(2-hydroxyethyl)piperidin-4-yl,
N-methanesulfonylpiperidin-4-yl,
isobutyl,
N-(benzyloxycarbonyl)-piperidin-4-yl,
N-(phenyl)-piperidin-4-yl,
N-(methyl)-piperidin-4-yl-methyl,
N-methyl-piperidin-3-yl, and $R^3$ is selected from the group consisting of:
a) H,
b) F,
c) Cl,

89 d) Br,
d) $CO_2R^{20}$,
e) $CONR^{20}R^{23}$ and
f) CN.

5. A compound in accordance with claim 1 wherein:

$(R^a)_{1-3}$—(Ar)

is selected from the group consisting of:
4-fluorophenyl,
4-chlorophenyl,
3-fluorophenyl,
3-chlorophenyl,
3-methylphenyl,
3,4-dichlorophenyl,
3-hydroxyphenyl,
2-chlorophenyl,
4-aminomethylphenyl,
4-nitrophenyl,
3,4-difluorophenyl,
2-methoxyphenyl,
3-methoxyphenyl,
4-methoxyphenyl,
3-trifluoromethylphenyl,
4-methylsulfinylphenyl, and
4-methylsulfonylphenyl;

$(R^a)_{0-3}$—(HAr)

is selected from the group consisting of:
4-pyridyl,
4-(2-methylpyridyl),
4-(2-aminopyridyl),
4-(2-methoxypyridyl),
4-(3-methylpyridyl),
2-(N-t-butoxycarbonylamino)-4-pyridyl,
4-(2-N-acetylamino)-pyridyl,
4-(2-N-benzolylamino-3-methyl)-pyridyl and
4-(2-N-benzolylamino)-pyridyl;

$R^1$ is: $C_{1-15}$ alkyl;
$R^2$ is selected from the group consisting of:
isopropyl,
tert-butyl,
phenethyl,
benzyl,
2-amino-2,2-dimethylethyl,
4-aminomethylbenzyl,
piperidin-4-yl,
piperidin-3-yl,
N-methylpiperidin-4-yl,
N-benzylpiperidin-4-yl,
N-(2-hydroxyethyl)piperidin-4-yl,
N-methanesulfonylpiperidin-4-yl,
isobutyl,
N-(benzyloxycarbonyl)-piperidin-4-yl,
N-(phenyl)-piperidin-4-yl,
N-(methyl)-piperidin-4-yl-methyl,
N-methyl-piperidin-3-yl, and $R^3$ is selected from the group consisting of:
a) H,
b) F,
c) Cl,
d) Br,
d) $CO_2R^{20}$,

90 e) $CONR^{20}R^{23}$ and
f) CN.

6. A compound represented by formula I:

or a pharmaceutically acceptable salt thereof, wherein:
(Ar) represents a $C_{5-10}$ aryl or pyridyl group, substituted with 1–3 groups selected from $R^a$;

(HAr)

represents pyridyl unsubstituted or substituted with 1–3 $R^a$ groups;

each $R^a$ independently represents a member selected from the group consisting of: halo; CN, $NO_2$, $R^{21}$; $OR^{23}$; $SR^{23}$; $S(O)R^{21}$; $SO_2R^{21}$; $NR^{20}R^{23}$; $NR^{20}COR^{21}$; $NR^{20}CO_2R^{21}$; $NR^{20}CONR^{20}R^{23}$; $NR^{20}SO_2R^{21}$; $NR^{20}C(NR^{20})NHR^{20}$, $CO_2R^{23}$; $CONR^{20}R^{23}$; $SO_2NR^{20}R^{23}$; $SO_2NR^{20}COR^{21}$; $SO_2NR^{20}CONR^{20}R^{23}$; $SO_2NR^{20}CO_2R^{21}$; $OCONR^{20}R^{23}$; $OCONR^{20}SO_2R^{20}$ and $C(NR^{20})NR^{20}R^{23}$;

$R^1$ is selected from the group consisting of: H; $C_{1-15}$ alkyl, $C_{2-15}$ alkenyl, $C_{2-15}$ alkynyl, aryl and piperidinyl, said alkyl, alkenyl, aryl, alkynyl and piperidinyl being optionally substituted with from one to three members selected from the group consisting of: aryl, pyridyl, $OR^{20}$, $SR^{20}$, $N(R^{20})_2$, $S(O)R^{21}$, $SO_2R^{21}$, $SO_2N(R^{20})_2$, $SO_2NR^{20}COR^{21}$, $SO_2NR^{20}CON(R^{20})_2$, $NR^{20}COR^{21}$, $NR^{20}CO_2R^{21}$, $NR^{20}CON(R^{20})_2$, $N(R^{20})C(NR^{20})NHR^{20}$, $CO_2R^{20}$, $CON(R^{20})_2$, $CONR^{20}SO_2R^{21}$, $NR^{20}SO_2R^{21}$, $SO_2NR^{20}CO_2R^{21}$, $OCON(R^{20})_2$, $OCONR^{20}SO_2R^{21}$, $C(O)OCH_2OC(O)R^{20}$ and $OCONR^{20}R^{23}$;

$R^2$ is selected from the group consisting of: $C_{1-15}$ alkyl, $C_{2-15}$ alkenyl, $C_{2-15}$ alkynyl and, piperidinyl, said alkyl, alkenyl and alkynyl being optionally interrupted by 1–2 heteroatoms selected from O, S, S(O), $SO_2$ or $NR^{24}$; and said alkyl, alkenyl, alkynyl and piperidinyl being optionally substituted with from 1–3 of halo, aryl, pyridyl, $OR^{20}$, $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CON(R^{20})_2$, $NR^{20}COR^{22}$, $NR^{20}CO_2R^{22}$, $NR^{20}CON(R^{20})_2$, $N(R^{22})C(NR^{22})NHR^{22}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$ and $OCONR^{20}R^{23}$;

$R^3$ is selected from the group consisting of: H, $C_{1-15}$ alkyl, $C_{2-15}$ alkenyl, $C_{2-15}$ alkynyl, halo, $CF_3$, $NO_2$ and piperidinyl, said alkyl, alkenyl, alkynyl and piperidinyl being optionally substituted with from one to three members selected from the group consisting of: halo, CN, aryl, pyridyl, $OR^{20}$, $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CON(R^{20})_2$, $NR^{20}COR^{22}$, $NR^{20}CO_2R^{22}$, $NR^{20}CON(R^{20})_2$, $NR^{22}C(NR^{22})NHR^{22}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$ and $OCONR^{20}R^{23}$;

$R^{20}$ represents a member selected from the group consisting of: H, $C_{1-15}$ alkyl, $C_{2-15}$ alkenyl, $C_{2-15}$ alkynyl, piperidinyl, aryl and pyridyl, said alkyl, alkenyl and alkynyl being optionally substituted with 1–3 groups selected from halo, aryl and pyridyl;

$R^{21}$ represents a member selected from the group consisting of: $C_{1-15}$ alkyl, $C_{2-15}$ alkenyl, $C_{2-15}$ alkynyl, aryl and pyridyl, optionally interrupted by 1–2 heteroatoms selected from O, S, S(O), $SO_2$ or $NR^{24}$; said alkyl, alkenyl, alkynyl, aryl and pyridyl being optionally substituted with from 1–3 of halo, piperidinyl, aryl, pyridyl, CN, $OR^{20}$, $O((CH_2)_nO)_mR^{20}$, $NR^{20}((CH_2)_nO)_mR^{20}$ wherein n represents an integer of from 2 to 4, and m represents an integer of from 1 to 3; $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CON(R^{20})_2$, $NR^{20}COR^{22}$, $NR^{20}CO_2R^{22}$, $NR^{20}CON(R^{20})_2$, $NR^{22}C(NR^{22})NHR^{22}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$, $OCONHR^{20}R^{23}$ and $OCON(R^{20})_2$;

$R^{22}$ is selected from the group consisting of: $C_{1-15}$ alkyl, $C_{2-15}$ alkenyl, $C_{2-15}$ alkynyl, piperidinyl, aryl and pyridyl, said alkyl, alkenyl, and alkynyl being optionally substituted with 1–3 halo, aryl or pyridyl groups;

$R^{23}$ is $R^{21}$ or H;

$R^{24}$ is selected from aryl, $COR^{22}$, $CO_2R^{22}$, $CON(R^{20})_2$, $R^{23}$ and $SO_2R^{22}$;

n is 1–4;

m is 1–4;

and when two $R^{20}$ groups are present, when $R^{20}$ and $R^{21}$ are present, or when $R^{20}$ and $R^{23}$ are present, said two $R^{20}$ groups, $R^{20}$ and $R^{21}$ or said $R^{20}$ and $R^{23}$ may be taken in combination with the atoms to which they are attached and any intervening atoms and represent a piperidine ring.

7. A compound in accordance with claim 6 wherein:

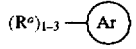 is selected phenyl and pyridyl,

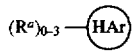

is pyridyl, $R^1$ is H or substituted alkyl;

$R^2$ is selected from the group consisting of:
a) —$C_{1-7}$-alkyl optionally interrupted by 1 nitrogen atom and optionally substituted by: oxo or $NR^{23}$,
b) —$C_{4-7}$-cycloalkyl optionally interrupted by 1 nitrogen atom and optionally substituted by: oxo or $NR^{23}$,
c) —$C_{1-4}$-alkyl-aminoacyl-$C_{2-6}$-alkyl optionally interrupted by 1 nitrogen atom and optionally substituted by oxo or $NR^{23}$,
d) —$C_{1-4}$-alkyl-aminoacyl-$C_{4-7}$-cycloalkyl optionally interrupted by 1 nitrogen atom and optionally substituted by: oxo, $NR^{23}$ or $NR^{24}$,
e) —$C_{1-4}$-alkyl-aminoacylamino-$C_{2-6}$-alkyl optionally interrupted by 1 nitrogen atom and optionally substituted by: oxo, $NR^{23}$ or
f) —$C_{1-4}$-alkyl-aminoacylamino-$C_{4-7}$-cycloalkyl optionally interrupted by 1 nitrogen atom and optionally substituted by: oxo, $NR^{23}$ or $NR^{24}$; wherein the point of attachment to the pyrrole is from the left hand side of the items listed in a through f; and $R^3$ is:
a) H,
b) alkyl,
c) halo, or
d) $CO_2R^{20}$.

8. A compound in accordance with claim 6 wherein:

is selected from the group consisting of:
phenyl,
4-fluorophenyl,
4-chlorophenyl,
3-fluorophenyl,
3-chlorophenyl,
3-methylphenyl,
3,4-dichlorophenyl, and
3-hydroxyphenyl;

is selected from the group consisting of:
4-pyridyl,
4-(2-methylpyridyl),
4-(2-aminopyridyl),
4-(2-methoxypyridyl),
4-(3-methylpyridyl);

$R^1$ is: H;

$R^2$ is selected from the group consisting of:
a) isopropyl,
b) tert-butyl,
c) phenethyl,
d) benzyl,
e) 2-amino-2,2-dimethylethyl,
f) 4-aminomethylbenzyl,
g) glycylaminomethyl,
h) (L)-alanylaminomethyl,
i) 2-amino-2,2-dimethylacetylaminomethyl,
j) N,N-dimethylaminoethyl-N-methylaminocarbonylaminomethyl,
k) 3-piperidinecarbonylaminomethyl,
l) 4-piperidinecarbonylaminomethyl,
m) piperidin-4-yl,
n) piperidin-3-yl,
o) pyrrolidin-3-yl,
p) N-methylpiperidin-4-yl,
q) N-benzylpiperidin-4-yl,
r) N-(2-hydroxyeth-1-yl)piperidin-4-yl and
s) N-methanesulfonylpiperidin-4-yl; and $R^3$ is selected from the group consisting of:
a) H,
b) F,
c) Cl and
d) Br.

9. A compound in accordance with claim 6 wherein:

 is phenyl or pyridyl,

is pyridyl;

$R^a$ is selected from the group consisting of: halo; CN, $R^{21}$, $OR^{23}$, $CO_2R^{23}$ and $CONR^{20}R^{23}$;

$R^1$ is: H or unsubstituted or substituted alkyl;

$R^2$ is selected from the group consisting of:
a) $C_{1-7}$-straight or branched alkyl optionally interrupted by oxo or $NR^{24}$ and optionally substituted by: $NR^{20}R^{23}$;

b) $C_{4-7}$-cycloalkyl optionally interrupted by oxo or $NR^{24}$ and optionally substituted by: $NR^{20}R^{23}$;

c) $C_{1-4}$-alkyl-aminoacyl-$C_{2-6}$-alkyl, the alkyl portions thereof being optionally interrupted by oxo or $NR^{24}$ and optionally substituted by: $NR^{20}R^{23}$;

d) $C_{1-4}$-alkyl-aminoacyl-$C_{4-7}$-cycloalkyl, the alkyl portions thereof being optionally interrupted by oxo or $NR^{24}$ and optionally substituted by: $NR^{20}R^{23}$;

e) $C_{1-4}$-alkyl-aminoacylamino-$C_{2-6}$-alkyl, the alkyl portions thereof being optionally interrupted by oxo or $NR^{24}$ and optionally substituted by: $NR^{20}R^{23}$; or f) $C_{1-4}$-alkyl-aminoacylamino-$C_{4-7}$-cycloalkyl, the alkyl portions thereof being optionally interrupted by oxo or $NR^{24}$ and optionally substituted by: $NR^{20}R^{23}$; wherein the point of attachment to the pyrrole is from the left hand side of the items listed in a through f; and $R^3$ is selected from the group consisting of:
a) H,
b) halo,
c) alkyl,
d) $CO_2R^{20}$,
e) $CONR^{20}R^{23}$ or
f) CN.

10. A compound in accordance with claim 6 wherein:

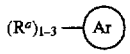

is selected from the group consisting of:
4-fluorophenyl,
4-chlorophenyl,
3-fluorophenyl,
3-chlorophenyl,
3-methylphenyl,
3,4-dichlorophenyl,
3-hydroxyphenyl,
2-chlorophenyl,
4-aminomethylphenyl,
4-nitrophenyl,
3,4-difluorophenyl,
2-methoxyphenyl,
3-methoxyphenyl,
4-methoxyphenyl,
3-trifluoromethylphenyl,
4-methylsulfinylphenyl, and
4-methylsulfonylphenyl;

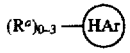

is selected from the group consisting of:
4-pyridyl,
4-(2-methylpyridyl),
4-(2-aminopyridyl),
4-(2-methoxypyridyl),
2-(N-t-butoxycarbonylamino)-4-pyridyl,
4-(2-N-acetylamino)-pyridyl,
4-(2-N-benzolylamino-3-methyl)-pyridyl and
4-(2-N-benzolylamino)-pyridyl;

$R^1$ is: H;
$R^2$ is selected from the group consisting of:
isopropyl,
tert-butyl,
phenethyl,
benzyl,
2-amino-2,2-dimethylethyl,
4-aminomethylbenzyl,
piperidin-4-yl,
piperidin-3-yl,
N-methylpiperidin-4-yl,
N-benzylpiperidin-4-yl,
N-(2-hydroxy-ethyl)piperidin-4-yl,
N-methanesulfonylpiperidin-4-yl,
isobutyl,
N-CBz-piperidin-4-yl,
N-Bn-piperidin-4-yl,
N-Ph-piperidin-4-yl,
$CH_2$-4-(N-Me)-piperidin-4-yl,
3-N-Me-piperidinyl, $R^3$ is selected from the group consisting of:
a) H,
b) F,
c) Cl,
d) Br,
d) $CO_2R^{20}$,
e) $CONR^{20}R^{23}$ or
f) CN.

11. A compound in accordance with claim 6 wherein:

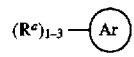

is selected from the group consisting of:
4-fluorophenyl,
4-chlorophenyl,
3-fluorophenyl,
3-chlorophenyl,
3-methylphenyl,
3,4-dichlorophenyl,
3-hydroxyphenyl,
2-chlorophenyl,
4-aminomethylphenyl,
4-nitrophenyl,
3,4-difluorophenyl,
2-methoxyphenyl,
3-methoxyphenyl,
4-methoxyphenyl,
3-trifluoromethylphenyl,
4-methylsulfinylphenyl, and
4-methylsulfonylphenyl;

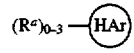

is selected from the group consisting of:
4-pyridyl,
4-(2-methylpyridyl),
4-(2-aminopyridyl),
4-(2-methoxypyridyl),
4-(3-methylpyridyl),
2-(N-Boc-amino)-4-pyridyl,
4-(2-N-acetylamino)-pyridyl,
4-(2-N-benzolylamino-3-methyl)-pyridyl and
4-(2-N-benzolylamino)-pyridyl;

$R^1$ is: $C_{1-15}$ alkyl;
$R^2$ is selected from the group consisting of:
isopropyl,
tert-butyl,
phenethyl,
benzyl,
2-amino-2,2-dimethylethyl, 4-aminomethylbenzyl,
piperidin-4-yl,
piperidin-3-yl,
N-methylpiperidin-4-yl,
N-benzylpiperidin-4-yl,
N-(2-hydroxy-ethyl)piperidin-4-yl,
N-methanesulfonylpiperidin-4-yl,
isobutyl,
N-CBz-piperidin-4-yl,
N-Bn-piperidin-4-yl,
N-Ph-piperidin-4-yl,
$CH_2$-4-(N-Me)-piperidin-4-yl,
3-N-Me-piperidinyl, $R^3$ is selected from the group consisting of:
a) H,
b) F,
c) Cl,
d) Br,
e) $CO_2R^{20}$,
f) $CONR^{20}R^{23}$ or
g) CN.

12. A compound according to claim 1 falling within one of the following tables:

TABLE I

| $R^2$ | $(R^e)_{1-3}$—Ar | $(R^e)_{0-3}$—HAr |
|---|---|---|
| t-butyl | Ph-4-F | 3-methyl-4-pyridyl |
| t-butyl | Ph-4-F | 2-methyl-4-pyridyl |
| N-Bn-piperidin-4-yl | Ph-4-F | 4-pyridyl |
| N-Ph-piperidin-4-yl | Ph-4-F | 4-pyridyl |
| N-Me-piperidin-4-yl | Ph-4-Cl | 4-pyridyl |
| N-Me-piperidin-4-yl | Ph-3,4-di-F | 4-pyridyl |
| N-Me-piperidin-4-yl | Ph-3-Cl | 4-pyridyl |
| t-butyl | Ph-2-OMe | 4-pyridyl |
| t-butyl | Ph-3-OMe | 4-pyridyl |
| t-butyl | Ph-4-OMe | 4-pyridyl |
| t-butyl | Ph-4-Cl | 4-pyridyl |
| t-butyl | Ph-3-Cl | 4-pyridyl |
| t-butyl | Ph-3,4-di-F | 4-pyridyl |
| t-butyl | Ph-3,4-di-Cl | 4-pyridyl |
| t-butyl | Ph-3-$CF_3$ | 4-pyridyl |
| t-butyl | Ph-4-SMe | 4-pyridyl |
| t-butyl | Ph-4-S(O)Me | 4-pyridyl |
| 4-piperidinyl | Ph-4-F | 4-pyridyl |
| N-Me-piperidin-3-yl | Ph-4-F | 4-pyridyl |
| t-butyl | Ph-4-$NO_2$ | 4-pyridyl |
| t-butyl | Ph-4-$NMe_2$ | 4-pyridyl |
| t-butyl | Ph-2-Cl | 4-pyridyl |
| N—CBz-piperidin-4-yl | Ph-2-$CF_3$ | 4-(2-F)-pyridyl |
| N-methylpiperidin-4-yl | Ph-4-F | 2-methylpyridin-4-yl |
| N-methylpiperidin-4-yl | Ph-3-$CF_3$ | 2-methylpyridin-4-yl |

Me = methyl, CBz = benzyloxycarbonyl Bn = benzyl Ph = phenyl Boc = butoxycarbonyl

TABLE II

| $R^2$ | $(R^e)_{1-3}$—Ar | $(R^e)_{0-3}$—HAr | $R^3$ |
|---|---|---|---|
| t-butyl | Ph-4-F | 2-methyl-4-pyridyl | CN |
| t-butyl | Ph-4-F | 2-methyl-4-pyridyl | COMe |
| t-butyl | Ph-4-F | 2-methyl-4-pyridyl | CONHMe |
| t-butyl | Ph-4-F | 2-methyl-4-pyridyl | $SO_2Et$ |
| t-butyl | Ph-4-F | 2-methyl-4-pyridyl | COOEt |
| t-buytl | Ph-4-F | 4-(2-amino)-pyridyl | CN |
| t-butyl | Ph-4-F | 4-(2-N-benzyl-amino)-pyridyl | CN |
| t-butyl | Ph-4-F | 4-(2-acetylamino)-pyridyl | COMe |
| t-butyl | Ph-4-F | 4-pyridyl | CN |
| t-butyl | Ph-4-F | 4-pyridyl | CONH-iBu |
| t-butyl | Ph-4-F | 4-pyridyl | COMe |
| i-butyl | Ph-4-F | 4-pyridyl | CN |
| N-Me-piperidin-4-yl | Ph-4-F | 4-pyridyl | COMe |
| N-Bn-piperidin-4-yl | Ph-4-F | 4-pyridyl | COMe |
| N-Ph-piperidin-4-yl | Ph-4-F | 4-pyridyl | COMe |
| N-Me-piperidin-4-yl | Ph-4-F | 4-pyridyl | CN |
| N-Me-piperidin-4-yl | Ph-4-Cl | 4-pyridyl | CN |
| t-butyl | Ph-2-OMe | 4-pyridyl | CN |
| t-butyl | Ph-3-OMe | 4-pyridyl | CN |
| t-butyl | Ph-4-OMe | 4-pyridyl | CN |
| t-butyl | Ph-4-Cl | 4-pyridyl | CN |
| t-butyl | Ph-3-Cl | 4-pyridyl | CN |
| t-butyl | Ph-3,4-di-Cl | 4-pyridyl | CN |
| t-butyl | Ph-3-$CF_3$ | 4-pyridyl | CN |
| t-butyl | Ph-4-S-Me | 4-pyridyl | CN |
| t-butyl | Ph-4-S(O)-Me | 4-pyridyl | CN |
| 4-piperidinyl | Ph-4-F | 4-pyridyl | CN |
| 3-N-Me-piperidinyl | Ph-4-F | 4-pyridyl | CN |
| t-butyl | Ph-4-$NO_2$ | 4-pyridyl | CN |
| t-butyl | Ph-4-$NMe_2$ | 4-pyridyl | CN |
| t-butyl | Ph-2-Cl | 4-pyridyl | CN |
| 4-piperidinyl | Ph-4-F | 4-pyridyl | CN |
| t-butyl | Ph-4-F | 2-pyridyl | CN |
| t-butyl | Ph-4-F | 2-methyl-4-pyridyl | CN |
| t-butyl | Ph-4-F | 3-methyl-4-pyridyl | CN |
| cyclohexyl | Ph-4-F | 4-pyridyl | CN |
| i-propyl | Ph-4-F | 4-pyridyl | CN |
| 1-cyclopropyl-ethyl | Ph-4-F | 4-pyridyl | CN |
| t-butyl | Ph-4-F | 2,4-dimethylpyridin-4-yl | CN |
| 4-(N—Cbz)-piperidinyl | Ph-4-F | 4-pyridyl | H |
| 4-(N—Cbz)-piperidinyl | 3-($CF_3$)-Ph | 4-(2-F)-pyridyl | |
| t-butyl | Ph-4-F | 2,6-dimethylpyridyl | CN |

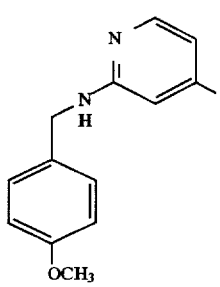

| (Rᵃ)₁₋₃—Ar | (Rᵃ)₀₋₃—HAr | R | R¹ |
|---|---|---|---|
| 3,4-di-F—C₆H₃ | 4-C₅H₄N | CH₃ | CH₃ |
| 3-CF₃—C₆H₄ | 4-C₅H₄N | Ethyl | CH₃ |
| 3-CF₃—C₆H₄ | 4-C₅H₄N | CH₃ | CH₃ |
| 3-CF₃—C₆H₄ | 4-C₅H₄N | CH₃ | H |
| 3-CF₃—C₆H₄ | 4-C₅H₄N | CH₃ | SO₂C₆H₅ |

I

| R¹ | (Rᵃ)₁₋₃—Ar | (Rᵃ)₀₋₃—HAr | R³ | R² |
|---|---|---|---|---|
| H | 4-F-Ph | 4-pyridyl | H | t-Bu |
| H | 4-F-Ph | 4-pyridyl | H | 4-(N—Cbz)-piperidinyl |
| H | 4-F-Ph | 4-pyridyl | H | 4-(N-Me)-piperidinyl |
| H | 4-F-Ph | 4-pyridyl | H | 4-piperidinyl |
| H | 4-F-Ph | 4-pyridyl | H | 4-(N—COCH₂NH₂)-piperidinyl |
| H | 4-F-Ph | 4-pyridyl | H | 4-(N—COCH₃)-piperidinyl |
| H | 4-F-Ph | 4-pyridyl | H | 4-(N—COCH₂NH—CO₂tBu)piperidinyl |
| H | 3-(CF₃)-Ph | 4-pyridyl | H | 4-(N—CBz)-piperidinyl |
| H | 3-(CF₃)-Ph | 4-pyridyl | H | 4-piperidinyl |
| H | 3-(CF₃)-Ph | 4-pyridyl | H | 4-(N-Me)-piperidinyl |
| H | 3-(CF₃)-Ph | 4-(2-F)-pyridyl | H | 4-(N—CBz)-piperidinyl |
| H | 3-(CF₃)-Ph | 4-pyridyl | H | 4-(N—CBz)-piperidinyl |
| H | 3-(CF₃)-Ph | 4-pyridyl | Me | 4-[N—SO₂Ph]-piperidinyl |
| H | 3-(CF₃)-Ph | 4-pyridyl | H | 4-(N-acetyl)-piperidinyl |
| H | 3,4-di-F-Ph | 4-pyridyl | Et | 4-(N-Me)-piperidinyl |
| H | 3,4-di-F-Ph | 4-pyridyl | Me | 4-(N-Me)-piperidinyl |
| H | 3,4-di-F-Ph | 4-pyridyl | —CO₂Et | 4-(N-Me)-piperidinyl |
| H | 3-(CF₃)-Ph | 4-pyridyl | —CO₂Et | 4-(N-Me)-piperidinyl |
| H | 3-(CF₃)-Ph | 4-pyridyl | CH₃ | 4-(N-Me)-piperidinyl |
| H | 3-(CF₃)-Ph | 4-pyridyl | CH₃ | 4-piperidinyl |
| H | 3-(CF₃)-Ph | [4-methyl-2-pyridyl-NH-CH₂-(4-methoxyphenyl)] | H | 4-piperidinyl |

-continued
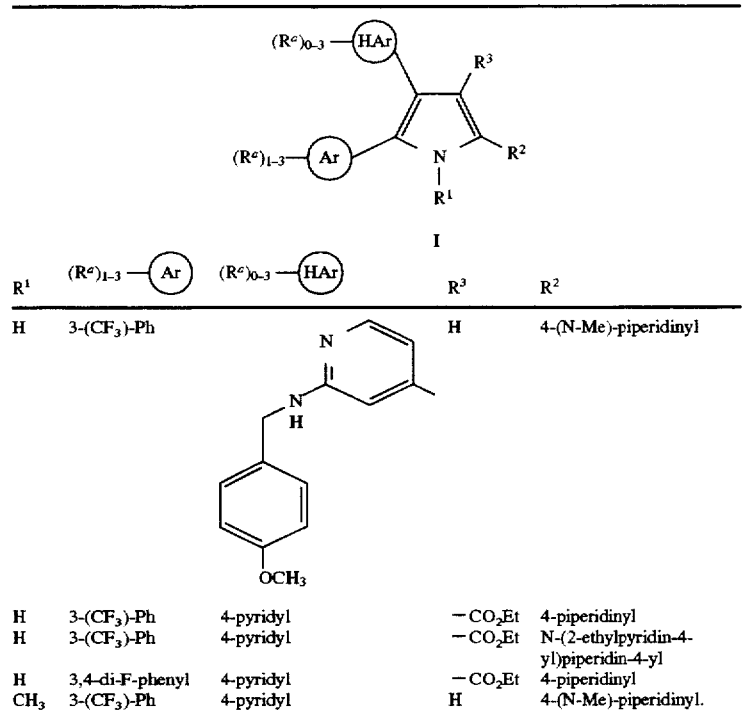
| R¹ | (Rᵃ)₁₋₃—Ar | (Rᶜ)₀₋₃—HAr | R³ | R² |
|---|---|---|---|---|
| H | 3-(CF₃)-Ph | (2-pyridylamino-CH₂-C₆H₄-OCH₃ group) | H | 4-(N-Me)-piperidinyl |
| H | 3-(CF₃)-Ph | 4-pyridyl | —CO₂Et | 4-piperidinyl |
| H | 3-(CF₃)-Ph | 4-pyridyl | —CO₂Et | N-(2-ethylpyridin-4-yl)piperidin-4-yl |
| H | 3,4-di-F-phenyl | 4-pyridyl | —CO₂Et | 4-piperidinyl |
| CH₃ | 3-(CF₃)-Ph | 4-pyridyl | H | 4-(N-Me)-piperidinyl. |
13. A compound in accordance with claim 1 represented by one of the following structural formulas:
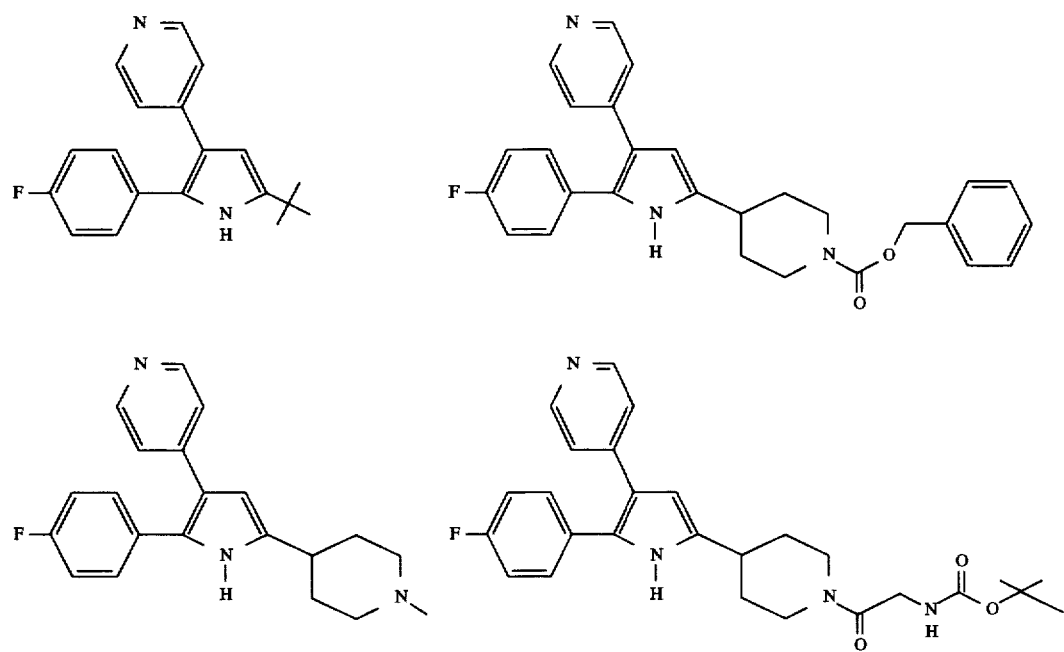

-continued
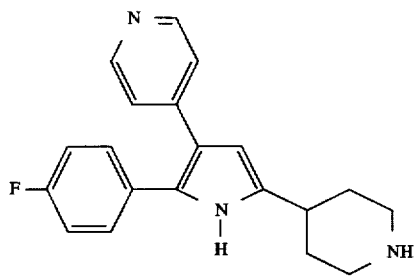
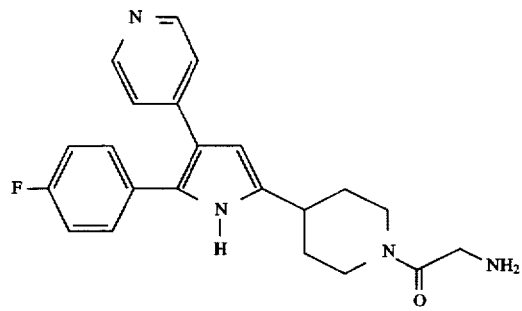
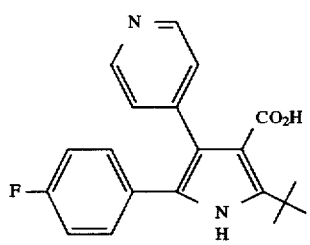
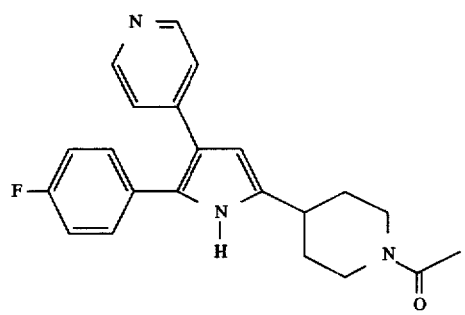
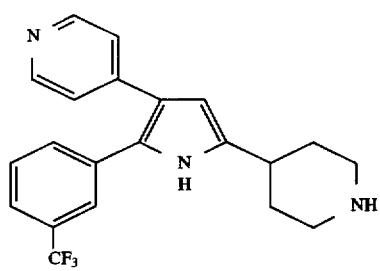
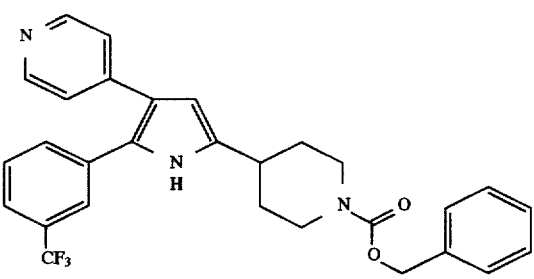
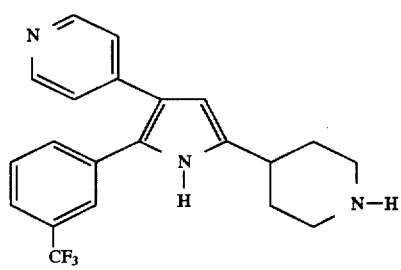
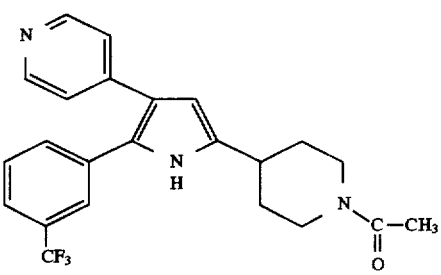
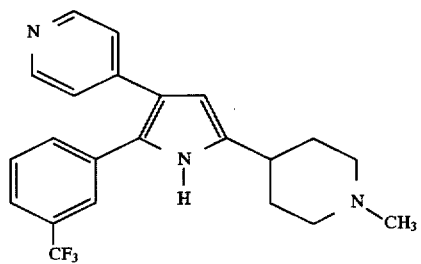
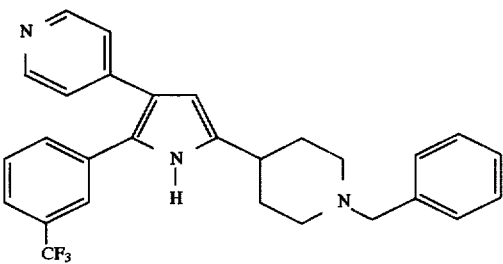

-continued
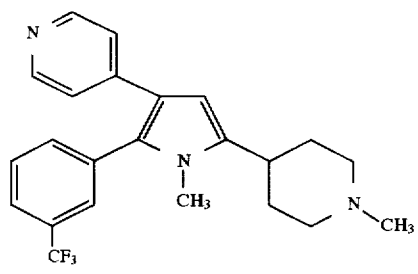 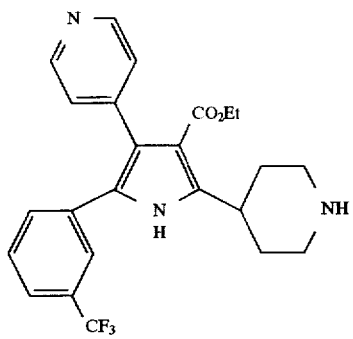
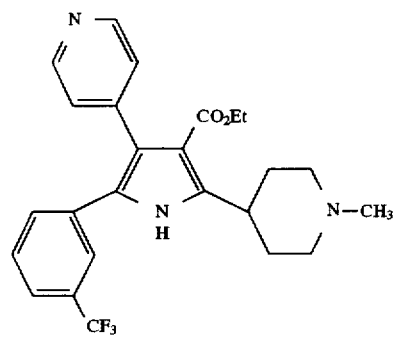 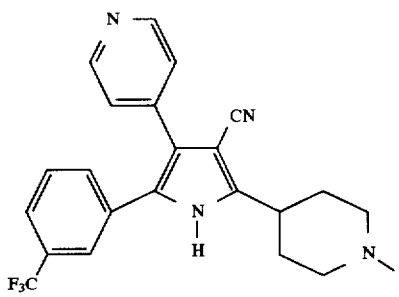
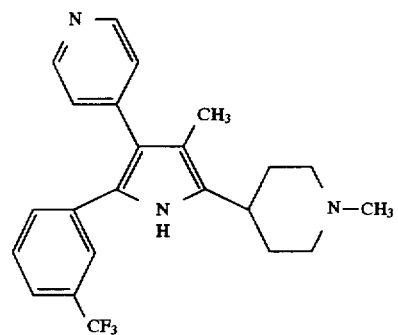 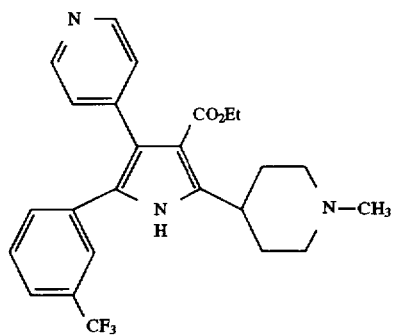
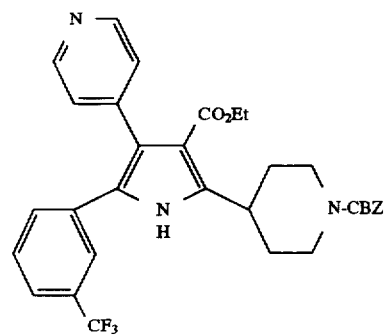 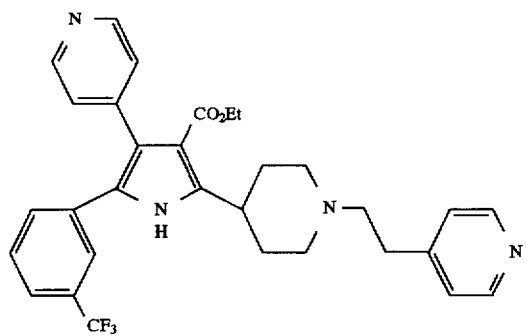

-continued
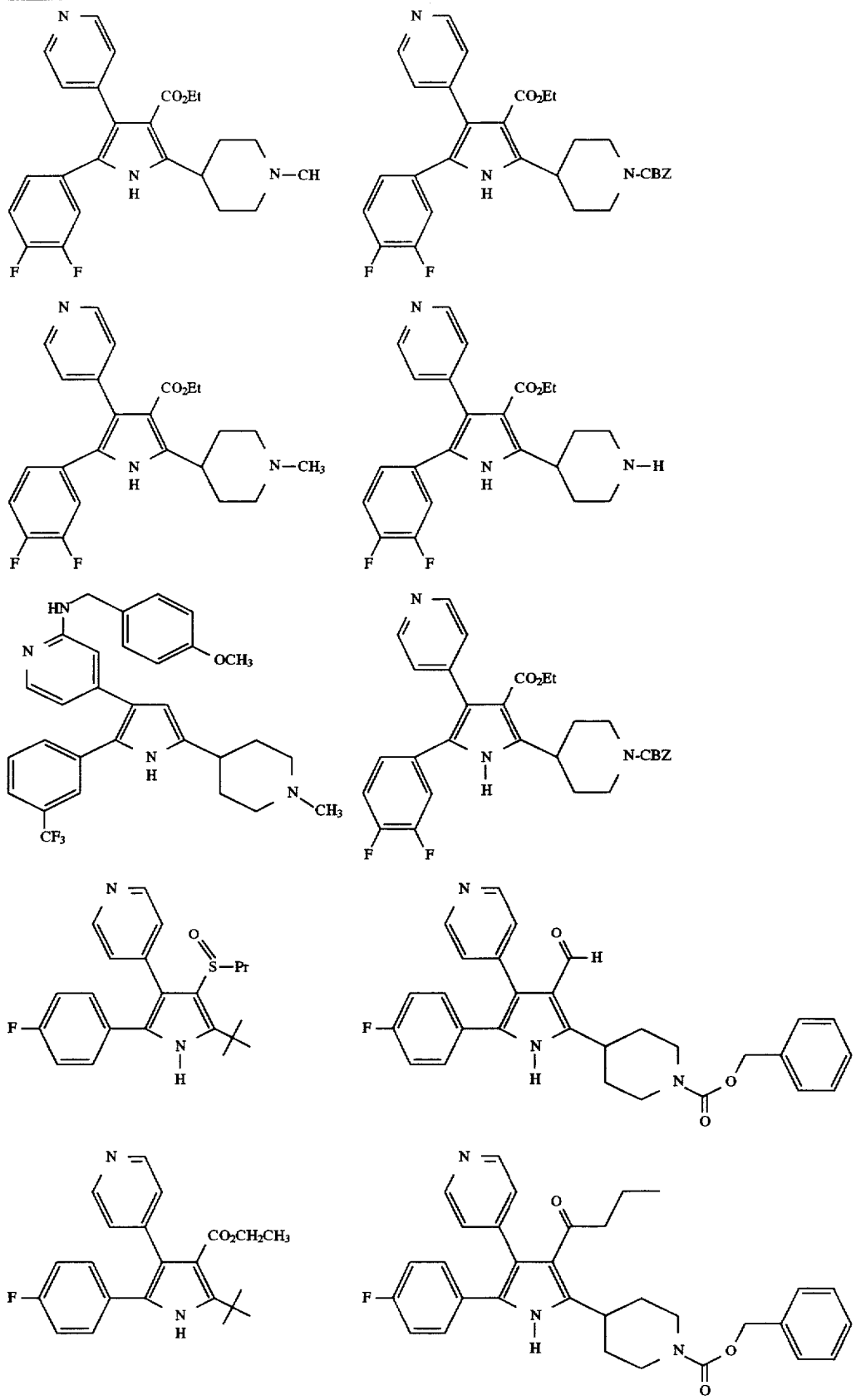

-continued
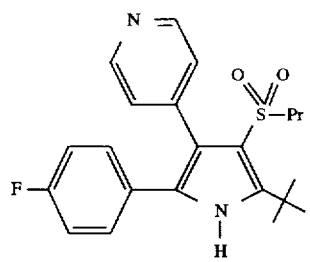
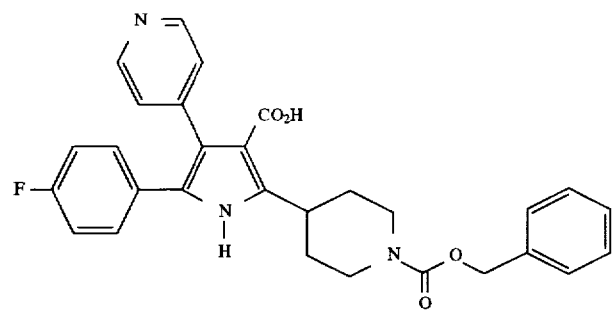
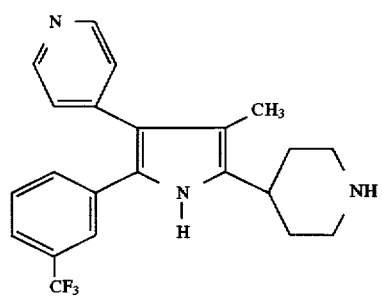
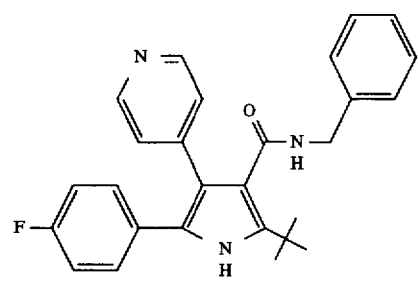
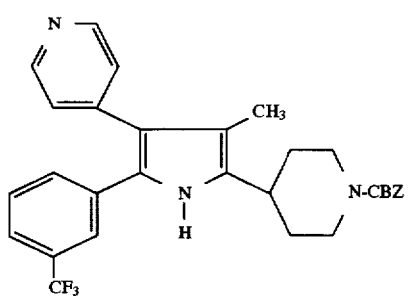
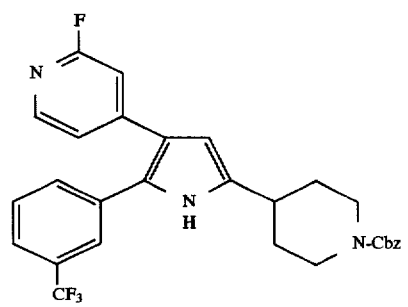
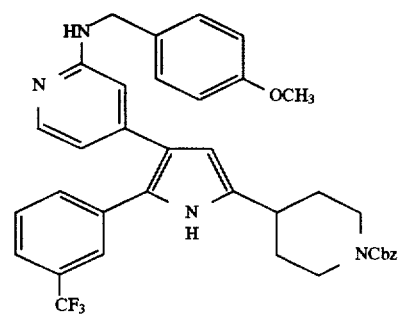

-continued
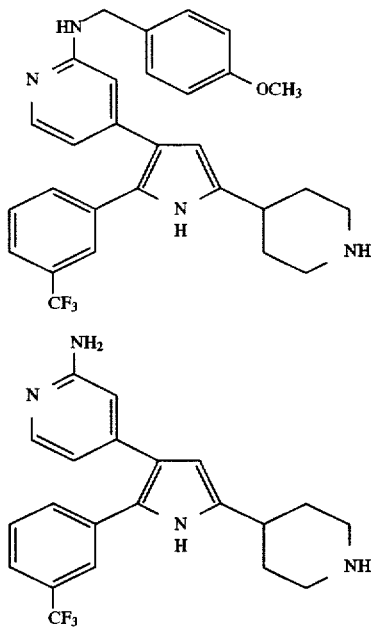
* * * * *